US007427675B2

(12) United States Patent
Capaldi et al.

(10) Patent No.: US 7,427,675 B2
(45) Date of Patent: Sep. 23, 2008

(54) COMPOUNDS AND METHODS FOR THE CHARACTERIZATION OF OLIGONUCLEOTIDES

(75) Inventors: Daniel C. Capaldi, Carlsbad, CA (US); Hans-Joachim Josef Gaus, Carlsbad, CA (US); Claus Andre Frank Rentel, Vista, CA (US); Philip Dmitri Olsen, San Diego, CA (US); Christine C. Kurata, La Jolla, CA (US); Quanlai Song, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 232 days.

(21) Appl. No.: 11/209,160

(22) Filed: Aug. 22, 2005

(65) Prior Publication Data

US 2006/0040308 A1 Feb. 23, 2006

Related U.S. Application Data

(60) Provisional application No. 60/603,966, filed on Aug. 23, 2004.

(51) Int. Cl.
*C07H 21/00* (2006.01)
*C07H 21/02* (2006.01)
*C07H 21/04* (2006.01)
*C12Q 1/68* (2006.01)

(52) U.S. Cl. .......................... 536/23.1; 536/25.3; 435/6

(58) Field of Classification Search ................ 536/23.1, 536/25.3; 435/6
See application file for complete search history.

(56) References Cited

U.S. PATENT DOCUMENTS

| | | | |
|---|---|---|---|
| 3,687,808 | A | 8/1972 | Merigan, Jr. et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,500,707 | A | 2/1985 | Caruthers et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,668,777 | A | 5/1987 | Caruthers et al. |
| 4,725,677 | A | 2/1988 | Koster et al. |
| 4,762,779 | A | 8/1988 | Snitman |
| 4,824,974 | A | 4/1989 | Burkhart et al. |
| 4,828,979 | A | 5/1989 | Klevan et al. |
| 4,835,263 | A | 5/1989 | Nguyen et al. |
| 4,845,205 | A | 7/1989 | Huynh Dinh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 4,973,679 | A | 11/1990 | Caruthers et al. |
| 4,978,737 | A | 12/1990 | Vora |
| 4,981,957 | A | 1/1991 | Lebleu et al. |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,124,047 | A | 6/1992 | Quach et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| 5,138,045 | A | 8/1992 | Cook et al. |
| RE34,069 | E | 9/1992 | Koster et al. |
| 5,166,387 | A | 11/1992 | Hirschbein |
| 5,175,273 | A | 12/1992 | Bischofberger et al. |
| 5,214,134 | A | 5/1993 | Weis et al. |
| 5,214,136 | A | 5/1993 | Lin et al. |
| 5,218,105 | A | 6/1993 | Cook et al. |
| 5,245,022 | A | 9/1993 | Weis et al. |
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,272,250 | A | 12/1993 | Spielvogel et al. |
| 5,278,302 | A | 1/1994 | Caruthers et al. |
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,371,241 | A | 12/1994 | Brush |
| 5,391,667 | A | 2/1995 | Dellinger |
| 5,391,723 | A | 2/1995 | Priest |
| 5,393,878 | A | 2/1995 | Leumann |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,446,137 | A | 8/1995 | Maag et al. |
| 5,451,463 | A | 9/1995 | Nelson et al. |
| 5,455,233 | A | 10/1995 | Spielvogel et al. |
| 5,457,187 | A | 10/1995 | Gmeiner et al. |

(Continued)

FOREIGN PATENT DOCUMENTS

EP 216860 4/1987

(Continued)

OTHER PUBLICATIONS

Englisch, U. et al., "Chemically Modified Oligonucleotides as Probes and Inhibitors," Angewandte Chemie (1991) 30(6):613-629.

(Continued)

*Primary Examiner*—Jezia Riley
(74) *Attorney, Agent, or Firm*—Isis Patent Department

(57) ABSTRACT

The present invention relates to oligonucleotide synthesis. In particular, the present invention provides methods for characterizing samples useful for making oligonucleotides.

20 Claims, 14 Drawing Sheets

U.S. PATENT DOCUMENTS

| | | | |
|---|---|---|---|
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,484,908 | A | 1/1996 | Froehler et al. |
| 5,486,603 | A | 1/1996 | Buhr |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,541,313 | A | 7/1996 | Ruth |
| 5,545,730 | A | 8/1996 | Urdea et al. |
| 5,552,538 | A | 9/1996 | Urdea et al. |
| 5,552,540 | A | 9/1996 | Haralambidis |
| 5,565,552 | A | 10/1996 | Magda et al. |
| 5,567,810 | A | 10/1996 | Weis et al. |
| 5,567,811 | A | 10/1996 | Misiura et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,608,046 | A | 3/1997 | Cook et al. |
| 5,610,300 | A | 3/1997 | Altmann et al. |
| 5,617,617 | A | 4/1997 | Gustin |
| 5,627,053 | A | 5/1997 | Usman et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci et al. |
| 5,658,873 | A | 8/1997 | Bertsch-Frank et al. |
| 5,670,633 | A | 9/1997 | Cook et al. |
| 5,681,941 | A | 10/1997 | Cook et al. |
| 5,688,941 | A | 11/1997 | Cook et al. |
| 5,700,920 | A | 12/1997 | Altmann et al. |
| 5,705,621 | A | 1/1998 | Ravikumar |
| 5,750,666 | A | 5/1998 | Caruthers et al. |
| 5,750,692 | A | 5/1998 | Cook et al. |
| 5,763,588 | A | 6/1998 | Matteucci et al. |
| 5,830,653 | A | 11/1998 | Froehler et al. |
| 5,847,106 | A | 12/1998 | Ravikumar et al. |
| 5,889,136 | A | 3/1999 | Scaringe et al. |
| 5,955,600 | A | 9/1999 | Griffey et al. |
| 6,001,982 | A | 12/1999 | Ravikumar et al. |
| 6,005,096 | A | 12/1999 | Matteucci et al. |
| 6,007,992 | A | 12/1999 | Lin et al. |
| 6,008,400 | A | 12/1999 | Scaringe et al. |
| 6,016,895 | A | 1/2000 | Schwuger et al. |
| 6,028,183 | A | 2/2000 | Lin et al. |
| 6,031,092 | A | 2/2000 | Just et al. |
| 6,043,353 | A | 3/2000 | Pon et al. |
| 6,111,086 | A | 8/2000 | Scaringe et al. |
| 6,114,519 | A | 9/2000 | Cole et al. |
| 6,124,450 | A | 9/2000 | Ravikumar et al. |
| 6,133,438 | A | 10/2000 | Cook et al. |
| 6,147,200 | A | 11/2000 | Manoharan et al. |
| 6,160,152 | A | 12/2000 | Capaldi et al. |
| 6,172,209 | B1 | 1/2001 | Manoharan et al. |
| 6,242,591 | B1 | 6/2001 | Cole et al. |
| 6,271,358 | B1 | 8/2001 | Manoharan et al. |
| 6,274,725 | B1 | 8/2001 | Sanghvi et al. |
| 6,300,486 | B1 | 10/2001 | Froehler et al. |
| 6,329,519 | B1 | 12/2001 | Collingwood et al. |
| 6,335,439 | B1 | 1/2002 | Eleuteri et al. |
| 6,465,628 | B1 | 10/2002 | Ravikumar et al. |
| 6,476,216 | B1 | 11/2002 | Just et al. |
| 6,602,833 | B1 * | 8/2003 | Skold ......................... 508/423 |
| 6,627,400 | B1 * | 9/2003 | Singh et al. .................... 435/6 |
| 2003/0158403 | A1 | 8/2003 | Manoharan et al. |

FOREIGN PATENT DOCUMENTS

| | | |
|---|---|---|
| WO | WO 90/02749 | 3/1990 |
| WO | WO 90/15065 | 12/1990 |
| WO | WO 91/08213 | 6/1991 |
| WO | WO 91/15500 | 10/1991 |
| WO | WO 91/018997 | 12/1991 |
| WO | WO 92/005186 | 4/1992 |
| WO | WO 92/019637 | 11/1992 |
| WO | WO 92/20822 | 11/1992 |
| WO | WO 92/20823 | 11/1992 |
| WO | WO 89/12060 | 12/1999 |
| WO | WO 00/008044 | 2/2000 |

OTHER PUBLICATIONS

Flanagan, W. M. et al., "A cytosine analog that confers enhanced potency to antisense oligonucleotides," Proc. Natl. Acad. Sci. USA (1999) 96:3513-3518.

Kroschwitz, J. I. (ed.), "Polynucleotides," The Concise Encyclopedia of Polymer Science and Engineering (1990) Wiley & Sons, New York, pp. 858-859.

Lin, K.-Y. et al., "A Cytosine Analogue Capable of Clamp-Like Binding to a Guanine in Helical Nucleic Acids," J. Am. Chem. Soc. (1998) 120(33):8531-8532.

Sanghvi, Y. S., "Heterocyclic Base Modifications in Nucleic Acids and Their Applications in Antisense Oligonucleotides," Antisense Research and Applications (1993) S. T. Crooke and B. Lebleu (eds.), CRC Press, Boca Raton, pp. 273-288.

Wang, J. et al., "Synthesis and binding property of an oligonucleotide containing tetrafluorophenoxazine," Tetrahedron Letters (1998) 39:8385-8388.

PCT International Search Report for PCT/US05/29850 dated Mar. 21, 2007.

U.S. Appl. No. 10/155,920, filed May 24, 2002, Manoharan et al.

U.S. Appl. No. 10/013,295, filed Dec. 10, 2001, Manoharan et al.

U.S. Appl. No. 09/996,292, filed Nov. 28, 2001, Manoharan et al.

U.S. Appl. No. 09/344,260, filed Jun. 25, 1999, Manoharan et al.

U.S. Appl. No. 09/370,541, filed Aug. 9, 1999, Manoharan et al.

U.S. Appl. No. 08/468,037, filed Jun. 6, 1995, Cook et al.

U.S. Appl. No. 09/349,040, filed Jul. 7, 1999, Manoharan et al.

U.S. Appl. No. 07/990,848, filed Dec. 11, 1992, Sundaramoorthi.

U.S. Appl. No. 07/892,902, filed Jun. 1, 1992, Sundaramoorthi.

U.S. Appl. No. 07/806,710, filed Dec. 12, 1991, Sundaramoorthi.

U.S. Appl. No. 07/763,130, filed Sep. 20, 1991, Matteucci.

U.S. Appl. No. 07/690,786, filed Apr. 24, 1991, Matteucci.

Altmann et al., "Second Generation of Antisense Oligonucleotides: From Nuclease Resistance to Biological Efficacy in Animals," *Chimia* (1996) 50:168-176.

Altmann et al., "Second-generation antisense oligonucleotides: structure-activity relationsgips and the design of improved signal-transduction inhibitors," *Biochem Soc Trans* (1996) 24(3):630-637.

Altmann et al., "Second Generation Antisense Oligonucleotides - Inhibition of PKC-a and c-RAF Kinase Expression by Chimeric Oligonucleotides Incorporating 6'- Substituted Carbocyclic Nucleosides and 2'-O-Ethylene Glycol Substituted Ribonucleosides," *Nucleosides Nucleotides* (1997) 16:917-926.

Alul et al., "Oxalyl-CPG: a labile support for synthesis of sensitive oligonucleotide derivatives," *Nucleic Acids Research* (1991) 19(7):1527-32.

Atherton et al., "Letter: Polyamide supports for polypeptide synthesis," *J Am Chem Soc* (1975) 97(22):6584-6585.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Inititation Complex in Human Umbilical Vein Endothelial Cells," *J Biol Chem* (1997) 272-11944-12000.

Bayer et al., "A new support for polypeptide synthesis in colums," *Tetrahedron Lett* (1970) 51:4503-4505.

Berg et al., "Long-chain polystyrene-grafted polyethylene film matrix: a new support for solid-phase peptide synthesis," *J Am Chem Soc* (1989) 111(20):8024-8026.

Bonora et al., "A Liquid-Phase Process Suitable for Large-Scale Synthesis of Phosphorothioate Oligonucleotides," *Organic Process Research & Development* (2000) 4(3):225-231.

Conte et al., "Conformational Properties and thermodynamics of the RNA duplex r(CGAAAUUUGCG)2: comparison with the DNA analogue d(CGCAAATTTGCG)2," *Nucleic Acids Res* (1997) 25(13):2627-2634.

Coull et al., "Synthesis and characterization of a carbamate-linked oligonucleoside," *Tet Lett* (1987) 28(7):745-748.

Crooke et al., "Pharmacokinetic properties of several novel oligonucleotide analogs in mice," *J Pharmacol Exp Ther* (1996) 277(2):923-937.

Crooke et al., "Progress in antisense therapeutics," *Med Res Rev* (1996) 16(4):319-344.

Daniels et al., "Membranes as solid supports for peptide synthesis," *Tetrahedron Lett* (1989) 30(33):4345-4348.

De Mesmaeker et al., "Antissense Oligonucleotides," *Acc Chem Res* (1995) 28:366-374.

Egli et al., "RNA hydration: a detailed look," *Biochemistry* (1996) 35(26):8489-8494.

Eichler et al., "Application of Cellulose Paper as Support Material in Simultaneous Solid Phase Peptide Synthesis," *Collect. Czech. Chem. Commun.* (1989) 54:1746.

Englisch et al., "Chemically Modified Oligonucleotides as Probes and Inhibitors," *Angewandte Chemie*, 30:613, International Edition (1991).

Fedoroff et al., "Structure of a DNA:RNA hybrid duplex. Why RNase H does not cleave pure RNA," *J Mol Biol* (1993) 233(3):509-523.

Freier et al., "The ups and Downs of nucleic acid duplex stability: structure-stability studies on chemically-modified DNA:RNA duplexes," *Nucleic Acids Res* (1997) 25(22):4429-4443.

Geysen et al., "Use of peptide synthesis to probe viral antigens for epitopes to a resolution of a single amino acid," *Proc Natl Acad Sci USA* (1984) 81:3998-4002.

Gonzalez et al., "Structure and dynamics of a DNA.RNA hybrid duplex with a chiral phosphorothioate moiety: NMR and molecular dynamics with convential and time-averaged restraints," *Biochemistry* (1995) 34(15):4969-4982.

Gorman "An apparatus for simultaneous manual solid-phase synthesis of multiple peptide analogs," *Anal. Biochem* (1984) 136(2):397-406.

Gravert et al., "Organic Synthesis on Soluble Polymer Supports: Liquid-Phase Methodologies," *Chem Rev* (1997) 97(2):489-510.

Hewitt et al., "Structural Determination of Silicon-Containing Oligonucleotides by 1H-29Si Long-Range Heteronuclear Multiple Quantum Correlation NMR Spectroscopy," *Nucleosides & Nucleotides* (1992) 11:1661-1666.

Horton et al., "The structure of an RNA/DNA hybrid: a substrate of the ribonuclease activity of HIV-1 reverse transcriptase," *J Mol Biol.* (1996) 264(3):521-533.

Houghten,"General method for the rapid solid-phase synthesis of large numbers of peptides: specificity of antigen-antibody interaction at the level of individual amino acids," *Proc Natl Acad Sci USA* (1985) 82(15):5131-5135.

Kabanov et al., "A new class of antivirals: antisense oligonucleotides combined with a hydrophobic substituent effectively inhibit influenza virus reproduction and synthesis of virus-specific proteins in MDCK cells," *FEBS Lett* (1990) 259(2):327-330.

Kent et al., "Preparation and Properties of tert-Butyloxycarbonylaminoacyl-4- (oxymethyl) phenulacetamidomethyl-(Kel F-g-styrene) Resin, an Insoluble, Noncrosslinked Support for Solid Phase Peptide Synthesis," *Israel J Chem* (1978) 17:243.

Krchnak et al., "Multiple continuous-flow solid-phase peptide synthesis. Synthesis of an HIV antigenic peptide and its omission analogues," *Int J Peptide Protein Res* (1989) 33(3):209-213.

Kurchavov et al., "A New Phodphoramidite Reagent for the Incorporation of Diazaphenoxazinone Nucleoside with Enhanced Base-Pairing Properties in Oligodeoxynucleotides," *Nucleosides and Nucleotides* (1997) 16:1837-1846.

Lane et al., "NMR assignments and solution conformation of the DNA.RNA hybrid duplex d(GTGAACTIT).r(AAGUUCAC)," *Eur J Biochem* (1993) 215(2):297-306.

Lebl et al., "Simulation of Continuous Solid Phase Synthesis: Synthesis of Methionine Enkephalin and its Analogs," *Peptide Res* (1989) 2:232.

Lesnik et al., "Relative thermodynamic stability of DNA, RNA, and DNA:RNA hybrid duplexes: relationship with base composition and structure," *Biochemistry* (1995) 34(34):1087-10815.

Letsinger et al., "Cholesteryl-conjugated oligonucleotides: synthesis, properties, and activity as inhibitors of replication of human immunodeficiency virus in cell culture," *Proc Natl Acad Sci USA* (1989) 86(17):6553-6556.

Lin et al., "Tricyclic 2'-Deoxycytidine Analogs: Syntheses and Incorporation into Oligodeoxynucleotides which have Enhanced Binding to Complementary RNA," *M. J. Am. Chem. Soc.* (1995) 117:3843-3874.

Manoharan et al., "Cholic Acid-Oligonucleotide Conjugates for Antisense Applications," *Bioorg Med Chem Lett* (1994) 4:1053.

Manoharan et al., "Chemical modifications to improve uptake and bioavailability of antisense oligonucleotides," *Ann NY Acad Sci* (1992) 660:306-309.

Manoharan et al., "Introduction of a Lipophilic Thioether Tether in the Minor Groove of Nucleic Acids for Antisense Applications," *Bioorg Med Chem Lett* (1993) 3:2765.

Manoharan et al., "Lipidic Nucleic Acids," *Tetrahedron Lett* (1995) 36:3651.

Manoharan et al., "Oligonucleotide Conjugates: Alteration of the Pharmacokinetic Properties of Antisense Agents," *Nucleosides & Nucleotides* (1995) 14:969.

Martin et al., "Ein Neuer Zugang zu 2'-O-Alkylribonucleosiden und Eigenshaften deren Oligonucleotide," *Helv Chim Acta* (1995) 78:486-504.

Mertes et al., "Synthesis of carbonate analogs of dinucleosides. 3'-Thymidinyl 5'- thymidinyl carbonate, 3'-thymidinyl 5'-(5-fluoro-2'-deoxyuridinyl) carbonate, and 3'-(5- fluoro-2'-deoxyuridinyl) 5'-thymidinyl carbonate," *J Med Chem* (1969) 12(1):154-157.

Mishara et al., "Improved leishmanicidal effect of phosphorotiotate antisense oligonucleotides by LDL-mediated delivery," *Biochim Biophys Acta* (1995) 1264(2):229-237.

Mungall et al., "Carbamate analogues of oligonucleotides," *J Org Chem* (1977) 42(4):703-706.

Musicki et al., "Synthesis of Carbohydrate Sulfonates and Sulfonate Esters," *J Org Chem* (1990) 55:4231-4233.

Oberhauser et al., "Effective incorporation of 2'-O-methyl-oligoribonucleotides into liposomes and enhanced cell association through modification with thiocholesterol," *Nucl Acids Res* (1992) 20(3):533-538.

Parr et al., *Angew Chem Internal Ed*, 11:314, Waters Associates, Framingham, Mass, USA (1972).

Reynolds et al., "Synthesis of Thymidine Dimers Containing Internucleoside Sulfonate and Sulfonamide Limkages," *J Org Chem* (1992) 57:2983-2985.

Saison-Behmoaras et al., "Short Modified Antisense Oligonucleotides directed against Ha-ras point mutation include selective cleavage of the mRNA and inhibit T24 cell proliferation," *EMBO J* (1991) 10:111.

Sanghvi, *Antisense Research and Applications*, Ch. 15, pp. 289-302, CRC Press (1993).

Scott et al., "The Use of Resin Coated Glass Beads in the Form of a Packed Bed for the Solid Phase Synthesis of Peptides," *J Chrom Sci* (1971) 9:577.

Searle et al., "On the stability of nucleic acid structures in solution: enthalpy-entropy compensations, internal rotations and reversibility," *Nucleic Acids Res*. (1993) 21(9):2051-2056.

Shea et al., "Synthesis, hybridization properties and antiviral activity of lipid-oligodeoxynucleotide conjugates," *Nucl Acids Res* (1990) 18(13):3773-3783.

Singh et al., "LNA (locked nucleic acids):synthesis and high-affinity nucleic acid recognition," *Chem Commun* (1998) 4:455-456.

Sood et al., "Boron-Containing Nucleic Acids. 2.1 Synthesis of Oligodeoxynucleoside Boranophosphates," *J Am Chem Soc* (1990) 112:9000-9001.

Stirchak et al., "Uncharged stereoregular nucleic acid analogs: 2. Morpholino nucleoside oligomers with carbamite internucleoside linkages," *Nuclei Acid Res* (1989) 17(15):6129-6141.

Stirchak et al., "Uncharged Stereoregular Nucleic Acid Analogues. 1. Synthesis of a Cytosine-Containing Oligomer with Carbamate Internucleoside Linkages," *J Org Chem* (1987) 52:4202-4206.

Svinarchuk et al., "Inhibition of HIV proliferation in MT-4 cells by antisense oligonucleotide conjugated to lipophilic groups," *Biochimie* (1993) 75(1-2):49-54/

Tregear, *Chemistry and Biology of Peptides*, J. Meienhofer, ed., Ann Arbor Sci. Publ., Ann Arbor, 1972, pp. 175-178.

Van Rietschoten "Simultaneous Synthesis of Two Peptide Analogs on Different Insoluble Supports," *Peptides* (1975) 13: 113-116.

Vasseur et al., "Oligonucleosides: Synthesis of a Novel Methylhydroxylamine-Linked Nucleoside Dimer and It's Incorporation into Antisense Sequence," *J Amer Chem Soc* (1992) 114:4006-4007.

Wang et al., "Solid Phase Synthesis of Neutral Oligonucleotide Analogues," *Tetrahedron Lett* (1991) 32:7385-7388.

Wright et al., "Large Scale Synthesis of Oligonucleotides via Phosphoramidite Nucleosides and a High-loaded Polystryrene Support," *Tetrahedron Letters* (1993) 34:3373.

* cited by examiner

The average mass spectrum of the main UV peak obtained by ion pair-liquid chromatography analysis of a typical batch of ISIS 3521 drug substance Ion chromatograms of full-length, fully-thioated species and m/z =1644.4 impurity in a) control sample, b) sample spiked with 0.5% of 5

Ion pair-liquid chromatogram of ISIS 3521 drug substance

Average mass spectrum of RRT = 1.3 impurity

IP-LC-UV chromatogram of d(CpA) P=S

Average mass spectrum of late-eluting peaks in d(CpA) P=S

UV chromatograms of a) d(CpA) P=S, b) 3, c) 4,d) d(CpA) P=S + 3, e) d(CpA) P=S + 4

Average mass spectrum of trimer 4 (late eluting peaks)

IP-LC-MS analysis of 1.

Panel a) UV Chromatogram, b) average mass spectrum of main peak

IP-LC-MS analysis of 2.

Panel a) UV chromatogram, b) average mass spectrum of main peak

IP-LC-UV analysis of a) ISIS 3521 drug substance,
b) ISIS 3521 drug substance spiked with 1% of 1,
c) ISIS 3521 drug substance spiked with 1% of 2 and
d) 1:1 mixture of 1 and 2.

UV chromatograms of the control and X twelve-mer

UV chromatogram of impurity XI twelve-mer

UV chromatogram of the XVIII synthesis

COMPOUNDS AND METHODS FOR THE CHARACTERIZATION OF OLIGONUCLEOTIDES

CROSS REFERENCE TO RELATED APPLICATIONS

This application claims priority benefit of U.S. Provisional Application Ser. No. 60/603,966, filed Aug. 23, 2004, the entire disclosure of which is incorporated by reference herein.

FIELD OF THE INVENTION

The present invention relates to methods of characterizing samples containing oligomeric compounds, including oligonucleotides synthesis. The invention further provides compounds and synthetic methods useful for the same.

BACKGROUND OF THE INVENTION

Oligonucleotides have been used in various biological and biochemical applications. They have been used as primers and probes for the polymerase chain reaction (PCR), as antisense agents used in target validation, drug discovery and development, as ribozymes, as aptamers, and as general stimulators of the immune system. As the popularity of oligonucleotides has increased, the need for producing greater sized batches, and greater numbers of small-sized batches, has increased at pace. Additionally, there has been an increasing emphasis on reducing the costs of oligonucleotide synthesis, and on improving the purity and increasing the yield of oligonucleotide products.

A number of innovations have been introduced to the art of oligonucleotide synthesis. Amongst these innovations have been the development of excellent orthogonal protecting groups, activators, reagents, and synthetic conditions. The oligonucleotides themselves have been subject to a variety of modifications and improvements. Amongst these are chemistries that improve the affinity of an oligonucleotide for a specific target, that improve the stability of an oligonucleotide in vivo, that enhance the pharmacokinetic (PK) and toxicological (Tox) properties of an oligonucleotide, etc. These novel chemistries generally involve a chemical modification to one or more of the constituent parts of the oligonucleotide.

The term "oligonucleotide" thus embraces a class of compounds that include naturally-occurring, as well as modified, oligonucleotides. Both naturally-occurring and modified oligonucleotides have proven useful in a variety of settings, and both may be made by similar processes, with appropriate modifications made to account for the specific modifications adopted. A naturally occurring oligonucleotide, i.e. a short strand of DNA or RNA may be envisioned as being a member of the following generic formulas, denominated oligo-RNA and oligo-DNA, respectively, below:

Naturally-Occurring Oligonucleotides

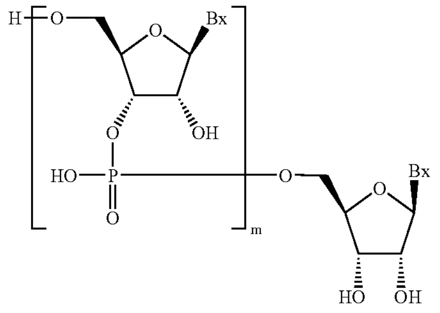

oligo-RNA

-continued

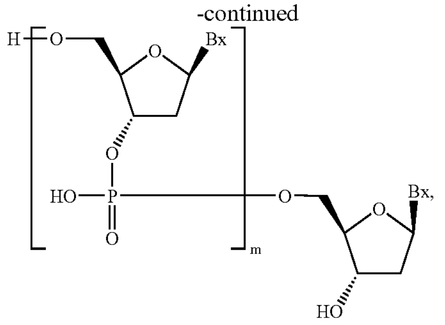

oligo-DNA wherein m is an integer of from 1 to about 100, and Bx is one of the naturally occurring nucleobases.

Physiologic pH, an oligonucleotide occurs as the anion, as the phosphate easily dissociates at neutral pH, and an oligonucleotide will generally occur in solid phase, whether amorphous or crystalline, as a salt. Thus, unless otherwise modified, the term "oligonucleotide" encompasses each of the anionic, salt and free acid forms above.

In essence, a naturally occurring oligonucleotide may be thought of as being an oligomer of m monomeric subunits represented by the following nucleotides:

Naturally-Occurring Nucleotide Monomers

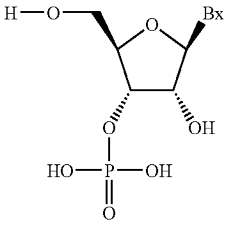

ribonucleotide

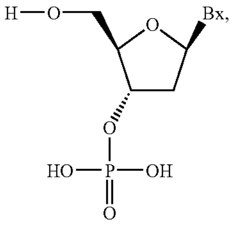

deoxyribonucleotide wherein each Bx is a nucleobase, wherein the last residue is a nucleoside (i.e. a nucleotide without the 3'-phosphate group).

As mentioned above, various chemistry modifications have been made to oligonucleotides, in order to improve their affinity, stability, PK, Tox, and other properties. In general, the term oligonucleotide, as now used in the art, encompasses inter alia compounds of the formula:

Oligonucletoides (General)

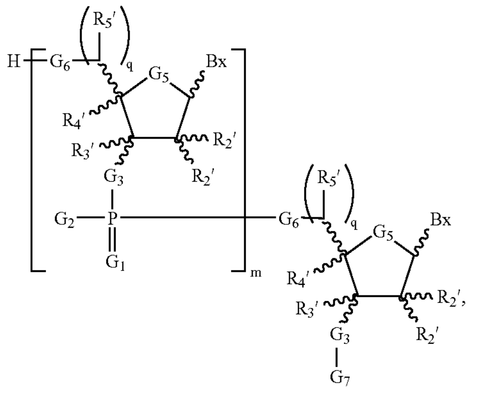

wherein m is an integer from 1 to about 100, each $G_1$ is O or S, each $G_2$ is OH or SH, each $G_3$ is O, S, $CH_2$, or NH, each $G_5$ is a divalent moiety such as O, S, $CH_2$, CFH, $CF_2$, —CH═CH—, etc., each $R_2'$ is H, OH, O-rg, wherein rg is a removable protecting group, a 2'-substituent, or together with $R_4'$ forms a bridge, each $R_3'$ is H, a substituent, or together with $R_4'$ forms a bridge, each $R_4'$ is H, a substitutent, together with $R_2'$ forms a bridge, together with $R_3'$ forms a bridge, or together with $R_5'$ forms a bridge, each q is 0 or 1, each $R_5'$ is H, a substituent, or together with $R_4'$ forms a bridge, each $G_6$ is O, S, $CH_2$ or NH, each $G_7$ is H, $PO_3H_2$, or a conjugate group, and each Bx is a protected or unprotected, naturally occurring or non-naturally occurring nucleobase, as described herein (i.e. naturally occurring or modified).

The standard synthetic methods for oligonucleotides include the solid phase methods first described by Caruthers et al. (See, for example, U.S. Pat. No. 5,750,666, incorporated herein by reference, especially columns 3-58, wherein starting materials and general methods of making oligonucleotides, and especially phosphorothioate oligonucleotides, are disclosed, which parts are specifically incorporated herein by reference.) These methods were later improved upon by Köster et al. (See, for example, U.S. Pat. No. RE 34,069, which is incorporated herein by reference, especially columns, wherein are disclosed, which parts are specifically incorporated herein by reference.) These methods have further been improved upon by various inventors, as discussed in more detail below. Methods of synthesizing RNA are disclosed in, inter alia, U.S. Pat. Nos. 6,111,086, 6,008,400, and 5,889,136, each of which is incorporated herein in its entirety. Especially relevant are columns 7-20 of U.S. Pat. No. 6,008,400, which are expressly incorporated herein by reference.

The general process for manufacture of an oligonucleotide by the Köster et al. method may be described as follows:

First, a primer support is prepared by covalently linking a suitable nucleoside to a support (SS) through a linker. Such a primer support is as follows:

Primer Support (General)

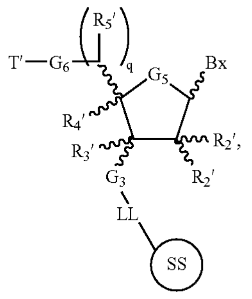

wherein SS is the support, LL is a linking group that links the nucleoside to the support via $G_3$. The linking group is generally a di-functional group, covalently binds the ultimate 3'-nucleoside (and thus the nascent oligonucleotide) to the solid support during synthesis, but which is cleaved under conditions orthogonal to the conditions under which the 5'-protecting group, and if applicable any 2'-protecting group, are removed. T' is a removable protecting group, and the remaining variables have already been defined, and are described in more detail herein. Suitable primer supports may be acquired from Amersham Biosciences under the brand name Primer Support 200™. The primer support may then be swelled in a suitable solvent, e.g. acetonitrile, and introduced into a column of a suitable solid phase synthesis instrument, such as one of the synthesizers available form Amersham Biosciences, such as an ÄKTAoligopilot™, or OligoProcess™ brand DNA/RNA synthesizer.

Synthesis is carried out from 3'- to 5'-end of the oligomer. In each cycle, the following steps are carried out: (1) removal of T', (2) coupling, (3) oxidation, (4) capping. Each of the steps (1)-(4) may be, and generally is, followed by one or more wash steps, whereby a clean solvent is introduced to the column to wash soluble materials from the column, push reagents and/or activators through the column, or both. The steps (1)-(4) are depicted below:

Oligo Synthesis Cycle -- Step 1

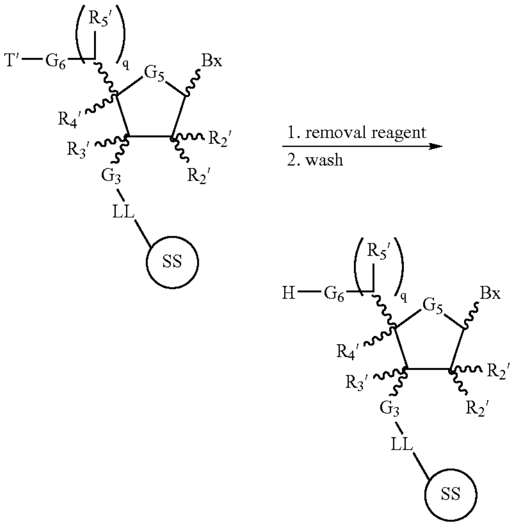

In general, T' is selected to be removable under conditions orthogonal to those used to cleave the oligonucleotide from the solid support at the end of synthesis, as well as those used to remove other protecting groups used during synthesis. An art-recognized protecting group for oligonucleotide synthesis is DMT (4,4'-dimethoxytrityl). The DMT group is especially useful as it is removable under weakly acid conditions. Thus, an acceptable removal reagent is 3% DCA in a suitable solvent, such as acetonitrile. The wash solvent, if used, may conveniently be acetonitrile.

The support may be controlled pore glass or a polymeric bead support. Some polymeric supports are disclosed in the following patents: U.S. Pat. Nos. 6,016,895; 6,043,353; 5,391,667 and 6,300,486, each of which is specifically incorporated herein by reference.

Oligo Synthesis Cycle -- Step 2

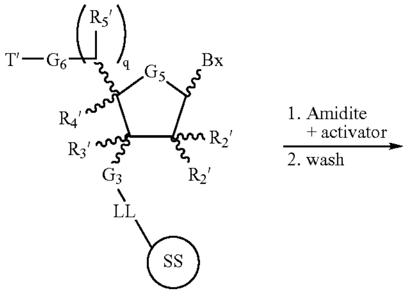

-continued

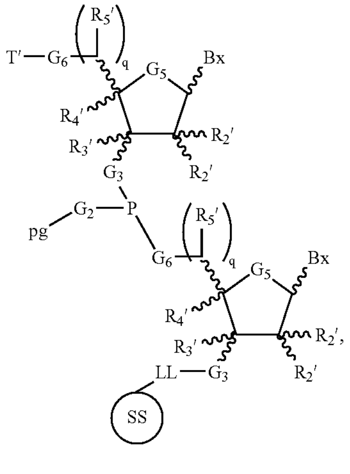

wherein pg is a phosphorus protecting group, such as a cyanoethyl group. See, Köster et al., supra, for information on manufacturing of the amidite:

Amidite (General)

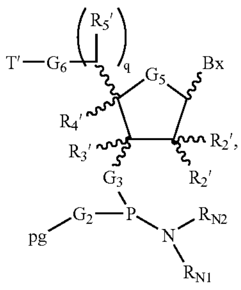

wherein $NR_{N1}R_{N2}$ is an amine leaving group, such as diisopropyl amino, and for teaching of suitable activator (e.g. tetrazole). Other suitable amidites, and methods of manufacturing amidites, are set forth in the following patents: U.S. Pat. Nos. 6,133,438; 5,646,265; 6,124,450; 5,847,106; 6,001, 982; 5,705,621; 5,955,600; 6,160,152; 6,335,439; 6,274,725; 6,329,519, each of which is specifically incorporated herein by reference, especially as they relate to manufacture of amidites. Suitable activators are set forth in the Caruther et al. patent and in the Köster et al. patent. Especially suitable activators are set forth in the following patents: U.S. Pat. Nos. 6,031,092 and 6,476,216, each of which is expressly incorporated herein by reference.

The next step of the synthesis cycle is oxidation, which indicates that the P(III) species is oxidized to a P(V) oxidation state with a suitable oxidant:

Oligo Synthesis Cycle—Step 3

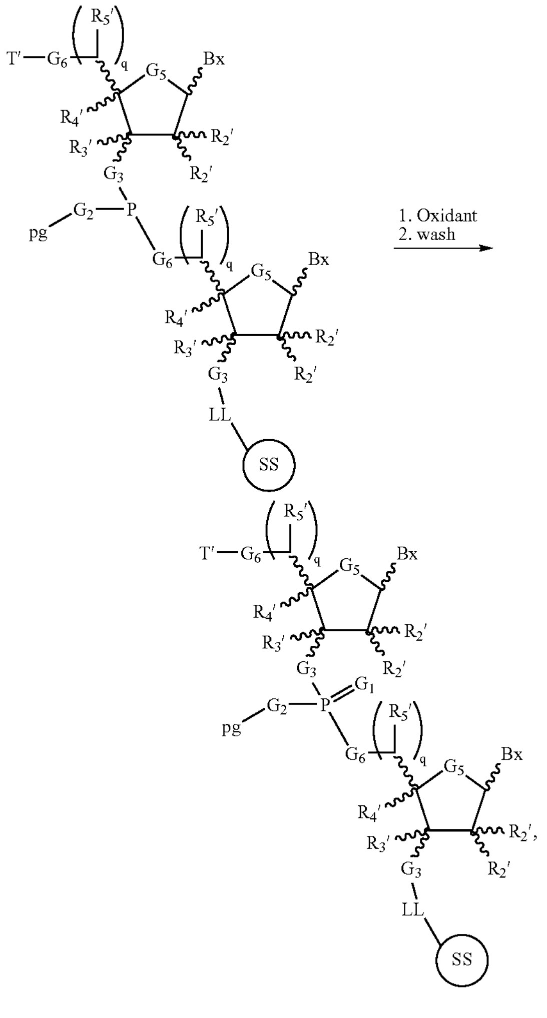

wherein $G_1$ is O or S.

The oxidant is an oxidizing agent suitable for introducing $G_1$. In the case where $G_1$ is oxygen, a suitable oxidant is set forth in the Caruthers et al. patent, above. In cases where $G_2$ is sulfur, the oxidant may also be referred to as a thiation agent or a sulfur-transfer reagent. Suitable thiation agents include the so-called Beaucage reagent, 3H-1,2-benzothiol, phenyacetyl disulfide (also referred to as PADS; see, for example the patents: U.S. Pat. Nos. 6,114,519 and 6,242,591, each of which is incorporated herein by reference) and thiouram disulfides (e.g. N,N,N',N'-tetramethylthiouram disulfide, disclosed by U.S. Pat. No. 5,166,387). The wash may be a suitable solvent, such as acetonitrile.

The oxidation step is followed by a capping step, which although not illustrated herein, is an important step for synthesis, as it causes free 5'-OH groups, which did not undergo coupling in step 1, to be blocked from being coupled in subsequent synthetic cycles. Suitable capping reagents are set forth in Caruthers et al., Köster et al., and other patents described herein. Suitable capping reagents include a combination of acetic anhydride and N-methylimidazole.

Synthetic cycle steps (1)-(4) are repeated (if so desired) n−1 times to produce a support-bound oligonucleotide:

Support-Bound Oligonucleotide

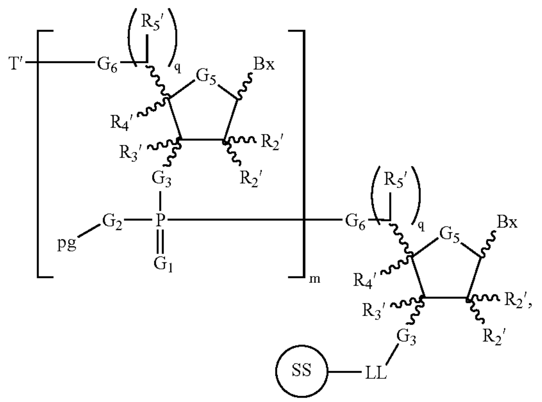

wherein each of the variables is as herein defined.

In general, the protecting group pg may be removed by a method as described by Caruthers et al. or Köster et al., supra. Where pg is a cyanoethyl group, the methodology of Köster et al., e.g. reaction with a basic solution, is generally suitable for removal of the phosphorus protecting group. In some cases it is desirable to avoid formation of adducts such as the N1-cyanoethyl thymidine group. In these cases, it is desirable to include in the reagent a tertiary amine, such as triethylamine (TEA) as taught in U.S. Pat. No. 6,465,628, which is expressly incorporated herein by reference. In general, where the nucleobases are protected, they are deprotected under basic conditions. The deprotected oligonucleotide is cleaved from the support to give the following 5'-protected oligonucleotide:

Free 5'-Protected Oligonucleotide

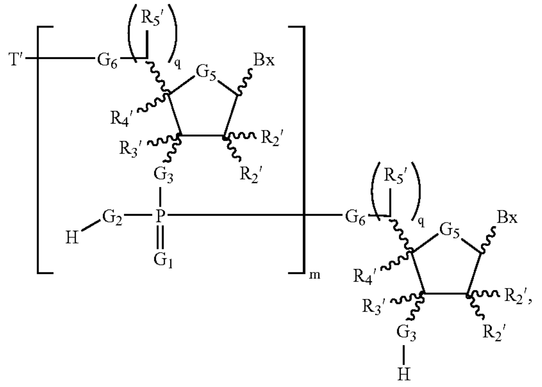

which may then be purified by reverse phase liquid chromatography, deprotected at the 5'-end in acetic acid, desalted, lyophilized or otherwise dried, and stored in an inert atmosphere until needed. Optionally, the $G_3H$ group may be derivatized with a conjugate group. The resulting oligonucleotide may be visualized as having the formula:

Oligonucleotide

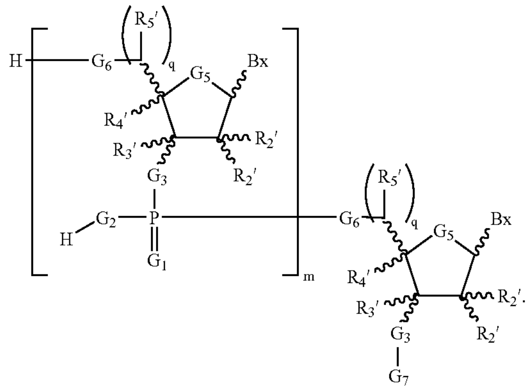

While many improvements have been made in the quality and costs of oligonucleotide synthesis, there still remain a number of improvements to be made. For instance, the purity of amidite starting material (phosphoramidites) is a limiting factor, not only in oligonucleotide product purity, but also overall yield, and potentially biological efficacy and or toxicity. Accordingly, it is essential to obtain amidite starting material that will provide as pure an oligonucleotide as possible. While strides have been made in providing purified amidites, there remain problems associated with providing amidite starting material that is suitable for oligonucleotide synthesis.

One such problem is that, as amidite purity increases, so does its cost. It is possible, in theory, to produce an amidite of purity approaching 100%. However, as purity asymptotically approaches 100%, the associated costs of purification also escalate. Indeed, two factors cause those costs to escalate well out of proportion to the gains in amidite purity. One factor is that, as purity increases, the amount of effort needed to extract an additional fractional percentage of impurity increases. A second factor is that with each stage of purification, there will be loss of amidite product. These two factors result in a cost-benefit curve that favors some optimum purity somewhat short of 100%. Nonetheless, it is still theoretically desirable to use the absolute highest purity amidite starting material to produce oligonucleotides.

There is thus a need for a method of obtaining and characterizing amidite starting materials that are of purity suitable for oligonucleotide synthesis, while taking into account the increasing cost of each added degree of purification.

SUMMARY OF THE INVENTION

In some embodiments, the present invention provides compounds having the structure of Formula I:

I

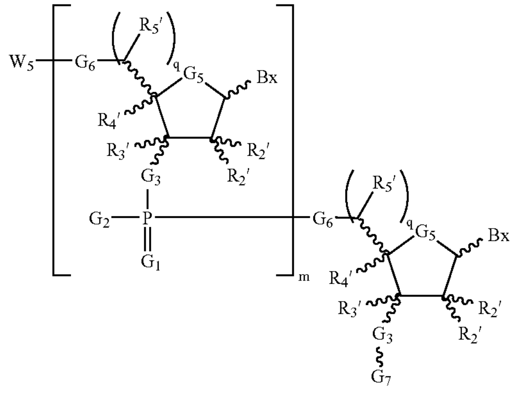

wherein:

$W_5$ is H, a capping group, or a protecting group;

m is an integer from 1 to about 100;

each $G_1$ is O or S;

each $G_2$ is OH or SH;

each $G_3$ is O, S, $CH_2$, or NH;

each $G_5$ is O, S, $CH_2$, CFH, $CF_2$, or —CH═CH—;

each $R_2'$ is H, OH, O-rg, wherein rg is a removable protecting group, a 2'-substituent, or together with $R_4'$ forms a bridge;

each $R_3'$ is H, a substituent, or together with $R_4'$ forms a bridge;

each $R_4'$ is H, a substituent, or together with $R_2'$ forms a bridge, together with $R_{3'}$ forms a bridge, or together with $R_5'$ forms a bridge;

each q is 0 or 1;

each $R_5'$ is H, a substituent, or together with $R_4'$ forms a bridge;

each $G_6$ is O, S, $CH_2$ or NH;

each $G_7$ is H, $PO_3H_2$, or a conjugate group; and each Bx is a naturally occurring or modified nucleobase;

provided that at least one Bx has one of the structures Bm, Bn or Bo:

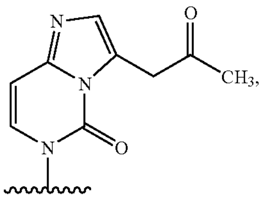

Bm

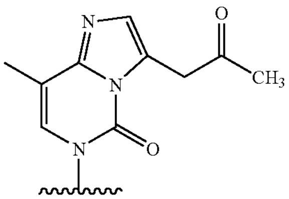

or

Bn

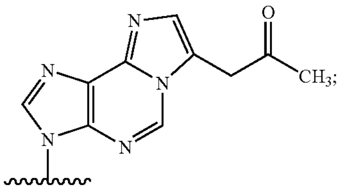

Bo

In further embodiments, the present invention provides compounds as describe above, having the formula:

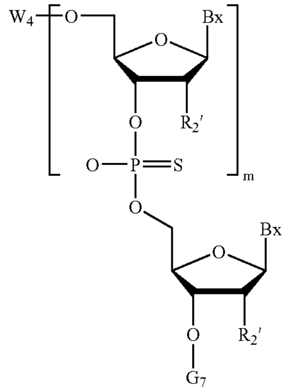

wherein:

$W_4$ is H, a protecting group, or an internucleoside linkage optionally connected to an oligonucleotide In further embodiments, the present invention provides compounds having the structure of Formula II:

II

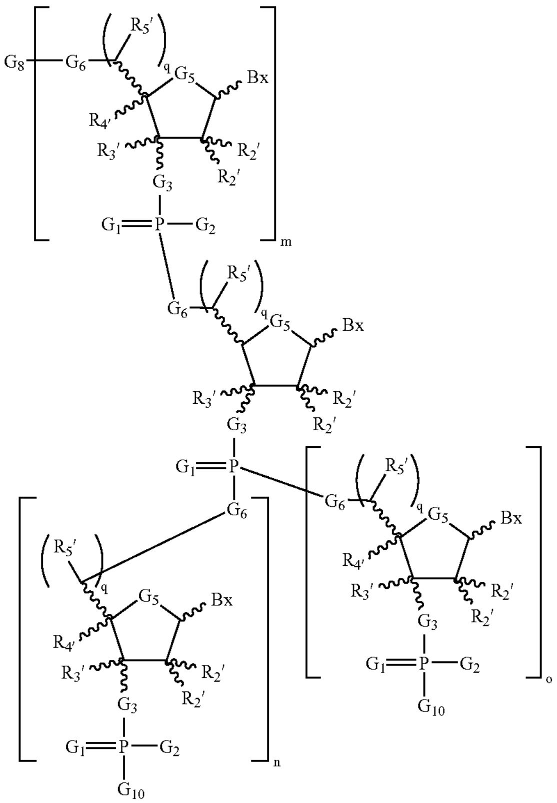

wherein:

each $G_1$ is O or S;

each $G_2$ is OH or SH;

each $G_3$ is O, S, $CH_2$, or NH;

each $G_5$ is O, S, $CH_2$, CFH, $CF_2$, or —CH═CH—;

each $R_2'$ is H, OH, O-rg, wherein rg is a removable protecting group, a 2'-substituent, or together with $R_4'$ forms a bridge;

each $R_3'$ is H, a substituent, or together with $R_4'$ forms a bridge;

each $R_4'$ is H, a substituent, or together with $R_2'$ forms a bridge, together with $R_{3'}$ forms a bridge, or together with $R_5'$ forms a bridge;

each q is 0 or 1;

each $R_5'$ is H, a substituent, or together with $R_4'$ forms a bridge;

each $G_6$ is O, S, $CH_2$ or NH;

$G_8$ is H or a protecting group;

$G_{10}$ is OH, O-Pg, a nucleoside, a nucleotide, or a nucleoside linked to a solid support or to a conjugate group;

Pg is a protecting group;

m is an integer from 1 to about 100;

n and o are each identical integers from 0 to about 100, provided that when n and o are 0, then each $G_{10}$ is an independently selected nucleoside linked to a solid support; and each Bx is a naturally occurring or modified nucleobase;

In further embodiments, the present invention provides compounds having the formula:

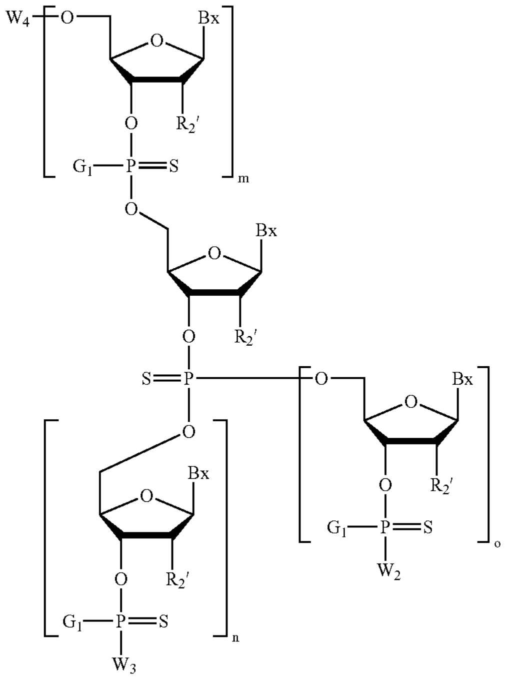

wherein:

m is an integer from 1 to about 100;

n and o are each identical integers from 0 to about 100, provided that when n and o are 0, then $W_2$ and $W_3$ are each an independently selected nucleoside linked to a solid support;

each $G_1$ is OH or SH;

each $R_2$, is independently selected from the group consisting of H, OH, O-Pg and an independently selected 2'-substituent;

$W_2$ and $W_3$ are each independently OH, O-Pg, a nucleoside, a nucleotide, or a nucleoside linked to a solid support or to a conjugate group;

Pg is a protecting group; and $W_4$ is H, a capping group, or a protecting group, a nucleotide or an oligonucleotides;

In some embodiments, the present invention provides methods of characterizing a sample comprising one or more oligomers and at least one impurity, the method comprising:

providing said sample comprising one or more oligomers and at least one impurity;

obtaining an impurity sample signal from said impurity in said sample;

comparing the impurity sample signal with a standard signal to determine the amount of said impurity in said sample; and either rejecting said sample if the amount of the impurity is greater than a predetermined critical impurity threshold, or accepting said sample if the amount of the impurity is less than or equal to said predetermined impurity threshold;

wherein said impurity has the formula I:

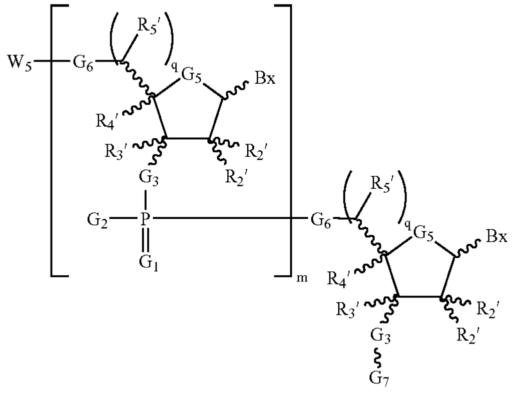

wherein:

$W_5$ is H, a capping group, or a protecting group;

m is an integer from 1 to about 100;

each $G_1$ is O or S;

each $G_2$ is OH or SH;

each $G_3$ is O, S, $CH_2$, or NH;

each $G_5$ is O, S, $CH_2$, CFH, $CF_2$, or —CH═CH—;

each $R_2'$ is H, OH, O-rg, wherein rg is a removable protecting group, a 2'-substituent, or together with $R_4'$ forms a bridge;

each $R_3'$ is H, a substituent, or together with $R_4'$ forms a bridge;

each $R_4'$ is H, a substituent, or together with $R_2'$ forms a bridge, together with $R_{3'}$ forms a bridge, or together with $R_5'$ forms a bridge;

each q is 0 or 1;

each $R_5'$ is H, a substituent, or together with $R_4'$ forms a bridge;

each $G_6$ is O, S, $CH_2$ or NH;

each $G_7$ is H, $PO_3H_2$, or a conjugate group; and each Bx is a naturally occurring or modified nucleobase;

wherein at least one Bx has one of the structures Bm, Bn or Bo:

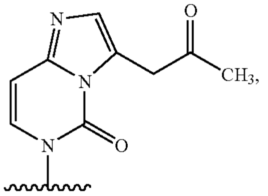

Bm

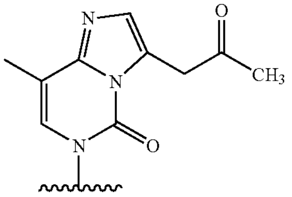

or

Bn

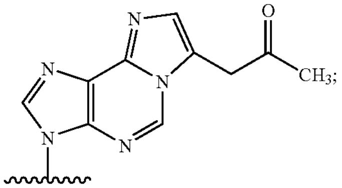

Bo wherein either:

i) said standard signal is obtained from an internal standard in said determination having said formula I; or ii) said standard signal is a property of said impurity.

In some embodiments, said impurity has the formula:

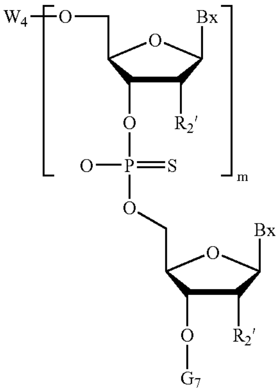

wherein $W_4$ is H, a capping group, or a protecting group.

In some embodiments, the present invention provides methods of characterizing an sample comprising one or more oligomers and at least one impurity, the method comprising:

providing said sample comprising one or more oligomers and at least one impurity;

obtaining an impurity sample signal from said impurity in said sample;

comparing the impurity sample signal with a standard signal to determine the amount of said impurity in said sample; and either rejecting said sample if the amount of the impurity is greater than a predetermined critical impurity threshold, or accepting said sample if the amount of the impurity is less than or equal to said predetermined impurity threshold;

wherein said impurity has the Formula II:

II

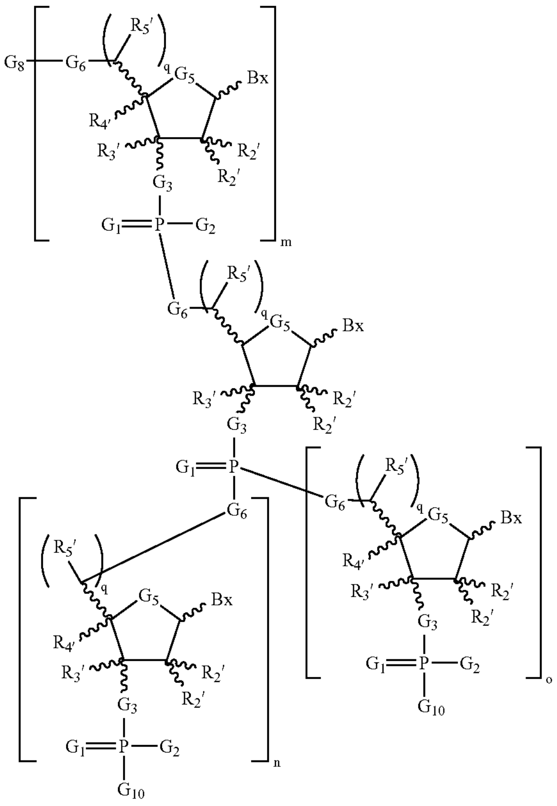

wherein:

each $G_1$ is O or S;

where pg is a protecting group, each $G_2$ is OH or SH;

each $G_3$ is O, S, $CH_2$, or NH;

each $G_5$ is O, S, $CH_2$, CFH, $CF_2$, or —CH═CH—;

each $R_2$' is H, OH, O-rg, wherein rg is a removable protecting group, a 2'-substituent, or together with $R_4$' forms a bridge;

each $R_3$' is H, a substituent, or together with $R_4$' forms a bridge;

each $R_4$' is H, a substituent, or together with $R_2$' forms a bridge, together with $R_{3'}$ forms a bridge, or together with $R_5$' forms a bridge;

each q is 0 or 1;

each $R_5$' is H, a substituent, or together with $R_4$' forms a bridge;

each $G_6$ is O, S, $CH_2$ or NH;

$G_8$ is H or a protecting group;

$G_{10}$ is OH, O-Pg, a nucleoside, a nucleotide, or a nucleoside linked to a solid support or to a conjugate group;

Pg is a protecting group;

m is an integer from 1 to about 100;

n and o are each identical integers from 0 to about 100, provided that when n and o are 0, then each $G_{10}$ is an independently selected nucleoside linked to a solid support; and each Bx is a naturally occurring or modified nucleobase;

wherein either:

i) said standard signal is obtained from an internal standard in said determination having said formula II; or ii) said standard signal is a property of said impurity.

In some such embodiments, the impurity has the formula:

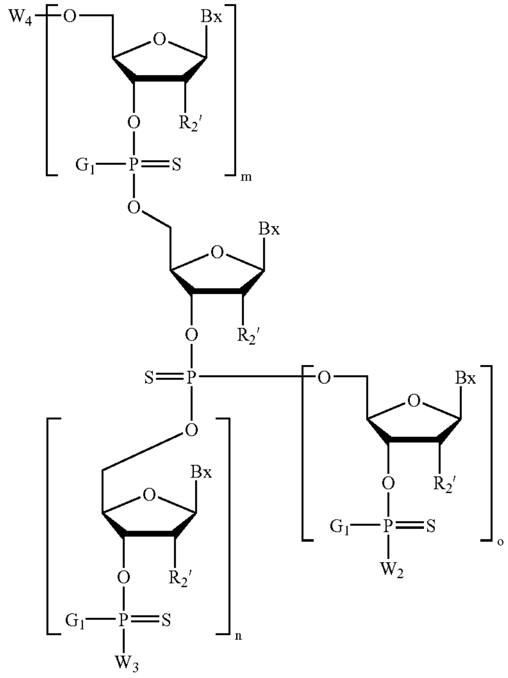

wherein:

m is an integer from 1 to about 100;

n and o are each identical integers from 0 to about 100, provided that when n and o are 0, then $W_2$ and $W_3$ are each an independently selected nucleoside linked to a solid support;

each $G_1$ is OH or SH;

each $R_{2'}$ is independently selected from the group consisting of H and an independently selected 2'-substituent;

$W_2$ and $W_3$ are each independently OH, O-Pg, a nucleoside, a nucleotide, or a nucleoside linked to a solid support or to a conjugate group;

Pg is a protecting group; and $W_4$ is H, a capping group, or a protecting group, a nucleotide or an oligonucleotide.

In some embodiments, the present invention provides methods for synthesizing a nucleosidic compound bearing a nucleobase of formula IV, V or VI:

IV

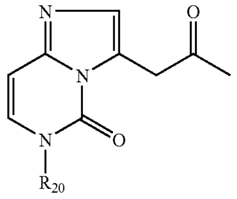

or

-continued

V

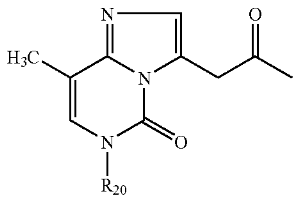

or

VI

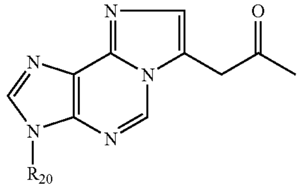

wherein $R_{20}$ is an optionally protected nucleoside sugar, or an optionally protected nucleoside phosphoramidite; the method comprising:

a) reacting a compound of formula:

VII

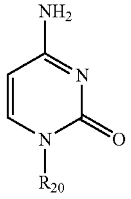

or

VIII

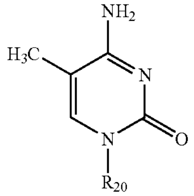

or

IX

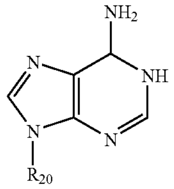

with a 4-oxo-2-pentenal under conditions of effective to form said compound. In some embodiments, the methods wherein the compound of formula of formula VII, VIII or IX that is reacted with the 4-oxo-2-pentenal is a nucleoside; the method further comprises:

b) protecting the 3'-hydroxyl of the product of step (a) with a protecting group suitable for oligonuclotide synthesis;

c) reacting the protected nucleoside from step (b) with a reagent effective to transform the 3'-hydroxyl thereof to a group of formula —O—P($OCH_2CH_2CN$)(N(i-pr)$_2$), thus forming a nucleoside phosphoramidite synthon; and d) performing oligonucleotide synthesis using at least one of said nucleoside phosphoramidite synthon therein. In some such embodiments, the reagent in step (b) is 2-cyanoethyl tetraisopropylphosphorodiamidite.

In some embodiments, the invention provides methods for synthesizing an oligomeric compound comprising a moiety of formula:

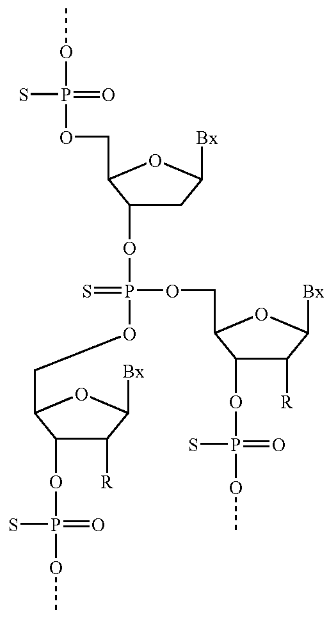

wherein:

each Bx is independently a nucleobase;

each R is a 2'-substituent; and

Pg is a protecting group;

comprising the steps of:

a) providing a diamidite of formula:

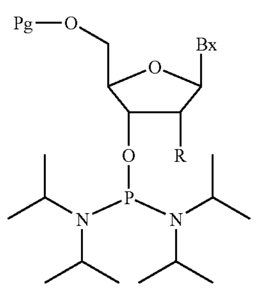

and b) using said amidite as a synthon other than a first synthon in solid phase oligonucleotide synthesis on a solid support. In some embodiments, Bx of said amidite is selected from optionally protected A, T, G, C, or 5-methyl C.

In some embodiments, the present invention provides compounds having the formula:

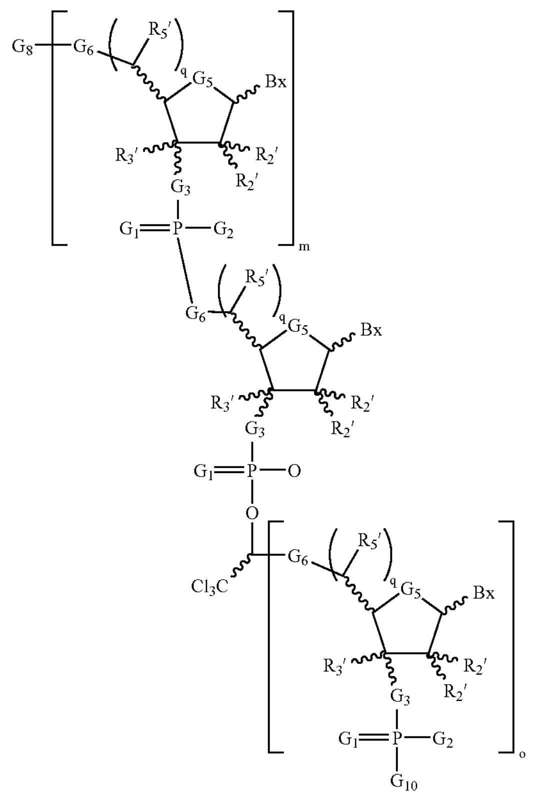

each $G_1$ is O or S;

where pg is a protecting group, each $G_2$ is OH or SH;

each $G_3$ is O, S, $CH_2$, or NH;

each $G_5$ is O, S, $CH_2$, CFH, $CF_2$, or —CH═CH—;

each $R_2$' is H, OH, O-rg, wherein rg is a removable protecting group, a 2'-substituent, or together with $R_4$' forms a bridge;

each $R_3$' is H, a substituent, or together with $R_4$' forms a bridge;

each $R_4$' is H, a substituent, or together with $R_2$' forms a bridge, together with $R_{3'}$ forms a bridge, or together with $R_5$' forms a bridge;

each q is 0 or 1;

each $R_5$' is H, a substituent, or together with $R_4$' forms a bridge; each $G_6$ is O, S, $CH_2$ or NH;

$G_8$ is H or a protecting group;

$G_{10}$ is OH, O-Pg, a nucleoside, a nucleotide, or a nucleoside linked to a solid support or to a conjugate group;

Pg is a protecting group;

m is an integer from 0 to about 100;

n is an integer from 1 to about 100; and each Bx is a naturally occurring or modified nucleobase;

In some embodiments, the compounds have the formula:

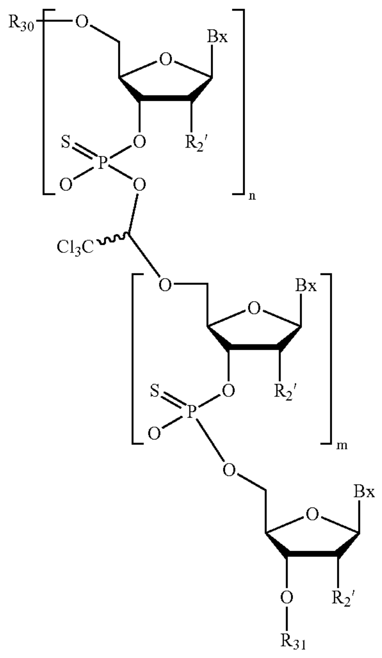

wherein:

$R_{30}$ is H or a protecting group;

$R_{31}$ is H, a protecting group, $PO_3H_2$, or a conjugate group.

In some embodiments, the present invention provides oliogonucleotides comprising one or more internucleoside linkages of formula:

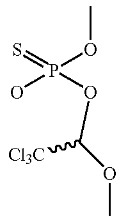

In some further embodiments, the invention provides methods of characterizing a sample comprising one or more oligomers and at least one impurity, the method comprising:

providing said sample comprising one or more oligomers and at least one impurity;

obtaining an impurity sample signal from said impurity in said sample;

comparing the impurity sample signal with a standard signal to determine the amount of said impurity in said sample; and either rejecting said sample if the amount of the impurity is greater than a predetermined critical impurity threshold, or accepting said sample if the amount of the impurity is less than or equal to said predetermined impurity threshold;

wherein said impurity has the formula LL, LLI or LLII;

wherein either:

i) said standard signal is obtained from an internal standard in said determination having said formula I; or ii) said standard signal is a property of said impurity. In some embodiments, the standard signal is a property of said impurity, for example a HPLC retention time, NMR signal or MS peak characteristic of said impurity.

In some embodiments, the present invention provides methods for the synthesis of a compound of formula:

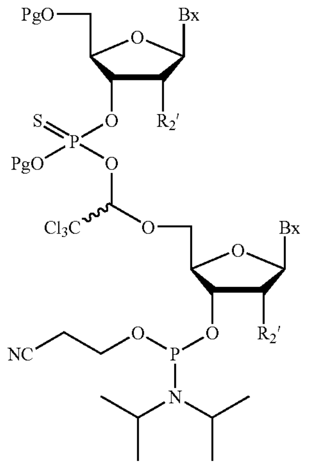

wherein:

each Pg is an independently selected protecting group;

Bx is a nucleobase; and $R_{2'}$ is H, OH, O-Pg or a 2'-substituent group;

Comprising the steps of:

a) providing a 3'-protected nucleoside of formula:

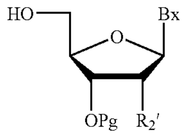

wherein:

b) reacting the 3'-protected nucleoside with chloral hydrate under conditions effective to form a compound of formula:

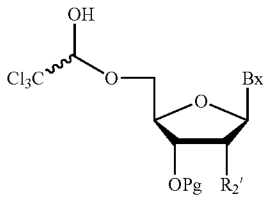

c) reacting said compound formed in step (b) with a 5'-protected nucleoside phosphoramidite, and then 3'-deprotected to form a compound of formula:

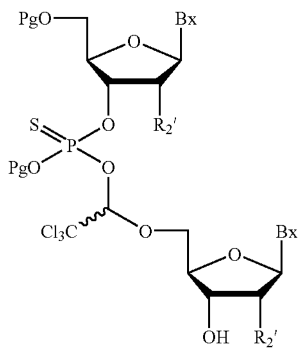

and d) phosphitylating the compound formed in step (c) to form said compound.

In some embodiments, the present invention provides methods for preparing an oliogonucleotide comprising one or more internucleoside linkages of formula:

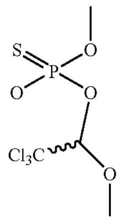

Comprising:

Providing a phosphoramidite synthon of formula:

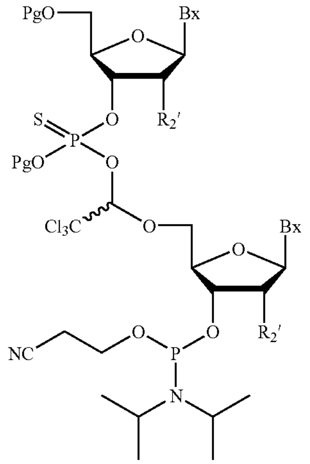

and performing oligonucleotide synthesis using at least one of said phosphoramidite synthons therein. In some such embodiments, the Pg at the 5'-positions are DMT, and the PG groups attached to the internucleoside linkages are beta cyanoethyl groups.

The present invention further provides synthetic methods comprising:

a) providing a compound of formula L:

L

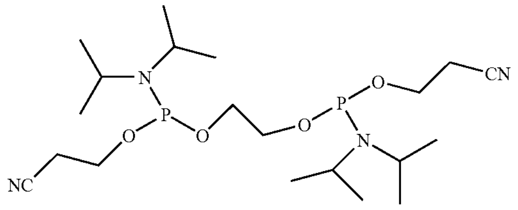

and b) reacting said compound with a 5'-protected nucleoside of formula:

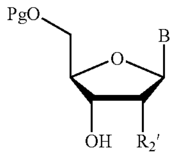

Wherein Pg is a protecting group;

B is a nucleobase; and $R_{2'}$ is H, OH, O-Pg or a 2'-substituent group;

under conditions effective to form a compound of formula LI:

LI

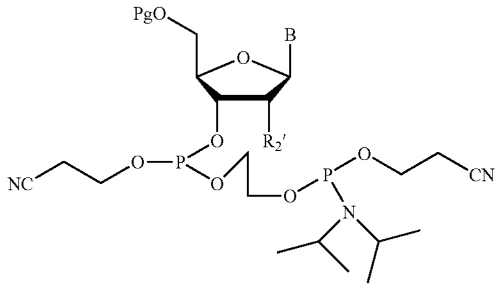

In some such embodiments, the compound provided in step (a) is prepared by reacting a compound of formula:

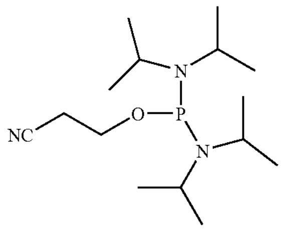

with 1,2-dihydroxyethane. In some such embodiments, Pg is DMT. In some further embodiments, the methods further comprising the step of performing oligonucleotide synthesis using at least one of said nucleoside phosphoramidite synthons of formula LI therein.

In some embodiments, the invention provides methods of characterizing a sample comprising one or more compounds, said compounds comprising oligomers and/or nucleoside phosphoramidites, and at least one impurity, the method comprising:

providing said sample comprising one or more of said compounds and at least one impurity;

obtaining an impurity sample signal from said impurity in said sample;

comparing the impurity sample signal with a standard signal to determine the amount of said impurity in said sample; and either rejecting said sample if the amount of the impurity is greater than a predetermined critical impurity threshold, or accepting said sample if the amount of the impurity is less than or equal to said predetermined impurity threshold;

wherein said impurity has the formula I:

I

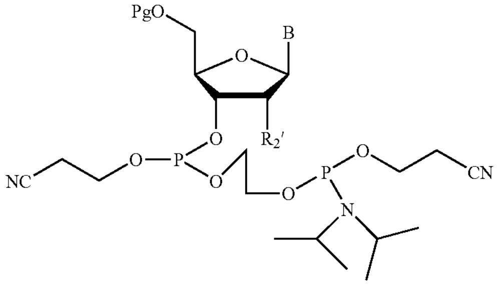

wherein:

Pg is a protecting group;

$R_{2'}$ is H, OH, O-Pg or a 2'-substituent group;

B is a nucleobase;

wherein either:

i) said standard signal is obtained from an internal standard in said determination having said formula I; or ii) said standard signal is a property of said impurity. In some embodiments, the standard signal is a property of said impurity, for example a HPLC retention time, NMR signal or MS peak characteristic of said impurity.

The present invention further provides compounds having one of the formulas:

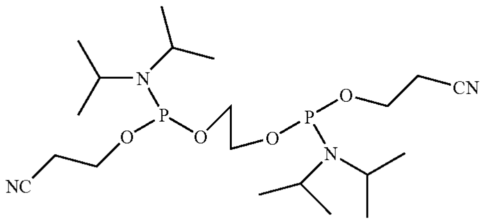

or

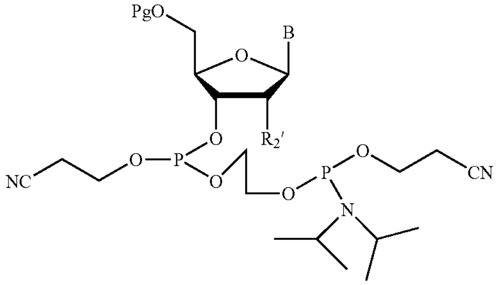

wherein:

Pg is a protecting group;

$R_{2'}$ is H, OH, O-Pg or a 2'-substituent group;

B is a nucleobase;

wherein said compound is at least one percent pure. In some embodiments, Pg is DMT.

In some embodiments, the invention provides compounds having the formula LX:

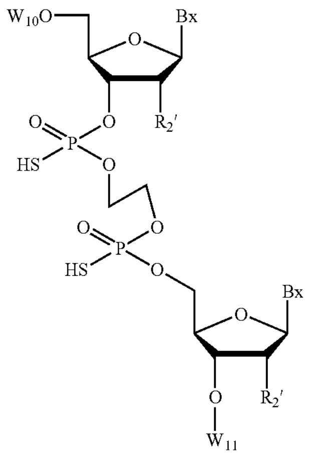

wherein:

$W_{10}$ is a H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

In some further embodiments, the invention provides compounds having one of the formulas LX, LXI or LXII:

LX

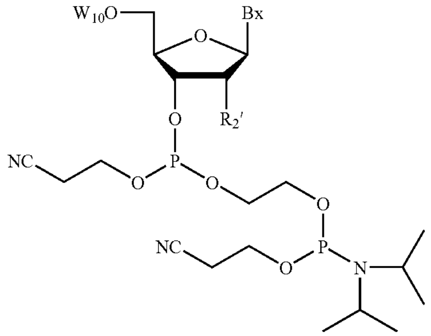

-continued

LXI

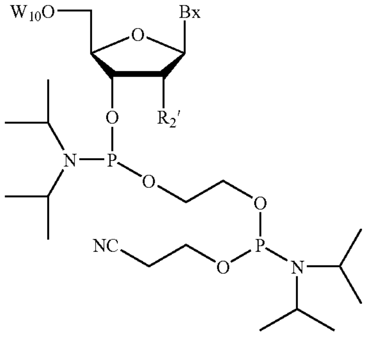

LXII

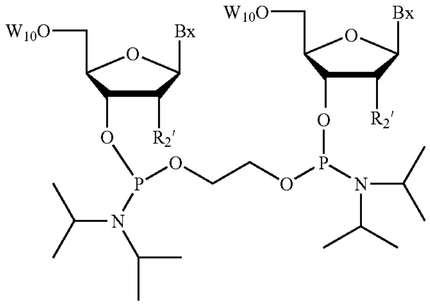

wherein:

each $W_{10}$ is H or a protecting group;

Bx is a nucleobase; and $R_{2'}$ is H, OH, O-Pg or a 2'-substituent group;

In some embodiments, the invention provides oligomeric compounds comprising a moiety of formula LXIII or LXIV:

LXIII

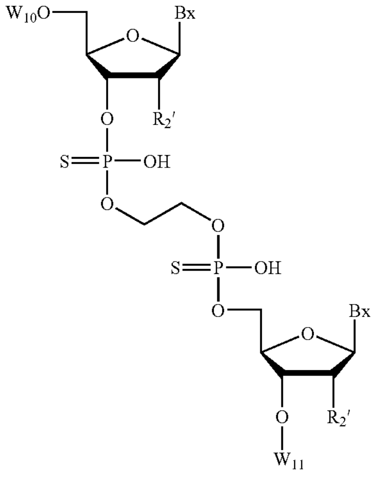

-continued

LXIV

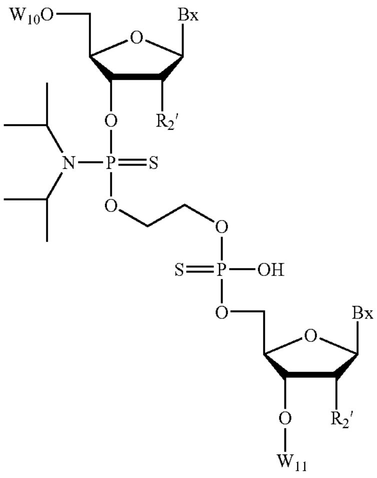

wherein:

$W_{10}$ is H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

wherein said compound is at least one percent pure.

In further embodiments, the invention provides compounds having the formula LXV:

LXV

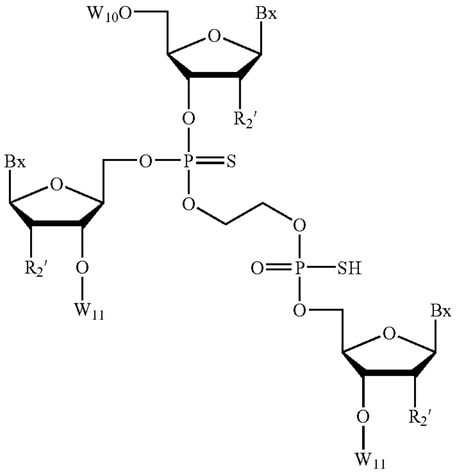

wherein:

$W_{10}$ is a H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

The present invention further provides compounds of formula LXX:

LXX

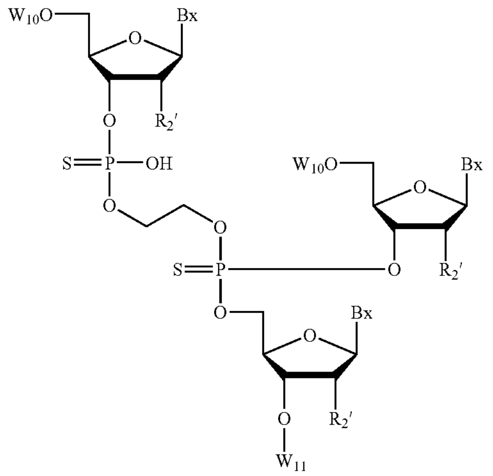

each $W_{10}$ is independently H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

The present invention further provides compounds having the formula LXXX:

LXXX

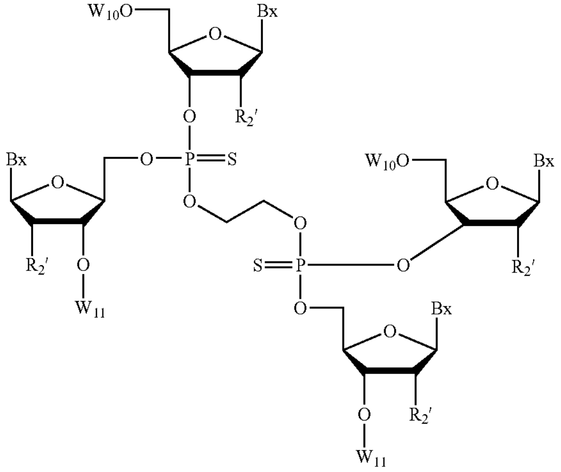

wherein:

each $W_{10}$ is independently H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

The present invention further provides compounds having the formula:

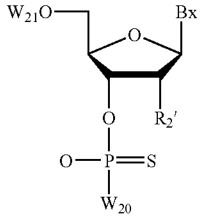

wherein:

$W_{20}$ is a 3'-oxygen atom of a nucleoside or an oligonucleotide, wherein said oligonucleoside or said oligonucleotide is optionally connected to a linker connected to a solid support;

$W_{21}$ is a 3'-oxygen atom of a nucleoside or an oligonucleotide;

Bx is a nucleobase; and $R_{2'}$ is H, OH, O-Pg or a 2'-substituent group;

The present invention further provides compounds having the formula:

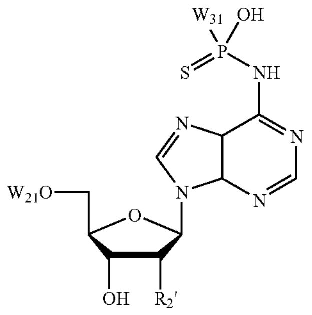

wherein:

$W_{31}$ is a 3'-oxygen atom of a nucleoside or an oligonucleotide;

$W_{21}$ is a 3'-oxygen atom of a nucleoside or an oligonucleotide;

Bx is a nucleobase; and $R_{2'}$ is H, OH, O-Pg or a 2'-substituent group;

The present invention further provides methods of characterizing a sample comprising one or more compounds, and at least one impurity, the method comprising:

providing said sample comprising one or more compounds of interest, and at least one impurity;

obtaining an impurity sample signal from said impurity in said sample;

comparing the impurity sample signal with a standard signal to determine the amount of said impurity in said sample; and either rejecting said sample if the amount of the impurity is greater than a predetermined critical impurity threshold, or accepting said sample if the amount of the impurity is less than or equal to said predetermined impurity threshold;

wherein said impurity has one of the formulas:

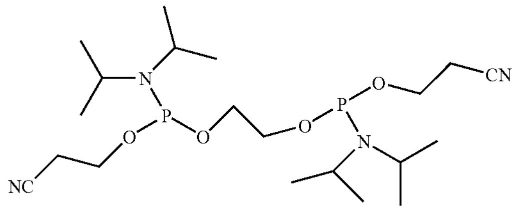

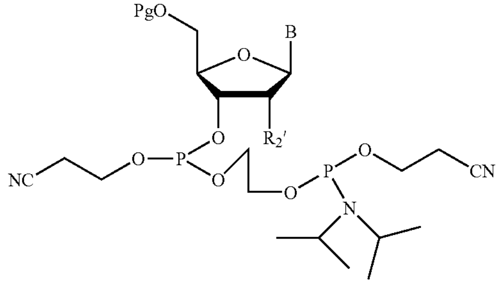

wherein:

Pg is a protecting group;

$R_{2'}$ is H, OH, O-Pg or a 2'-substituent group;

B is a nucleobase;

or

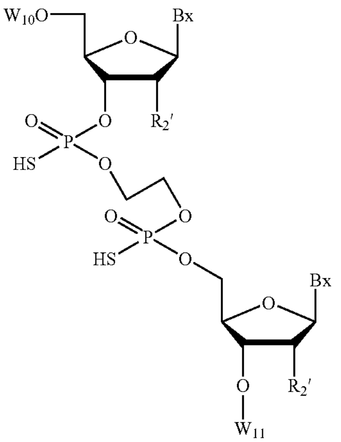

wherein:

$W_{10}$ is a H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

LX

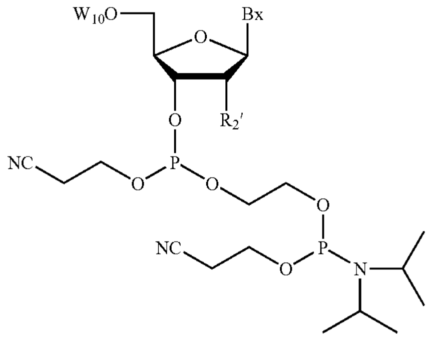

LXI

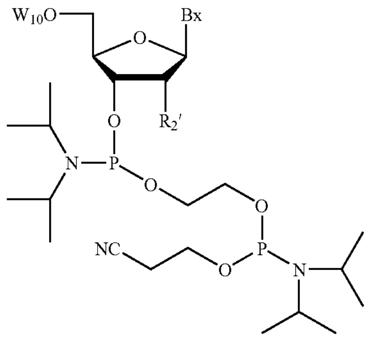

LXII

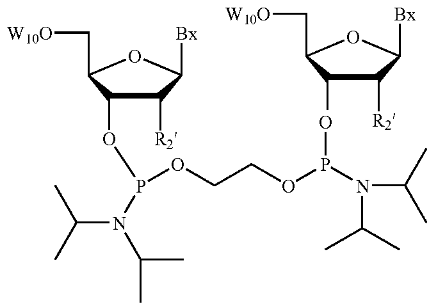

wherein:

each $W_{10}$ is H or a protecting group;

Bx is a nucleobase; and $R_{2'}$ is H, OH, O-Pg or a 2'-substituent group; or

LXIII

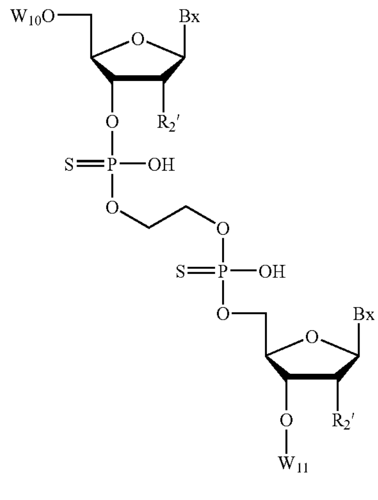

-continued

LXIV

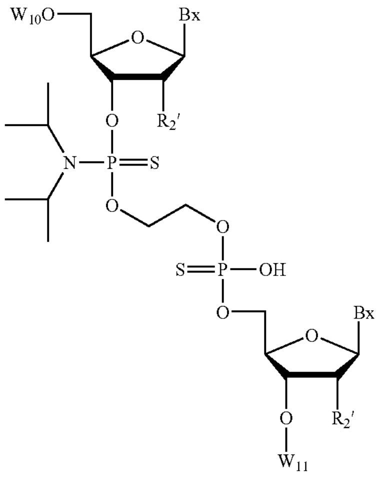

wherein:

$W_{10}$ is a H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group;

LXV

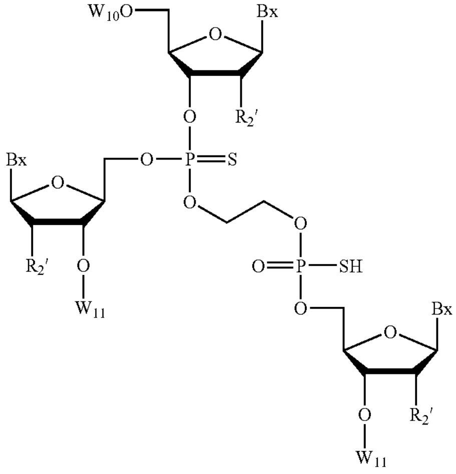

wherein:

$W_{10}$ is a H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group; or

LXX

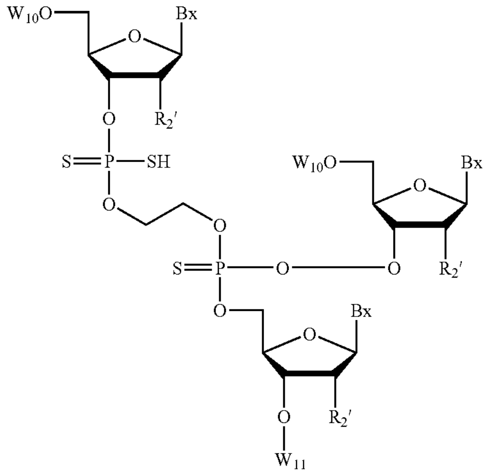

wherein:

each $W_{10}$ is independently H, a protecting group, a nucleotide or an oligonucleotide having an internucleoside linkage attached to the 3'-terminal thereof;

$W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group; or

LXXX

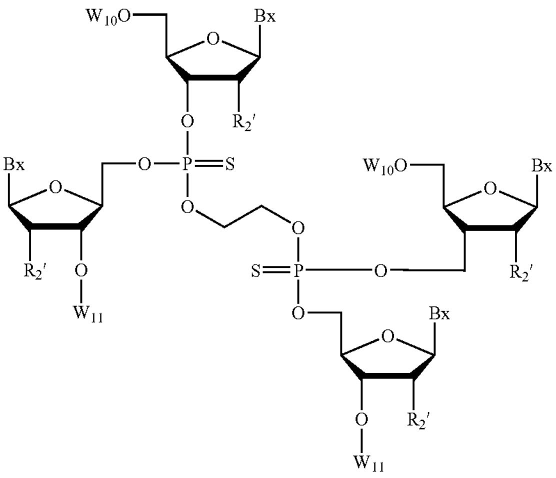

wherein:

each $W_{10}$ is independently H, a protecting group, a nucleotide or an oligonucleotide having an internucleoside linkage attached to the 3'-terminal thereof, $W_{11}$ is H, a protecting group, a linker connected to a solid support; an internucleoside linkage connected to nucleoside linked to a solid support, or an internucleoside linkage connected to an oligonucleotide, wherein said oligonucleoside is optionally connected to a linker connected to a solid support;

Bx is a nucleobase; and $R_{2'}$ is H, OH, O-Pg or a 2'-substituent group; or

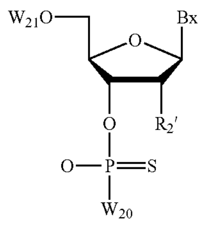

wherein:

$W_{20}$ is a 3'-oxygen atom of a nucleoside or an oligonucleotide, wherein said oligonucleoside or said oligonucleotide is optionally connected to a linker connected to a solid support;

$W_{21}$ is a 3'-oxygen atom of a nucleoside or an oligonucleotide;

Bx is a nucleobase; and $R_{2'}$ is H, OH, O-Pg or a 2'-substituent group; or

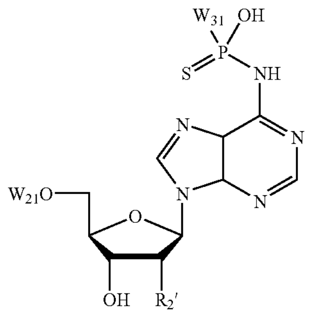

wherein:

$W_{31}$ is a 3'-oxygen atom of a nucleoside or an oligonucleotide;

$W_{21}$ is a 3'-oxygen atom of a nucleoside or an oligonucleotide;

Bx is a nucleobase; and $R_{2'}$ is H, OH, O-Pg or a 2'-substituent group; or wherein either:

i) said standard signal is obtained from an internal standard in said determination having said formula I; or ii) said standard signal is a property of said impurity.

In some such embodiments, said standard signal is a property of said impurity, for example a HPLC retention time, NMR signal or MS peak characteristic of said impurity.

The present invention further provides a synthetic method comprising:

providing a compound of formula:

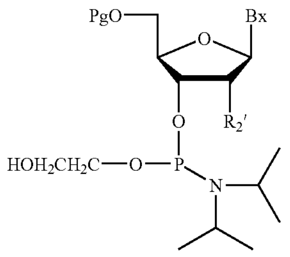

wherein:

Pg is a protecting group;

$R_{2'}$ is H, OH, O-Pg or a 2'-substituent group; and

B is a nucleobase;

and reacting said compound with a compound of formula $P(N\text{-}_{ipr})_2)(OCH_2CH_2CN)Cl$ under conditions effective to provide a compound of formula:

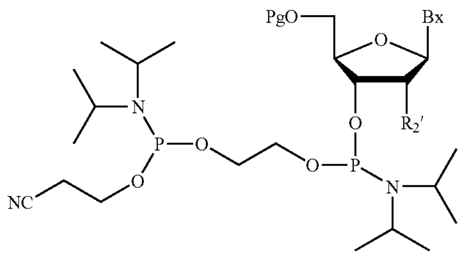

The present invention further provides a synthetic method comprising:

providing a compound of formula:

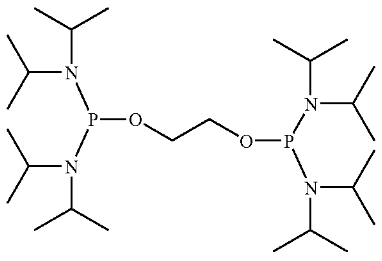

and reacting said compound with a 3'-protected nucleoside to form a compound of formula:

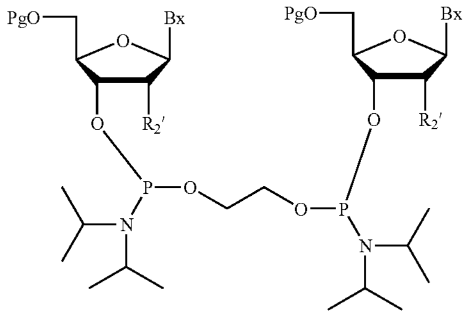

wherein:

Pg is a protecting group;

$R_{2'}$ is H, OH, O-Pg or a 2'-substituent group; and

B is a nucleobase.

The present invention further provides a synthetic method comprising:

providing a compound of formula:

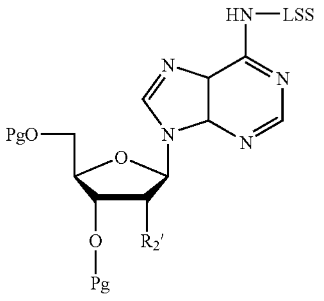

wherein:

each Pg is a protecting group;

$R_{2'}$ is H, OH, O-Pg or a 2'-substituent group; and

LSS is a linker connected to a solid support;

and performing solid phase oligonucleotide synthesis on said compound to form a compound of formula:

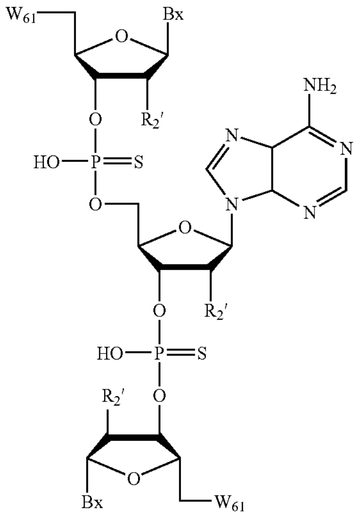

wherein:

each $W_{61}$ is OH, an internucleoside linkage, or an internucleoside linkage attached to the 3'-oxygen atom of a nucleoside or an oligonucleotide;

each Bx is a nucleobase; and $R_{2'}$ is H, OH, O-Pg or a 2'-substituent group.

The present invention further provides A synthetic method comprising:

providing a compound of formula:

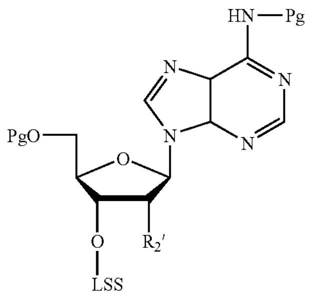

wherein:

each Pg is a protecting group;

$R_{2'}$ is H, OH, O-Pg or a 2'-substituent group; and

LSS is a linker connected to a solid support;

and performing solid phase oligonucleotide synthesis on said compound to form a compound of formula:

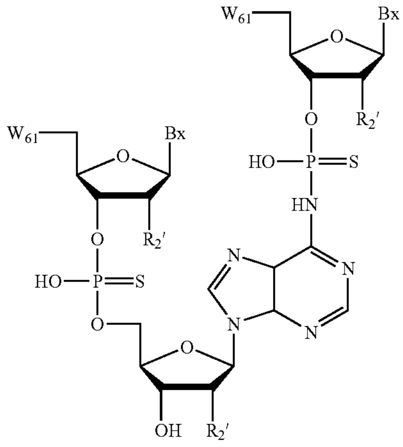

wherein:

each $W_{61}$ is OH, an internucleoside linkage, or an internucleoside linkage attached to the 3'-oxygen atom of a nucleoside or an oligonucleotides.

In some embodiments of the compounds and methods of the invention, the nucleobases are optionally protected, and are independently selected from adenine, guanine, thymine, cytosine, uracil and 5-methylcytosine.

In some embodiments of the methods of the invention, said standard signal is a property of said impurity, for example a HPLC retention time, NMR signal or MS peak characteristic of said impurity.

In some embodiments of the compounds of the invention, the compound is greater than about 1% pure, or greater than about 2% pure, 5% pure, 10% pure, 20% pure, 30% pure, 40% pure, 50% pure, 60% pure, 70% pure, 80% pure, 90% pure, 950% pure, 98% pure, 99% pure or substantially 100% pure as determined by weight with reference to the other components of the system.

The present invention further provides products of the processes described herein.

Other uses and advantages of the present invention will become apparent to the artisan upon consideration of the foregoing specification and claims.

DETAILED DESCRIPTION OF THE INVENTION

Figure 1:
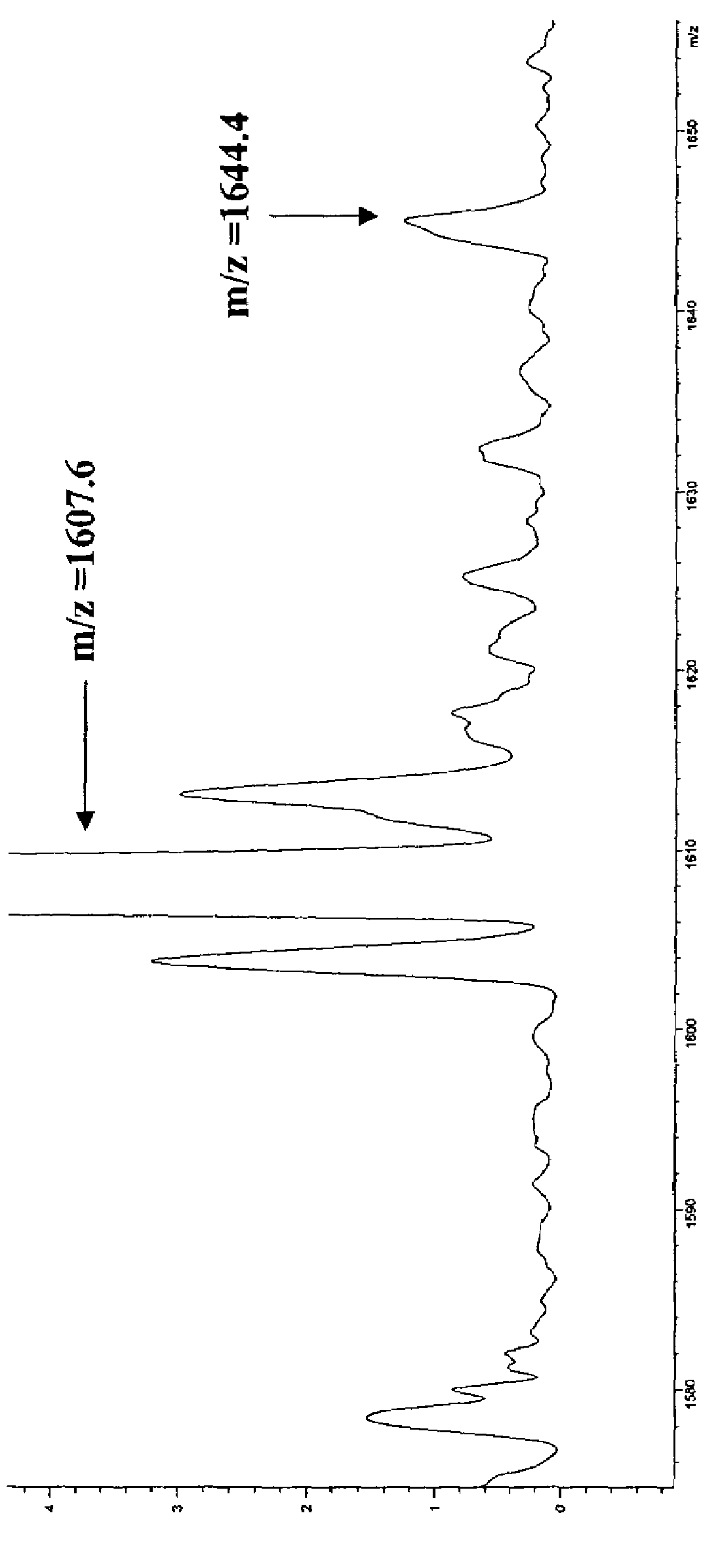
FIG. 1 shows the average mass spectrum of the main UV peak obtained by ion pair-liquid chromatography analysis of a typical batch of ISIS 3521 drug substance.

In some embodiments, the present invention provides compounds of Formula I, II or III:

I

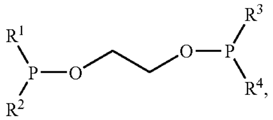

II

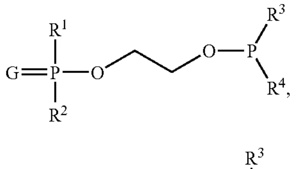

III

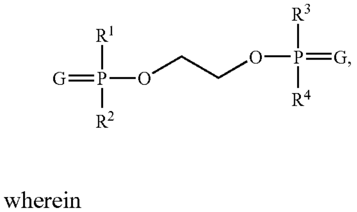

wherein each $R^1$, $R^2$, $R^3$ and $R^4$ is independently a 2'-O—, 3'-O—, or 5'-O— linked nucleoside optionally attached to solid support, a 2'-O—, 3'-O—, or 5'-O— linked oligonucleotide optionally attached to solid support, $—N^iPr_2$, $—O(CH_2)_2CN$, —OH or —SH, and each G is independently O or S.

In one embodiment of the invention $R^1$, $R^2$, $R^3$ and $R^4$ are $—N^iPr_2$ or $—O(CH_2)_2CN$.

In another embodiment of the invention at least one of $R^1$, $R^2$, $R^3$ or $R^4$ is a 2'-O—, 3'-O—, or 5'-O— linked nucleoside optionally attached to solid support or a 2'-O—, 3'-O—, or 5'-O— linked oligonucleotide optionally attached to solid support.

In other embodiments at least two of $R^1$, $R^2$, $R^3$ or $R^4$ are 2'-O—, 3'-O—, or 5'-O— linked nucleosides optionally attached to solid support or 2'-O—, 3'-O—, or 5'-O— linked oligonucleotides optionally attached to solid support.

In yet other embodiments at least three of $R^1$, $R^2$, $R^3$ or $R^4$ are 2'-O—, 3'-O—, or 5'-O— linked nucleosides optionally attached to solid support or 2'-O—, 3'-O—, or 5'-O— linked oligonucleotides optionally attached to solid support.

In a further embodiment $R^1$, $R^2$, $R^3$ and $R^4$ are 2'-O—, 3'-O—, or 5'-O— linked nucleosides optionally attached to solid support or 2'-O—, 3'-O—, or 5'-O— linked oligonucleotides optionally attached to solid support.

In certain embodiments of the invention, when one of $R^1$, $R^2$, $R^3$ and $R^4$ is attached to solid support, then the remainder are not attached to solid support.

In another embodiment the compounds of Formula I, II or III are not attached to solid support.

In other embodiments, the present invention provides compounds of Formula VI:

IV

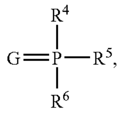

wherein each $R^4$, $R^5$ and $R^6$ is independently a 2'-O—, 3'-O—, or 5'-O— linked nucleoside optionally attached to solid support, a 2'-O—, 3'-O—, or 5'-O— linked oligonucleotide optionally attached to solid support, and G is O or S.

In certain embodiments of the invention, when one of $R^4$, $R^5$ or $R^6$ is attached to solid support, then the remainder are not attached to solid support. In another embodiment the compounds of Formula IV are not attached to solid support.

In further embodiments, the present invention provides compounds of Formula V:

V

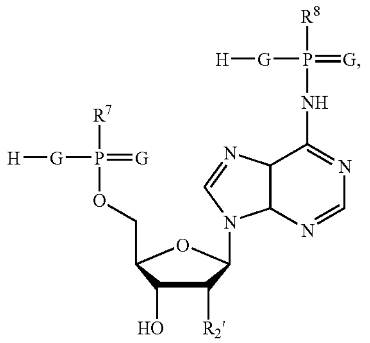

wherein $R^7$ and $R^8$ are independently a 2'-O—, 3'-O—, or 5'-O— linked nucleoside optionally attached to solid support, a 2'-O—, 3'-O—, or 5'-O— linked oligonucleotide optionally attached to solid support, —SH or —OH, each G is independently O or S, and $R_2$' is H, OH, O-rg wherein rg is a removable protecting group, or a 2' substituent.

In another embodiment, when one of $R^7$ and $R^8$ is attached to solid support, then the other is not attached to solid support. In further embodiments, the compounds of Formula V are not attached to solid support.

In some embodiments of the invention the compounds of formula I, II, III, IV, or V are at least 1 percent pure. In another embodiment of the invention the compounds of formula I, II, III, IV, or V are greater than about 1, 2, 3, 4, 5, 6, 7, 8, 9, or 10 percent puer. In a preferred embodiment, the compounds of formula I, II, III, IV, or V are greater than 10 percent pure. In other preferred embodiments, the compounds of formula I, II, III, IV, or V are greater than 50 percent pure. In another aspect of the invention, any of the compounds disclosed herein are greater than about 1, 2, 3, 4, 5, 6, 7, 8, 9, or 10 percent pure.

The present invention is concerned with the art of oligonucleotide synthesis, and in particular with providing starting materials of excellent purity, the use of which will provide oligonucleotides having excellent purity. The invention provides, in some embodiments, methods of identifying samples as starting materials having purity profiles suitable for synthesizing oligonucleotides having excellent purity, and in some embodiments purity sufficient to qualify the oligonucleotides for inclusion in drug preparations.

In some embodiments, the methods according to the present invention comprise identifying an impurity, identifying at least one impurity signal that is representative of the impurity concentration in the sample, detecting said impurity signal in the sample, determining from the impurity signal the impurity concentration, comparing the quantity of impurity with a predetermined impurity threshold, rejecting the sample if the quantity of impurity exceeds the predetermined impurity threshold, or accepting the sample as a starting material if the quantity of the identified impurity does not exceed the impurity threshold.

The impurity may be further classified as either a critical impurity or a non-critical impurity. A critical impurity is an impurity that reacts with a nascent oligonucleotide chain during synthesis, and which permits further chain extension upon reaction. Certain critical impurities react with the 5'-OH of the nascent oligonucleotide chain, and themselves are capable of reacting with an amidite, thereby giving rise to oligonucleotides having incorporated therein the impurity as a constituent part. Other critical impurities react with the nascent oligonucleotide chain at positions other than the 5'-OH, and are incorporated into the oligonucleotide as adducts. Some critical impurities give rise to branchmers. Other critical impurities give rise to adducts. Exemplary critical impurities will be illustrated in more detail below.

Non-critical impurities are impurities that are either inert with respect to the nascent oligonucleotide chain or non-inert. Inert non-critical impurities are those impurities that do not react with the nascent oligonucleotide. Non-inert non-critical impurities are those impurities that react with the oligonucleotide chain but result in the termination of the oligonucleotide sequence, and thus are similar in chemical behavior to capping. In the context of this invention, then, a non-inert non-critical impurity may be referred to as a capping impurity.

Impurities, whether critical or non-critical, may arise out of one or more of the process steps used to make the components of the sample, or may result from degradation of components of the sample.

In some embodiments, the nucleobase Bx is one of the moieties:

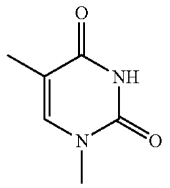

T

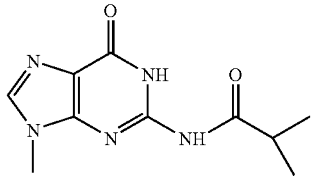

ibuG

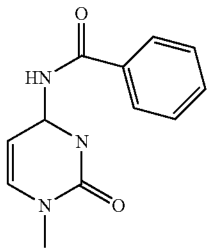

bzC or

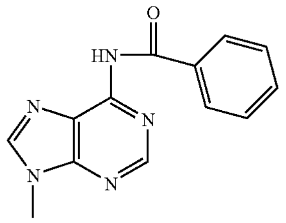

bzA

The impurity signal may be a signal that is representative of the concentration of the impurity in a sample. Suitable signals may include an absorption signal, a fluorescence signal, a phosphorescence signal, a mass spectrometry signal, etc. An absorption signal includes ultraviolet light absorption signal, a nuclear magnetic resonance signal, a visible light absorption signal, etc. Such a signal may be gathered by, for example, an HPLC instrument with an absorption detector, e.g. an ultraviolet detector. A mass spectrometry signal may include an HPLC-mass spectrometry signal.

In the context of the present invention, the impurity signal may vary linearly, log-linearly, log-log, or otherwise with respect to the impurity concentration.

In some specific embodiments according to the present invention, an authentic impurity may be prepared and subjected to HPLC, whereby there is produced an impurity signal, the impurity signal comprising an HPLC retention time and a detector signal strength that varies in a consistent relationship to the amount of authentic impurity applied to the HPLC column. Thus, an impurity signal may be multidimensional, comprising a first signal component representing the identity of the impurity (in the case of HPLC, retention time; in the case of mass-spectrometry, m/z) and a second signal component representative of impurity concentration (in the case of HPLC, UV absorbance; in the case of mass-spectrometry, electrode signal strength). The signal component that is representative of impurity identity may be thought of as a qualitative component, while the signal component that is representative of the impurity's concentration in the sample may be thought of as a quantitative component.

Once the relationship is established between an impurity's concentration and the qualitative component of the impurity signal, a sample may be subjected to the same testing method to determine whether the impurity is present in the sample (a qualitative determination) and if so, at what concentration (quantitative determination). For example in HPLC, a portion of a sample is applied to a column and the retention times and areas of at least two peaks (one representing a desired compound, and one representing the impurity) are recorded. The retention times are used to identify the signals relating to the compound of interest and the impurity, while the relative areas of the elution peaks of the compound and impurity are used to determine the concentration of impurity relative to the compound in the sample. In this simple example, impurity concentration, expressed as % impurity, is:

$$\%\ \text{impurity}=100\%\times(A_i/(A_i+A_A)),$$

where $A_i$ is the area under the impurity's elution peak and $A_A$ is the area under the elution peak of the compound of interest. The concentration of the impurity in the sample is then compared to a predetermined impurity limit. A sample having an impurity concentration greater than the impurity limit is classified as rejected. A rejected sample may be destroyed, recycled, further purified, or otherwise disposed of, but not used in oligonucleotide synthesis. A sample in which no impurity's concentration exceeds its predetermined impurity limit is then classified as a starting material, which may be used as a starting material for making oligonucleotide. In some embodiments, the impurity is not a starting material, but rather is generated during synthesis. I such cases, the sample is rejected or accepted as an oligomeric sample suitable for further processing to make the desired oligonucleotide.

Where n impurities are known to potentially be present in a sample, a signal may be identified for each of the n impurities. The concentration for impurity X is then calculated as:

$$\%\ X = 100\% \times Ax \Big/ \left( A_A + \sum_{i=1}^{n} Ai \right),$$

wherein $A_x$ is the area of the peak corresponding to impurity X, where X is an integer from 1 to n, $A_A$ is the area of the peak corresponding to the compound of interest, and each $A_i$ is the area of the ith impurity peak, wherein i is an integer from 1 to n. In such case, a predetermined impurity limit is selected for each impurity. If any impurity concentration exceeds its predetermined impurity threshold, the sample is rejected. If each impurity concentration is less than or equal to its impurity threshold, the sample is classified as a starting material, which may be used in oligonucleotide synthesis, or a sample suitable for further processing.

As used herein, unless otherwise modified, the term "sample" refers to a composition of matter, which contains a compound of interest, and optionally a detectable amount of at least one impurity. A sample may further be classified as a "starting material" or as suitable for further processing, or as "rejected," as described in more detail herein.

As used herein, unless otherwise modified, the term "starting material" refers to a composition of matter, which contains a compound of interest and optionally a detectable amount of at least one impurity, and which has been classified as "starting material" according to a method of the present invention. In many cases, more than one impurity will be present in the "starting material." Thus, a starting material is a sample that has been subjected to testing as described herein, and has been determined to contain no more than the impurity threshold of each impurity tested for.

As used herein, unless otherwise modified, the term "rejected sample" refers to a sample that has been subjected to testing by the inventive method described herein, and has been found to contain at least one impurity at a concentration greater than its impurity threshold. It should be noted that if there are n identified impurities potentially in a sample, there will potentially be n signals corresponding to the n impurities. There also may be a signal relating to the compound of interest itself.

As used herein, unless otherwise modified, the term "signal" refers to a voltage, UV absorbance, current, or other value, whether analog or digital, that represents some characteristic of an impurity or a compound of interest. As described above, a signal may comprise more than one component, e.g. a qualitative component and a quantitative component. For example, as pointed out above, an HPLC chromatogram comprises a time component (retention time), useful for identifying the signal relating to an impurity or compound of interest, and an absorbance component (UV absorbance), useful for determining the amount of impurity or compound of interest in the sample.

The term impurity includes any compound other than amidite or solvent, if any, whether actually present in the amidite sample or not, and whether identified or not. A potential impurity is an impurity that has been hypothesized to be present in a sample, whether actually present or not. An unidentified impurity is an impurity whose structure is not known, but which is detected in the sample. In some cases, a group of impurities may be collected into an "unidentified impurity" classification. A known impurity is an impurity whose structure is known. In accordance with the present invention, a known impurity in a sample can be identified and its quantity measured by obtaining its characteristic signal from both a reference (authentic compound) and the sample.

Known impurities may be further subdivided into critical impurities and non-critical impurities, as described herein.

Detection of an impurity in a sample may be conducted using a suitable analytical method, such as HPLC, Mass-Spectrometry, GC-Mass Spec, etc. The artisan will recognize that a method capable of unambiguously identifying and quantifying an impurity in a sample will be suitable for the disclosed methodology.

As used herein, the term oligonucleotide has the meaning of an oligomer having m subunits embraced within the brackets [ ] of the formula:

Oligonucleotide

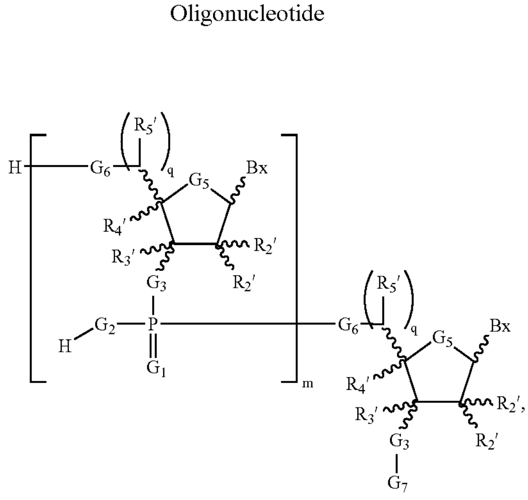

wherein the other variables are defined above, and are described in more detail hereinafter. It is to be understood that, although the oligonucleotide to be made is depicted in a single stranded conformation, it is common for oligonucleotides to be used in a double stranded conformation. For example, in the antisense method referred-to commonly as siRNA, two strands of RNA or RNA-like oligonucleotide are prepared and annealed together, often with a two-nucleotide overlap at the ends. Thus, the present invention contemplates manufacture of both single- and double-stranded oligonucleotides.

Nucleobases

The nucleobases Bx may be the same or different, and include naturally occurring nucleobases adenine (A), guanine (G), thymine (T), uracil (U) and cytosine (C), as well as modified nucleobases. Modified nucleobases include heterocyclic moieties that are structurally related to the naturally-occurring nucleobases, but which have been chemically modified to impart some property to the modified nucleobase that is not possessed by naturally-occurring nucleobases. The term "nucleobase," as used herein, is intended to by synonymous with "nucleic acid base or mimetic thereof." In general, a nucleobase is any substructure that contains one or more atoms or groups of atoms capable of hydrogen bonding to a base of an oligonucleotide.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2thiocytosine, 5-halouracil and cytosine, 5-propynyl ($—C≡C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

In some embodiments of the invention, oligomeric compounds, e.g. oligonucleotides, are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

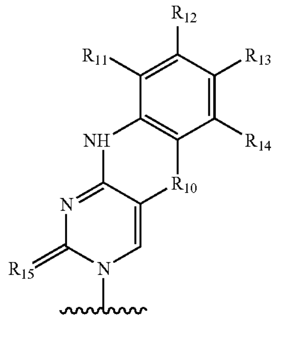

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides,* 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

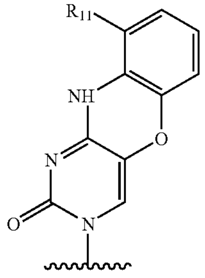

Wherein $R_{11}$ includes $(CH_3)_2N$—$(CH_2)_2$—O—; $H_2N$—$(CH_2)_3$—; Ph-$CH_2$—O—C(=O)—N(H)—$(CH_2)_3$—; $H_2N$—; Fluorenyl-$CH_2$—O—C(=O)—N(H)—$(CH_2)_3$—; Phthalimidyl-$CH_2$—O—C(=O)—N(H)—$(CH_2)_3$—; Ph-$CH_2$—O—C(=O)—N(H)—$(CH_2)_2$—O—; Ph-$CH_2$—O—C(=O)—N(H)—$(CH_2)_3$—O—; $(CH_3)_2N$—N(H)—$(CH_2)_2$—O—; Fluorenyl-$CH_2$—O—C(=O)—N(H)—$(CH_2)_2$—O—; Fluorenyl-$CH_2$—O—C(=O)—N(H)—$(CH_2)_3$—O—; $H_2N$—$(CH_2)_2$—O—$CH_2$—; $N_3$—$(CH_2)_2$—O—$CH_2$—; $H_2N$—$(CH_2)_2$—O—, and $NH_2C$(=NH)NH—.

Also disclosed are tricyclic heterocyclic compounds of the formula:

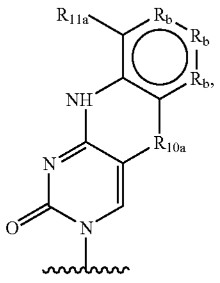

wherein:

$R_{10a}$ is O, S or N—$CH_3$; $R_{11a}$ is $A(Z)_{x1}$, wherein A is a spacer and Z independently is a label bonding group bonding group optionally bonded to a detectable label, but $R_{11a}$ is not amine, protected amine, nitro or cyano; X1 is 1, 2 or 3; and $R_b$ is independently —CH=, —N=, —C($C_{1-8}$ alkyl)=or —C(halogen)=, but no adjacent $R_b$ are both —N=, or two adjacent $R_b$ are taken together to form a ring having the structure:

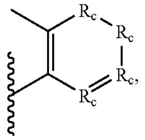

where $R_c$ is independently —CH=, —N=, —C($C_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

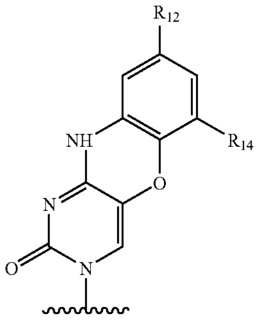

and

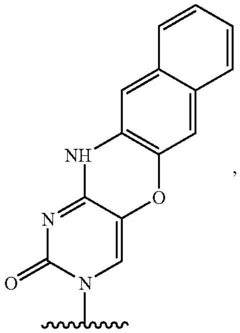

, wherein $R_{14}$ is $NO_2$ or both $R_{14}$ and $R_{12}$ are independently —$CH_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" Patents include those having the formula:

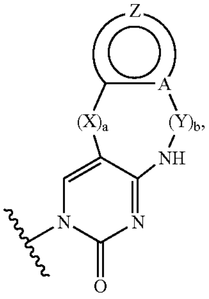

wherein a and b are independently 0 or 1 with the total of a and b being 0 or 1; A is N, C or CH; X is S, O, C=O, NH or $NCH_2$, $R^6$; Y is C=O; Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 nonbridging ring carbon atom is substituted with $R^{20}$ or =O; or Z is taken together with A to form an aryl ring structure comprising 6 ring atoms wherein the aryl ring carbon atoms are unsubstituted with other than H or at least 1 nonbridging ring carbon atom is substituted with $R^6$ or =O; $R^6$ is independently H, $C_{1-6}$ alkyl, $C_{2-6}$ alkenyl, $C_{2-6}$ alkynyl, $NO_2$, $N(R^3)_2$, CN or halo, or an $R^6$ is taken together with an adjacent Z group $R^6$ to complete a phenyl ring; $R^{20}$ is, independently, H, $C_{1-6}$ alkyl, $C_{2-6}$ alkyl, $C_{2-6}$ alkenyl, $C_{2-6}$ alkynyl, $NO_2$, $N(R^{21})_2$, CN, or halo, or an $R^{20}$ is taken together with an adjacent $R^{20}$ to complete a ring containing 5 or 6 ring atoms, and tautomers, solvates and salts thereof; $R^{21}$ is, independently, H or a protecting group; $R^3$ is a protecting group or H; and tautomers, solvates and salts thereof.

More specific examples of bases included in the "257, 177 and 269" Patents are compounds of the formula:

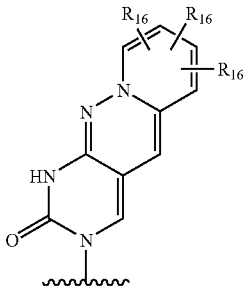

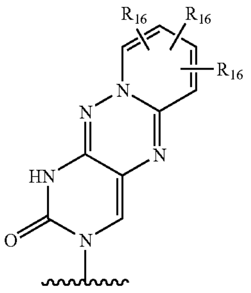

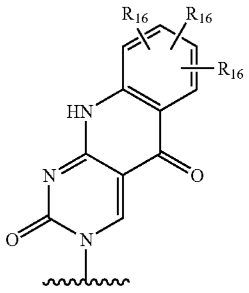

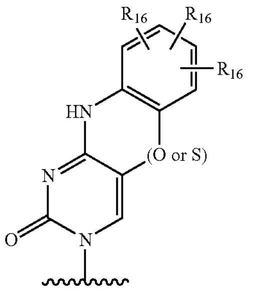

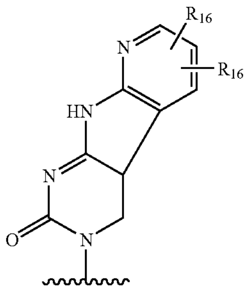

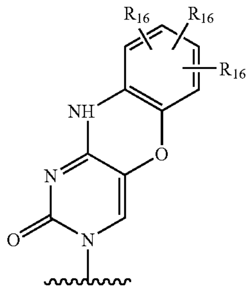

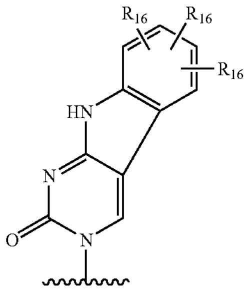

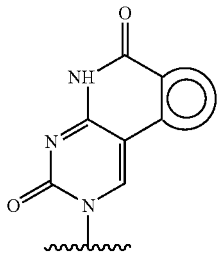

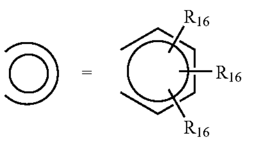

or

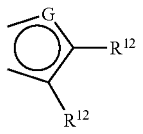

-continued

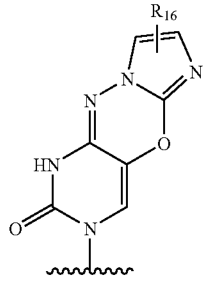

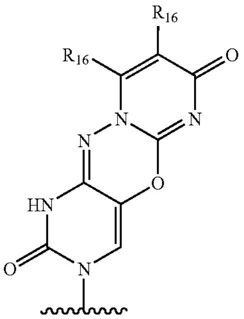

wherein each $R_{16}$, is, independently, selected from hydrogen and various substituent groups.

Further polycyclic base moieties having the formula:

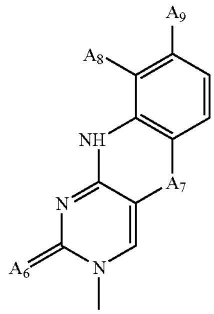

wherein: $A_6$ is O or S; $A_7$ is $CH_2$, N—$CH_3$, O or S; each $A_8$ and $A_9$ is hydrogen or one of $A_8$ and $A_9$ is hydrogen and the other of $A_8$ and $A_9$ is selected from the group consisting of:

$-O-(CH_2)_{p1}-G$ and 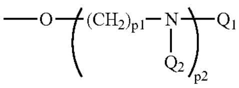

wherein: G is —CN, —$OA_{10}$, —$SA_{10}$, —N(H)$A_{10}$, —ON(H)$A_{10}$ or —C(═NH)N(H)$A_{10}$; $Q_1$ is H, —$NHA_{10}$, —C(═O)N(H)$A_{10}$, —C(═S)N(H)$A_{10}$ or —C(═NH)N(H)$A_{10}$; each $Q_2$ is, independently, H or Pg; $A_{10}$ is H, Pg, substituted or unsubstituted $C_1$-$C_{10}$ alkyl, acetyl, benzyl, —$(CH_2)_{p3}NH_2$, —$(CH_2)_{p3}N(H)Pg$, a D or L α-amino acid, or a peptide derived from D, L or racemic α-amino acids; Pg is a nitrogen, oxygen or thiol protecting group; each p1 is, independently, from 2 to about 6; p2 is from 1 to about 3; and p3 is from 1 to about 4; are disclosed in U.S. patent application Ser. No. 09/996,292 filed Nov. 28, 2001, which is commonly owned with the instant application, and is herein incorporated by reference.

Sugars and Sugar Substituents

The sugar moiety:

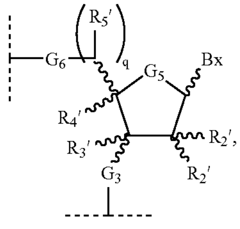

wherein each dashed line (----) indicates a point of attachment to an adjacent phosphorus atom, represents the sugar portion of a general nucleoside or nucleotide as embraced by the present invention.

Suitable 2'-substituents corresponding to $R'_2$ include: OH, F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504). A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$(CH_2)_2$—O—$(CH_2)_2$—$N(CH_3)_2$, also described in examples hereinbelow. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

The

Further representative substituent groups include groups of formula $I_a$ or $II_a$:

Ia

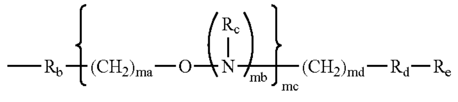

IIa

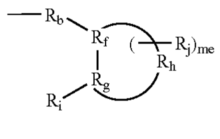

wherein: $R_b$ is O, S or NH; $R_d$ is a single bond, O or C(═O); $R_e$ is $C_1$-$C_{10}$ alkyl, $N(R_k)(R_m)$, $N(R_k)(R_n)$, N═$C(R_p)(R_q)$, N═$C(R_p)(R_r)$ or has formula $III_a$;

IIIa

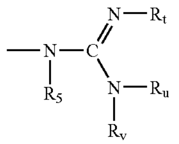

Each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl; or optionally, $R_u$ and $R_v$, together form a phthalimido moiety with the nitrogen atom to which they are attached; each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl; $R_k$ is hydrogen, a nitrogen protecting group or —$R_x$—$R_y$; $R_p$ is hydrogen, a nitrogen protecting group or —$R_x$—$R_y$; $R_x$ is a bond or a linking moiety; $R_y$ is a chemical functional group, a conjugate group or a solid support medium; each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester; or $R_m$ and $R_n$, together, are a nitrogen protecting group, are joined in a ring structure that optionally includes an additional heteroatom selected from N and O or are a chemical functional group; $R_i$ is $OR_z$, $SR_z$, or $N(R_z)_2$; each $R_z$ is, independently, H, $C_1$-$C_8$ alkyl, $C_1$-$C_8$ haloalkyl, C(═NH)N(H)$R_u$, C(═O)N(H)$R_u$ or OC(═O)N(H)$R_u$; $R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN; $m_a$ is 1 to about 10; each mb is, independently, 0 or 1; mc is 0 or an integer from 1 to 10; md is an integer from 1 to 10; me is from 0, 1 or 2; and provided that when mc is 0, md is greater than 1.

Representative substituents groups of Formula I are disclosed in U.S. Pat. No. 6,172,209. Representative cyclic substituent groups of Formula II are disclosed in U.S. Pat. No. 6,271,358.

Other particularly advantageous 2'-modifications include 2'-methoxy (2'-O—$CH_3$), 2'-aminopropoxy (2'-$OCH_2CH_2CH_2NH_2$) and 2'-fluoro (2'-F). The 2'-modification may be in the arabino (up) position or ribo (down) position. A preferred 2'-arabino modification is 2'-F. Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531; 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, issue fee paid on Oct. 23, 2002.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-MOE as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure,* 1984, Springer-Verlag; New York, N.Y.; Lesnik et al., *Biochemistry,* 1995, 34, 10807-10815; Conte et al., *Nucleic Acids Res.,* 1997, 25, 2627-2634). The increased stability of RNA has been attributed to several structural features, most notably the improved base stacking interactions that result from an A-form geometry (Searle et al., *Nucleic Acids Res.,* 1993, 21, 2051-2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry,* 1996, 35, 8489-8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., *Med. Res. Rev.,* 1996, 16, 319-344; De Mesmaeker et al., *Acc. Chem. Res.,* 1995, 28, 366-374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure,* 1984, Springer-Verlag; New York, N.Y.; Lesnik et al., *Biochemistry,* 1995, 34, 10807-10815; Conte et al., *Nucleic Acids Res.,* 1997, 25, 2627-2634). The increased stability of RNA has been attributed to several structural features, most notably the improved base stacking interactions that result from an A-form geometry (Searle et al., *Nucleic Acids Res.,* 1993, 21, 2051-2056). The presence of the 2=hydroxyl in RNA biases the sugar toward a C3=endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2=hydroxyl groups of RNA can form a network of water mediated hydrogen bonds that help stabilize the RNA duplex (Egli et al., *Biochemistry,* 1996, 35, 8489-8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2=-methoxyethoxy (MOE, 2'-$OCH_2CH_2OCH_3$) side chain (Baker et al., *J. Biol. Chem.,* 1997, 272, 11944-12000; Freier et al., *Nucleic Acids Res.,* 1997, 25, 4429-4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429-4443). 2=-O-Methoxyethyl-substituted oligonucleotides also have been shown to be antisense inhibitors of gene expression with promising features for in vivo use (Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926). Relative to DNA, they display improved RNA affinity and higher nuclease resistance. Chimeric oligonucleotides with 2=-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C,4'-C-oxymethylene linkage thereby forming a bicyclic sugar moiety. The linkage may be a methelyne $(—CH_2—)_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-deoxy-2'-$CH_2OCH_2$-4' bridge.

Alternative Linkers

In addition to phosphate diester and phosphorothioate diester linkages, other linkers are known in the art. While the primary concern of the present invention has to do with phosphate diester and phosphorothioate diester oligonucleotides, chimeric compounds having more than one type of linkage, as well as oligomers having non-phosphate/phosphorothioate diester linkages as described in further detail below, are also contemplated in whole or in part within the context of the present invention.

Exemplary non-phosphate/phosphorothioate diester linkages contemplated within the skill of the art include: phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include: thiodiester (—O—C(O)—S—), thionocarbamate (—O—C(O)(NJ)-S—), siloxane (—O—$Si(J)_2$-O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—$SO_2$—NH—), sulfide (—$CH_2$—S—$CH_2$—), sulfonate (—O—$SO_2$—$CH_2$—), N,N'-dimethylhydrazine (—$CH_2$—N($CH_3$)—N($CH_3$)—), thioformacetal (—S—$CH_2$—O—), formacetal (—O—$CH_2$—O—), thioketal (—S—$C(J)_2$-O—), ketal (—O—$C(J)_2$-O—), amine (—NH—$CH_2$—$CH_2$—), hydroxylamine (—$CH_2$—N(J)-O—), hydroxylimine (—CH═N—O—), and hydrazinyl (—$CH_2$—N(H)—N(H)—).

In each of the foregoing substructures relating to internucleoside linkages, J denotes a substituent group which is commonly hydrogen or an alkyl group or a more complicated group that varies from one type of linkage to another.

In addition to linking groups as described above that involve the modification or substitution of the —O—P—O— atoms of a naturally occurring linkage, included within the scope of the present invention are linking groups that include modification of the 5'-methylene group as well as one or more of the —O—P—O— atoms. Linkages of this type are well documented in the prior art and include without limitation the following: amides (—$CH_2$—$CH_2$—N(H)—C(O)) and —$CH_2$—O—N═CH—; and alkylphosphorus (—$C(J)_2$-P(═O)(OJ)-$C(J)_2$-$C(J)_2$-). J is as described above.

Oligonucleotide Synthesis

Oligonucleotides are generally prepared, as described above, on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support media can be soluble or insoluble, or may possess variable solubility in different solvents to allow the growing support bound polymer to be either in or out of solution as desired. Traditional support media such as solid supports are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support media is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, *Angew. Chem. Internal. Ed.* 1972, 11, 314, sold under the trademark "PORASIL E" by Waters Associates, Framingham, Mass., USA); the mono ester of 1,4-dihydroxymethylbenzene and silica (see Bayer and Jung, *Tetrahedron Lett.,* 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

Further support media amenable to the present invention include without limitation PEPS support a polyethylene (PE) film with pendant long-chain polystyrene (PS) grafts (molecular weight on the order of $10^6$, (see Berg, et al., *J. Am. Chem. Soc.,* 1989, 111, 8024 and International Patent Application WO 90/02749),). The loading capacity of the film is as high as that of a beaded matrix with the additional flexibility to accomodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwellplates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.,* 1975, 97, 6584, *Bioorg. Chem.* 1979, 8, 351, and J. C. S. Perkin I 538 (1981)).

Further support media amenable to the present invention include without limitation a composite of a resin and another material that is also substantially inert to the organic synthesis reaction conditions employed. One exemplary composite (see Scott, et al., *J. Chrom. Sci.,* 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA,* 1984, 81, 3998). A "tea bag" containing traditionally-used polymer beads. (Houghten, *Proc. Natl. Acad. Sci. USA,* 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175-178). Combining of reaction vessels via a manifold (Gorman, *Anal. Biochem.,* 1984, 136, 397). Multicolumn solid-phase synthesis (e.g., Krchnak, et al., *Int. J. Peptide Protein Res.,* 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.,* 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F.

Eckstein (ed.), Oligonucleotides and Analogues, a Practical Approach, Oxford University Press, New York (1991).

In general, the phosphorus protecting group (pg) is an alkoxy or alkylthio group or O or S having a β-eliminable group of the formula —$CH_2CH_2$-$G_w$, wherein $G_w$ is an electron-withdrawing group. Suitable examples of pg that are amenable to use in connection with the present invention include those set forth in the Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069. In general the alkyl or cyanoethyl withdrawing groups are preferred, as commercially available phosphoramidites generally incorporate either the methyl or cyanoethyl phosphorus protecting group.

The method for removal of pg depends upon the specific pg to be removed. The β-eliminable groups, such as those disclosed in the Köster et al. patents, are generally removed in a weak base solution, whereby an acidic β-hydrogen is extracted and the —$CH_2CH_2$-$G_w$ group is eliminated by rearrangement to form the corresponding acrylo-compound $CH_2$═CH-$G_w$. In contrast, an alkyl group is generally removed by nucleophilic attack on the α-carbon of the alkyl group. Such PGs are described in the Caruthers et al. patents, as cited herein.

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent," which is also considered to have the same meaning as "thiation reagent." Oxidation, unless otherwise modified, indicates introduction of oxygen or sulfur, with a concomitant increase in P oxidation state from III to V. Where it is important to indicate that an oxidizing agent introduces an oxygen into a P(III) species to make a P(V) species, the oxidizing agent will be referred to herein is "an oxygen-introducing oxidizing reagent."

Oxidizing reagents for making phosphate diester linkages (i.e. oxygen-introducing oxidizing reagents) under the phosphoramidite protocol have been described by e.g. Caruthers et al. and Köster et al., as cited herein. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Oxidizing reagents for making phosphorothioate diester linkages include phenylacetyldisulfide (PADS), as described by Cole et al. in U.S. Pat. No. 6,242,591. In some embodiments of the invention, the phosphorothioate diester and phosphate diester linkages may alternate between sugar subunits. In other embodiments of the present invention, phosphorothioate linkages alone may be employed. In some embodiments, the thiation reagent may be a dithiuram disulfides. See U.S. Pat. No. 5,166,387 for disclosure of some suitable dithiuram disulfides. It has been surprisingly found that one dithiuram disulfide may be used together with a standard capping reagent, so that capping and oxidation may be conducted in the same step. This is in contrast to standard oxidative reagents, such as Beaucage reagent, which require that capping and oxidation take place in separate steps, generally including a column wash between steps.

The 5'-protecting group bg or T' is a protecting group that is orthogonal to the protecting groups used to protect the nucleobases, and is also orthogonal, where appropriate to 2'-O-protecting groups, as well as to the 3'-linker to the solid support. In some embodiments of the invention, the 5'-protecting group is acid labile. In some embodiments according to the invention, the 5'-protecting group is selected from an optionally substituted trityl group and an optionally substituted pixyl group. In some embodiments, the pixyl group is substituted with one or more substituents selected from alkyl, alkoxy, halo, alkenyl and alkynyl groups. In some embodiments, the trityl groups are substituted with from about 1 to about 3 alkoxy groups, specifically about 1 to about 3 methoxy groups. In particular embodiments of the invention, the trityl groups are substituted with 1 or 2 methoxy groups at the 4- and (if applicable) 4'-positions. A particularly acceptable trityl group is 4,4'-dimethoxytrityl (DMT or DMTr).

In the context of the present invention, the term "reagent push" has the meaning of a volume of solvent that is substantially free of any active compound (i.e. reagent, activator, by-product, or other substance other than solvent), which volume of solvent is introduced to the column for the purpose, and with the effect, of pushing a reagent solution onto and through the column ahead of a subsequent reagent solution. A reagent push need not be an entire column volume, although in some cases it may include one or more column volumes. In some embodiments, a reagent push comprises at least the minimum volume necessary to substantially clear reagent, by-products and/or activator from a cross-section of the column immediately ahead of the front formed by the reagent solution used for the immediately subsequent synthetic step. An active compound, whether a reagent, by-product or activator, is considered substantially cleared if the concentration of the compound in a cross-section of the column at which the following reagent solution front is located, is low enough that it does not substantially affect the activity of the following reagent solution. The person skilled in the art will recognize that this the volume of solvent required for a "reagent push" will vary depending upon the solvent, the solubility in the solvent of the reagents, activators, by-products, etc., that are on the column, the amounts of reagents, activators, by-products, etc. that are to be cleared from the column, etc. It is considered within the skill of the artisan to select an appropriate volume for each reagent push, especially with an eye toward the Examples, below.

As used herein, unless "column wash" is otherwise modified, it has the same meaning as "reagent push." In some embodiments of the invention, column wash may imply that at least one column volume is permitted to pass through the column before the subsequent reagent solution is applied to the column. Where a column volume (CV) of the column wash is specified, this indicates that a volume of solvent equivalent to the interior volume of the unpacked column is used for the column wash.

In the context of the present invention, a wash solvent is a solvent containing substantially no active compound that is applied to a column between synthetic steps. A "wash step" is a step in which a wash solvent is applied to the column. Both "reagent push" and "column wash" are included within this definition of "wash step".

A wash solvent may be a pure chemical compound or a mixture of chemical compounds, the solvent being capable of dissolving an active compound.

In some embodiments according to the present invention, a wash solvent used in one of the wash steps may comprise some percentage of acetonitrile, not to exceed 50% v/v.

The sequence of capping and oxidation steps may be reversed, if desired. That is, capping may precede or follow oxidation. Also, with selection of a suitable thiation reagent, the oxidation and capping steps may be combined into a single step. For example, it has been surprisingly found that capping with acetic anhydride may be conducted in the presence of N,N'-dimethyldithiuram disulfide.

Various solvents may be used in the oxidation reaction. Suitable solvents are identified in the Caruthers et al. and Köster et al. patents, cited herein. The Cole et al. patent describes acetonitrile as a solvent for phenylacetyldisulfide. Other suitable solvents include toluene, xanthenes, dichloromethane, etc.

Reagents for cleaving an oligonucleotide from a support are set forth, for example, in the Caruthers et al. and Köster et al. patents, as cited herein. It is considered good practice to cleave oligonucleotide containing thymidine (T) nucleotides in the presence of an alkylated amine, such as triethylamine, when the phosphorus protecting group is O—$CH_2CH_2CN$, because this is now known to avoid the creation if cyanoethylated thymidine nucleotides (CNET). Avoidance of CNET adducts is described in general in U.S. Pat. No. 6,465,628, which is incorporated herein by reference, and especially the Examples in columns 20-30, which are specifically incorporated by reference.

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

The 5'-hydroxyl protecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. in the presence of dichlroacetic acid (DCA), trichloroacetic acid (TCA), or acetic acid. Removal of DMT from the support-bound oligonucleotide is generally performed with DCA (e.g. about 3 to about 10 percent DCA (v/v) in a suitable solvent. Removal of oligonucleotide after cleavage from the support is generally performed with acetic acid.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compound. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Synthetic schemes for the synthesis of the substitute internucleoside linkages described above are disclosed in: U.S. Pat. Nos. 5,466,677; 5,034,506; 5,124,047; 5,278,302; 5,321,131; 5,519,126; 4,469,863; 5,455,233; 5,214,134; 5,470,967; 5,434,257. Additional background information relating to internucleoside linkages can be found in: WO 91/08213; WO 90/15065; WO 91/15500; WO 92/20822; WO 92/20823; WO 91/15500; WO 89/12060; EP 216860; PCT/US 92/04294; PCT/US 90/03138; PCT/US 91/06855; PCT/US 92/03385; PCT/US 91/03680; U.S. application Ser. Nos. 07/990,848; 07,892,902; 07/806,710; 07/763,130; 07/690,786; Stirchak, E. P., et al., Nucleic Acid Res., 1989, 17, 6129-6141; Hewitt, J. M., et al., 1992, 11, 1661-1666; Sood, A., et al., J. Am. Chem. Soc., 1990, 112, 9000-9001; Vaseur, J. J. et al., J. Amer. Chem. Soc., 1992, 114, 4006-4007; Musichi, B., et al., J. Org. Chem., 1990, 55, 4231-4233; Reynolds, R. C., et al., J. Org. Chem., 1992, 57, 2983-2985; Mertes, M. P., et al., J. Med. Chem., 1969, 12, 154-157; Mungall, W. S., et al., J. Org. Chem., 1977, 42, 703-706; Stirchak, E. P., et al., J. Org. Chem., 1987, 52, 4202-4206; Coull, J. M., et al., Tet. Lett., 1987, 28, 745; and Wang, H., et al., Tet. Lett., 1991, 32, 7385-7388.

Phosphoramidites used in the synthesis of oligonucleotides are available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. Pat. No. RE 34,069).

Double stranded oligonucleotides, such as double-stranded RNA, may be manufactured according to methods according to the present invention, as described herein. In the case of RNA synthesis, it is necessary to protect the 2'-OH of the amidite reagent with a suitable removable protecting groups. Suitable protecting groups for 2'-OH are described in U.S. Pat. Nos. 6,008,400, 6,111,086 and 5,889,136. A particularly suitable 2'-protecting group for RNA synthesis is the ACE protecting group as described in U.S. Pat. No. 6,111,086. In some embodiments, it is considered advantageous to use a different 5'-protecting group for amidites used in RNA synthesis. Suitable 5'-protecting groups are set forth in U.S. Pat. No. 6,008,400. A particularly suitable 5'-protecting group is the trimethylsilyloxy (TMSO) group as taught in U.S. Pat. No. 6,008,400. See especially example 1, columns 10-13. The separate strands of the double stranded RNA may be separately synthesized and then annealed to form the double stranded (duplex) oligonucleotide.

Oligonucleotide Use

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

RNAse H-Dependent Antisense

One method for inhibiting specific gene expression involves using oligonucleotides or oligonucleotide analogs as "antisense" agents. Antisense technology involves directing oligonucleotides, or analogs thereof, to a specific, target messenger RNA (mRNA) sequence. The interaction of exogenous "antisense" molecules and endogenous mRNA modulates transcription by a variety of pathways. Such pathways include transcription arrest, RNAse H recruitment, and RNAi (e.g. siRNA). Antisense technology permits modulation of specific protein activity in a relatively predictable manner.

EXAMPLES

The present invention may be further understood with reference to the following, no-limiting, illustrative examples, which may be carried out by methods generally described hereinabove.

All impurities described herein were categorized as non-critical or critical based upon the products formed in the test reactions described herein.

Example 1

Synthesis of n+80 AMU Impruities

Through a combination of analytical chemistry and synthetic organic chemistry we have identified the site of modification as cytosine (or 5-methylcytosine) and to a much lesser extent adenine, residues present in the parent oligonucleotide. The structures of the cytosine (I), 5-methylcytosine (II) and adenine (III) adducts are shown below.

Structures of n+80 amu Components

I

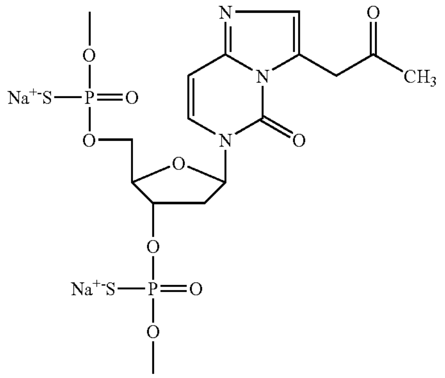

II

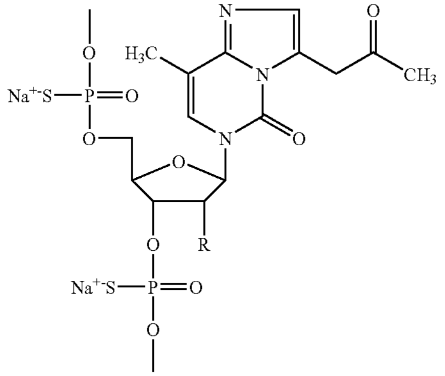

III

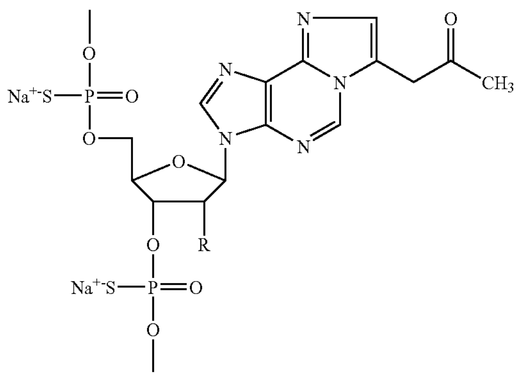

R = H or $OCH_2CH_2OCH_3$

The synthesis of compound I is described in outline in Scheme 1.
Scheme 1. Synthesis of compound I
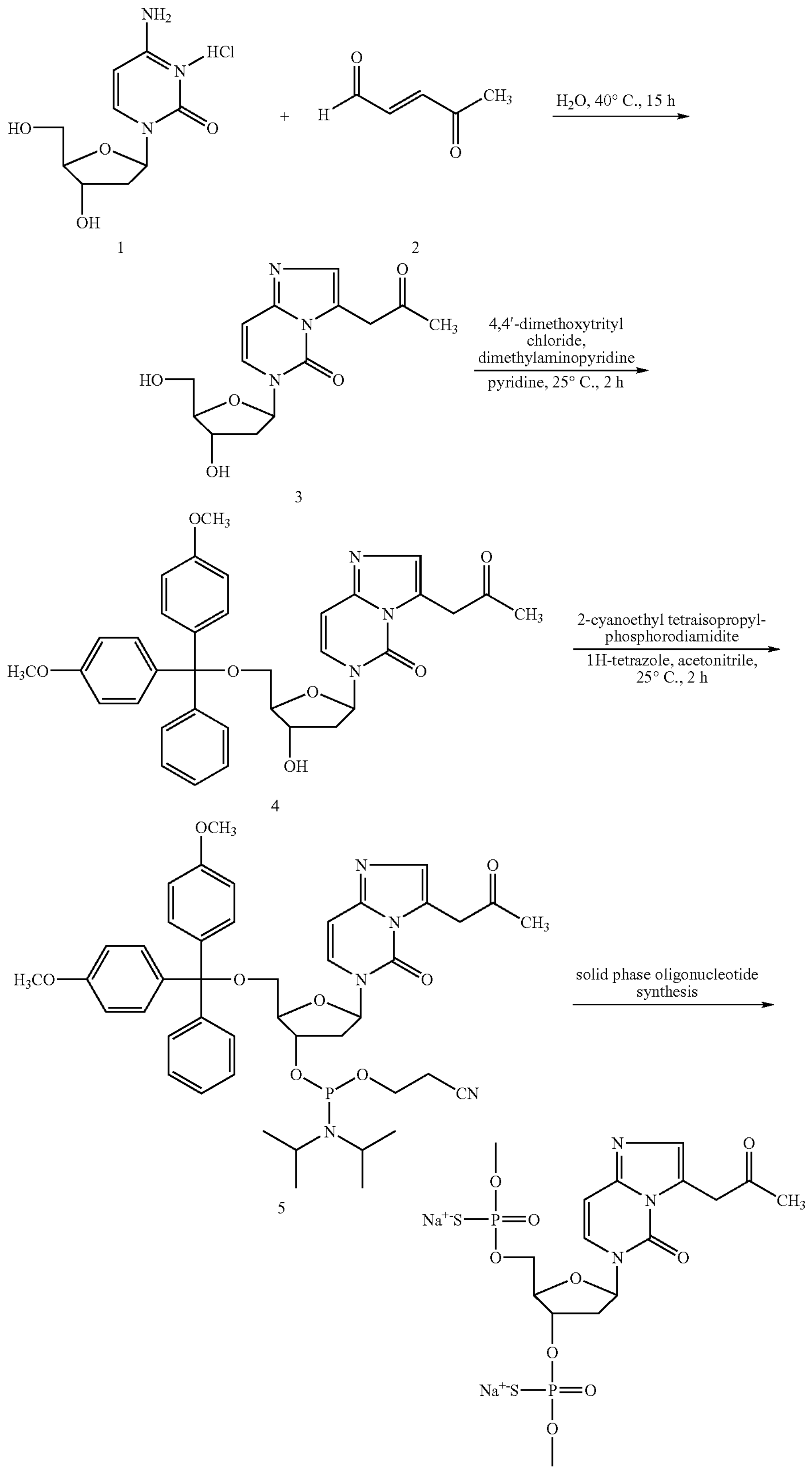
1 2 3 4 5
I Reaction of 2'-deoxycytidine hydrochloride (1) with an excess of 4-oxo-2-pentenal (2) in water at 40° C. for 15 h gave modified nucleoside 3. Protection of the 5'-hydoxy group of 3 as its 4,4'-dimethoxytrityl ether followed by phosphitylation using 2-cyanoethyl tetraisopropylphosphorodiamidite in the presence of 1H-tetrazole gave modified phosphoramidite 5. The modified cytosine residue was incorporated into phosphorothioate DNA (I) using standard solid phase oligonucleotide synthesis techniques.

Example 2

Synthesis of Λ-Mer Impurities in Phosphorothioate Oligonucleotides

The present invention provides a novel class of impurities in phosphorothioate oligonucleotides. These have been synthesized using solid phase phosphoramidite chemistry. These impurities were characterized by a variety of analytical techniques and take the general form I shown below:

Structures of λ-mer Impurities

I

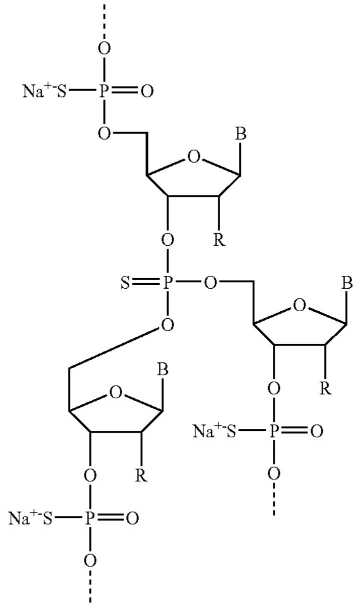

-continued

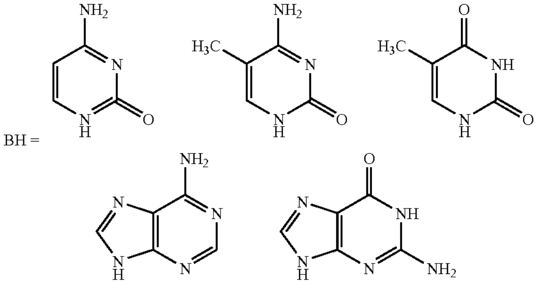

R = H or $OCH_2CH_2OCH_3$

In this family of impurities, a 5'-terminal deletion sequence is attached to a molecule of the parent sequence via a phosphorothioate triester linkage. The members of this family are distinguished from each other by the location of the triester linkage within the parent sequence. In all components, the two strands located 3' of the triester linkage are the same lengths. These components possess one 5' and two 3' ends. Drawn in the shape shown in FIG. 1 they resemble the Greek letter lambda (λ); for this reason we refer to this class of impurity as "λ-mers."

Specific λ-mers may be synthesized according to the chemistry outlined in the Scheme below.

Synthesis of λ-mers

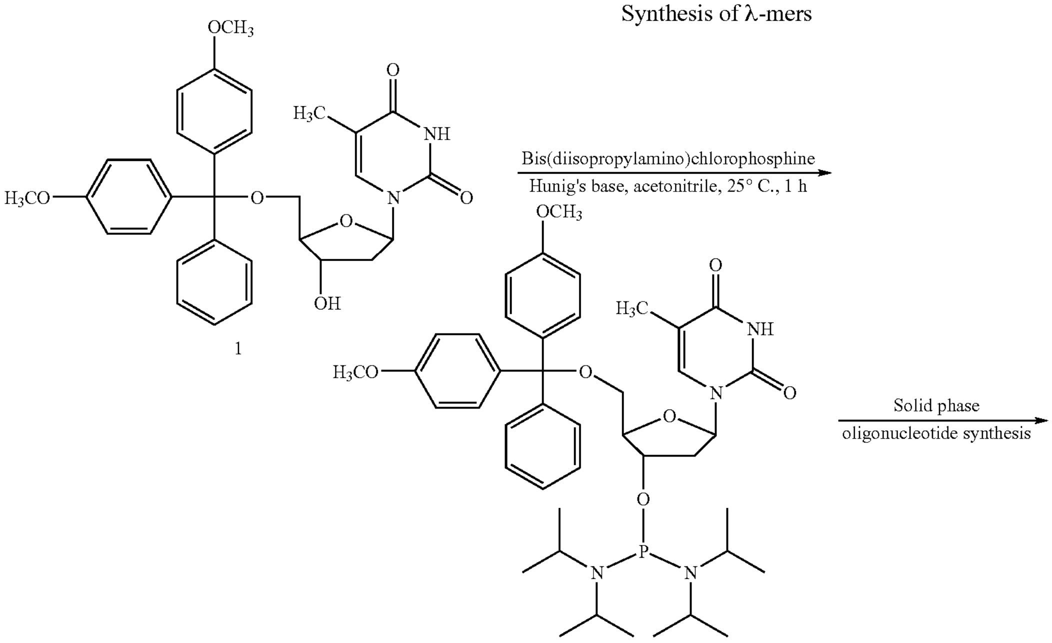

1

2

-continued
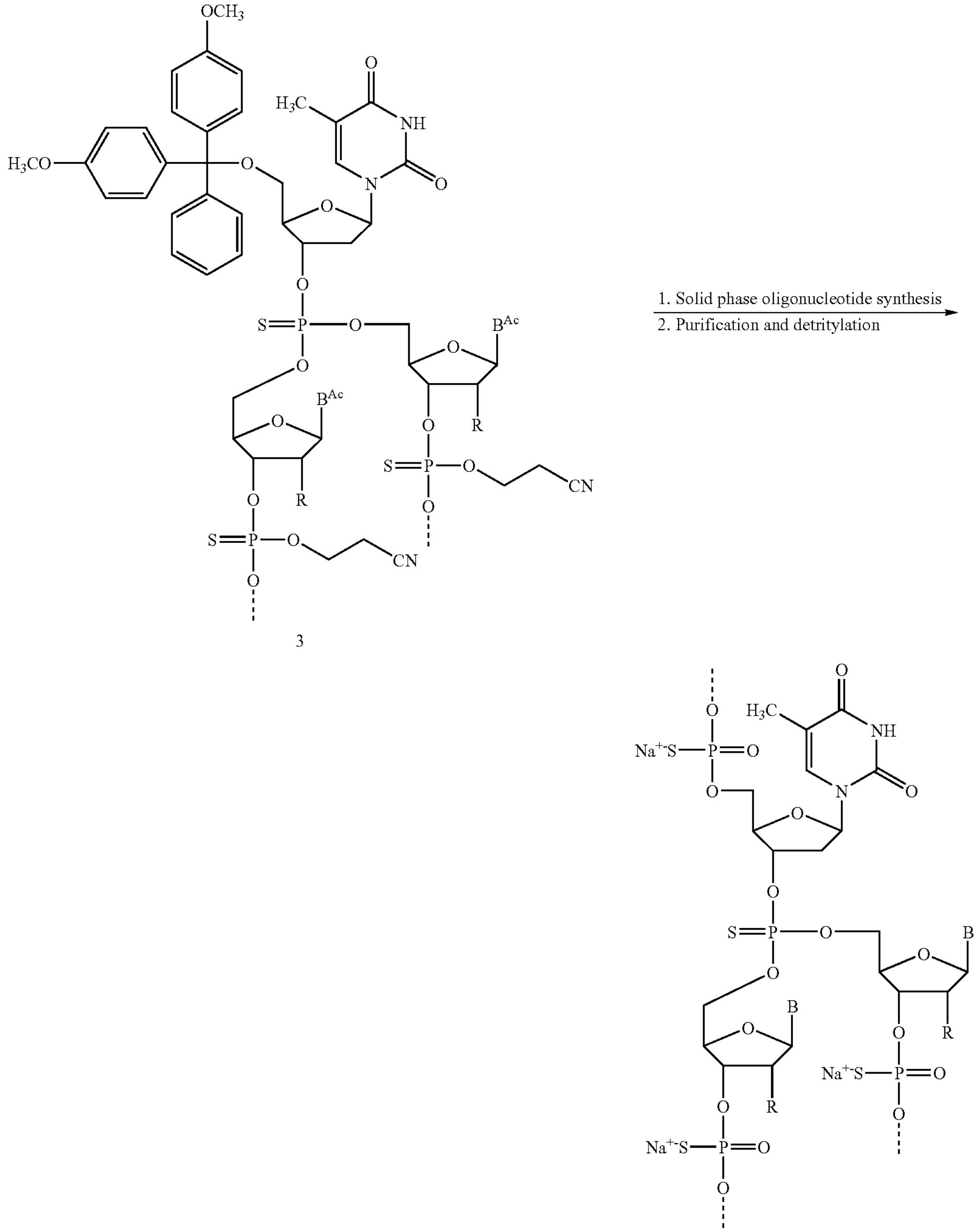
3
I
BH =
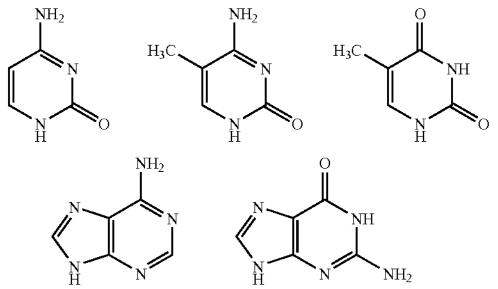
Ac = benzoyl or isobutyryl
R = H or $OCH_2CH_2OCH_3$ Reaction of 5'-O-(4,4'-dimethoxytrityl)thymidine (1) with bis(diisopropylamino)chlorophosphine in the presence of Hunig's base, gave protected thymidine bisphosphoramidite 2. Reaction of half an equivalent of 2 during one cycle of a standard solid phase oligonucleotide synthesis, gave fully protected phosphorothioate triester 3. Extension of 3 using standard solid phase oligonucleotide chemistry, followed by purification and a final deprotection step, gave λ-mer I.

Example 3

Synthesis of a Chloral Hydrate Adduct of Isis 3521 Drug Substance

Ion-pair liquid-chromatography mass spectrometry (IP-LC-MS) analysis of ISIS 3521 drug substance revealed the presence of low levels of an impurity with a molecular weight 147 amu greater than the parent compound. Evidence from other sequences suggested this impurity was almost certainly composed of a family of chloral hydrate modified oligonucleotides. In order to confirm this hypothesis, an unambiguous chemical synthesis of a member of this group of impurities was undertaken. The mass spectral properties of this material and the native impurity were identical. The chromatographic properties of the native and synthetic materials were also very similar.

The average mass spectrum of the main UV peak obtained by ion pair-liquid chromatography analysis of a typical batch of ISIS 3521 drug substance is displayed in FIG. 1, which revealed the presence of an impurity with a molecular weight of 6581.6 amu (m/z=1644.4) or 147 amu more than the parent oligonucleotide (m/z=1607.6). Extraction of the ions corresponding to the −4 charge state of the impurity and the full-length, fully-thioated component showed the former had a slightly longer retention time (data not shown). The differences in molecular weight and retention time suggested very strongly that this component was composed of a family of chloral hydrate modified oligonucleotides. In order to confirm this hypothesis, an unambiguous chemical synthesis of a member of this group of impurities was undertaken with the intention of comparing the chromatographic and mass spectral properties of the synthetic and native materials.

$^{31}P$ NMR spectra were recorded at 81 MHz on a Varian Gemini 200 spectrometer. Mass spectra of the dimer phosphoramidite were recorded using a Bruker LC 90 ion trap mass spectrometer. Oligonucleotide samples for analysis by ion pair-liquid chromatography-mass spectrometry (IP-LC-MS) were prepared at nominal concentrations of 0.1 mg/mL.

Trichloroacetaldehyde modified GT dimer (3) p-Toluene-sulphonic acid (5.6 g, 29.4 mmol) was added to a stirred solution of 3'-O-levulinylthymidine (1, 10 g, 29.4 mmols) and chloral hydrate (19.4 g, 117.5 mmol) in methylene chloride (100 mL) at room temperature. After 26 h the mixture was poured into saturated aqueous sodium hydrogen carbonate solution (200 mL). The organic layer was separated and the aqueous layer extracted with methylene chloride (100 mL). The combined organic layers were dried ($Na_2SO_4$) then filtered and the filtrate concentrated to give a colorless glass.

The crude hemiacetal 2 and 5'-O-(4,4'-dimethoxytrityl)-$N^2$-isobutyryl-2'-deoxyguanosine-2-cyanoethyl-(N,N-diisopropylamino)phosphoramidite (37.0 g, 44.1 mmol) were dissolved in dry acetonitrile (150 mL). 1H-tetrazole (10.3 g, 147 mmol) was added and the products stirred at room temperature for 90 min. Diethyldithiocarbonyl disulfide (35.6 g, 147 mmol) was added and stirring continued overnight. The mixture was concentrated and a solution of the residue in methylene chloride (500 mL) washed with saturated aqueous sodium hydrogen carbonate solution (2×200 mL), dried ($Na_2SO_4$) then filtered and the filtrate concentrated. The residue was purified by chromatography on silica gel. Combination and evaporation of the fractions eluted with chloroform-methanol (98.5:1.5 v/v) gave the desired dimer as a colorless glass (21.2 g).

Hydrazine monohydrate (5 mL, 103 mmol) was added to a stirred solution of purified dimer (11 g, 9.1 mmol) in pyridine-acetic acid (2:1 v/v, 60 mL) at 0° C. After 20 min the products were poured into ice (ca. 300 mL) and stirred until the ice melted. The precipitate was collected by filtration then dissolved in methylene chloride (200 mL). The solution was washed with saturated aqueous sodium hydrogen carbonate solution (2×100 mL), dried ($Na_2SO_4$) then filtered and the filtrate concentrated. The residue was purified by chromatography on silica gel. Combination and evaporation of the fractions eluted with chloroform-methanol (1.50 to 1:25 v/v) gave desired dimer 3 as a colorless glass (5.9 g).

Trichloroacetaldehyde modified GT dimer phosphoramidite (4) 1H-Tetrazole (0.49 g, 7 mmol) was added to a stirred solution of trichloroacetaldehyde modified GT dimer 3 (5.8 g, 5 mmol) and bisdiisopropylamino-2-cyanoethylphosphoramidite (4.5 g, 15 mmol) in dry methylene chloride (100 mL). The mixture was stirred for 30 min. at room temperature then more methylene chloride (100 mL) added. The products were extracted with washed with saturated aqueous sodium hydrogen carbonate solution (2×200 mL) and the organic layer dried ($Na_2SO_4$) then filtered and the filtrate concentrated. The residue was dissolved in methylene chloride (20 mL) and the product precipitated by the addition of hexanes (100 mL). The supernatant was discarded and the dissolution-precipitation procedure repeated twice more. The residue was dissolved in methylene chloride (20 mL) and evaporated to give the desired product 4 as a colorless glass.). $^{31}P$ NMR δ ($CDCl_3$) 65.43, 65.47, 66.48, 67.12, 67.24, 69.30, 69.33, 148.89, 149.28, 149.40, 149.73, 150.01, 150.22, 150.32. MS(ESI-MS) 1359.4 ($M+H^+$) (calc. 1358.3), for assignment of fragments see SDB Q0860-14.

Synthesis of trichloroacetaldehyde modified ISIS 3521 Synthesis was performed on an OligoPilot II DNA/RNA synthesizer using Primer HL-30 (6.3 mL). Phosphoramidites were dissolved to a concentration of 0.2 M in anhydrous acetonitrile and activated with 0.45 M solution of 1H-tetrazole in acetonitrile. Detritylation was effected by treatment with a 10% v/v solution of dichloroacetic acid in toluene and sulfurization was achieved with a 0.2 M solution of phenylacetyl disulfide in 3-picoline-acetonitrile (1:1 v/v).

After completion of synthesis, the support-bound oligonucleotide was suspended in ammonium hydroxide (60 mL) and the products heated at 60° C. for 14 h then allowed to cool to room temperature. The support was removed by filtration and washed with ethanol-water (1:1 v/v, 50 mL). The combined filtrate and washings were concentrated under vacuum to a volume of about 45 mL. The residue was purified by reversed phase HPLC using a gradient of methanol in aqueous sodium acetate. The fractions that eluted with 50% methanol were combined and evaporated to a volume of approximately 40 mL. The purified product was precipitated by the addition of cold (−20° C.) ethanol (200 mL) and isolated by centrifugation. The precipitate was dissolved in water (2 mL) and aqueous sodium acetate solution (10 mM, pH 2.9, 6 mL) added. The products incubated for 1 h at room temperature then precipitated by addition of aqueous sodium acetate (2.5 M, pH 8, 1 mL) and cold (−20° C.) ethanol (20 mL). The detritylated oligonucleotide collected by centrifugation and washed with ethanol (10 mL). The residue was dissolved in water (6 mL) and lyophilized.

Chloral hydrate modified ISIS 3521 was synthesized by incorporation of modified dimer phosphoramidite 4 into the ISIS 3521 sequence. The route used to synthesize 4 is outlined in the Scheme below:

Synthesis of Chloral Hydrate Modified Dimer Phosphoramidite

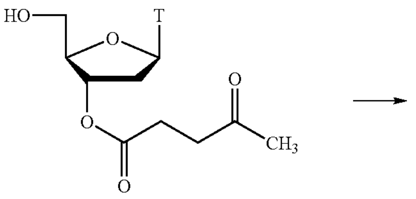

1

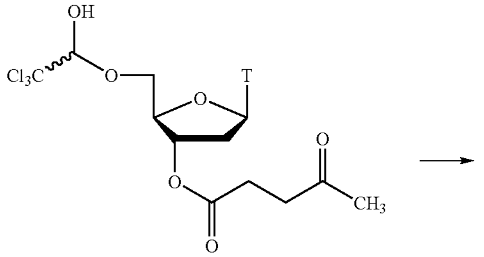

2

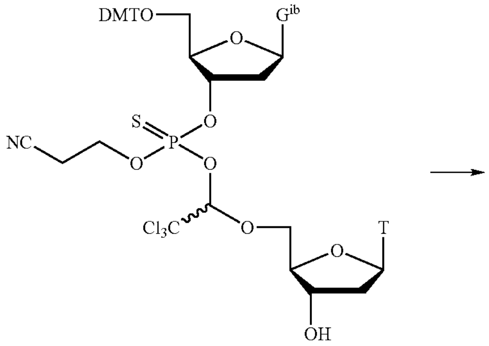

3

-continued

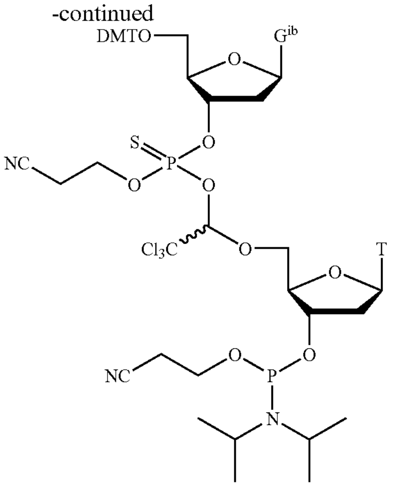

4

Treatment of 3'-O-levulinylthymidine (1) with a mixture of chloral hydrate and pTSA in methylene chloride gave hemiacetal 2. Following work-up, crude 2 was treated with 5'-O-(4,4'-dimethoxytrityl)-$N^2$-isobutyryl-2'-deoxyguanosine-2-cyanoethyl-(N,N-diisopropylamino)phosphoramidite in the presence of 1H-tetrazole. The formed phosphite triester was sulfurized in situ using an excess of diethyldithiocarbonyl disulfide and the crude product purified by chromatography. The fully protected dimer was then treated with hydrazine in pyridine-acetic acid to remove the levulinyl group and give modified dimer 3. Compound 3 was then phosphitylated in the normal fashion to give the phosphoramidite 4. $^{31}P$ NMR analysis of compound 4 gave two distinct sets of resonances centered around 67 PPM and 150 PPM confirming the presence of the internucleotide phosphorothioate triester and phosphoramidite functionalities, respectively. Further structural proof was obtained by MS/MS analysis.

In conjunction with standard solid phase oligonucleotide synthesis reagents, dimer phosphoramidite 4 was used to prepare the chloral hydrate modified ISIS 3521 sequence 5 shown in below:

Choral Hydrate Modified ISIS 3521

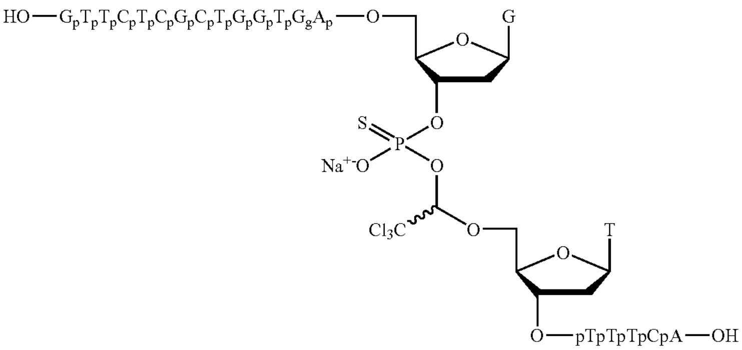

Figure 2:
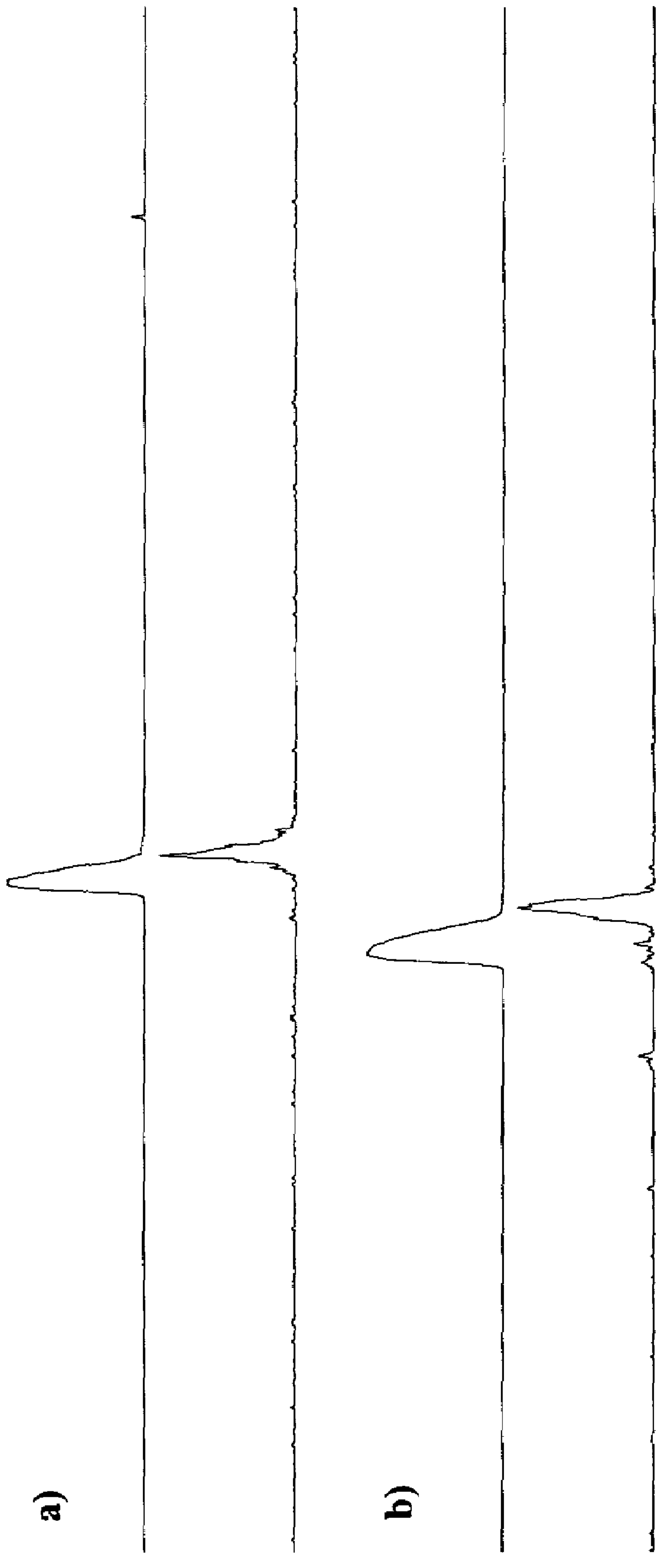
FIG. 2 shows ion chromatograms of full-length, fully-thioated species and m/z=1644.4 impurity in a) control sample, b) sample spiked with 0.5% of 5.

As expected, the most abundant mass obtained by IP-LC-MS analysis of synthetic 5 matched that of the native impurity. The chromatographic properties of synthetic 5 were then compared to those of the native impurity by spiking a sample of ISIS 3521 with the synthetic material. The spiked sample and an unspiked control were analyzed by IP-LC-MS. In each case, the ions due to the −4 charge state of the impurity and the parent oligonucleotide were extracted and integrated. The ion chromatograms obtained are shown in FIG. 2. The relative retention times of the native and synthetic impurities were 1.02 and 1.04, respectively. The reasonably close agreement of relative retention times provided support for the proposed structure. The observation that the relative retention times were not identical is probably due to the fact that the native impurity is actually composed of a group of related species, each with a modified internucleotide linkage at a different location within the sequence. Each species could exhibit slightly different chromatographic properties with the result that the reported relative retention time is an average of all components. In contrast, the synthetic material is a single sequence that elutes as a sharper peak.

Data supporting the hypothesis that the +147 amu impurity observed in ISIS 3521 drug substance is composed of a group of chloral hydrate modified oligonucleotides was presented. The mass spectral properties of a representative sequence made by unambiguous chemical synthesis and those of the native impurity were identical. The chromatographic properties of the native and synthetic materials were also very similar.

Example 4

Characterization and Synthesis of the 2n-da Impurity in Isis 3521 Drug Substance Ion-pair liquid chromatography mass spectrometry (IP-LC-MS) analysis of ISIS 3521 drug substance revealed the presence of a late-eluting impurity. The data presented in this report supports the hypothesis that the impurity is a 39-mer oligonucleotide formed by the addition of 19-mer oligonucleotides to the 5'-hydroxy and $N^6$ positions of a single 2'-deoxyadenosine residue (structure 2). Although indistinguishable at the oligonucleotide level by IP-LC-MS, an alternative structure in which the two 19-mer chains grow from the 5'- and 3'-hydroxy groups of the 3'-terminal 2'-deoxyadenosine residue (structure 1) was discounted on the basis of results obtained from model compounds.

Assignment of structure suggested a possible mechanism of formation and with it a potentially useful modification to the manufacturing process. It is hypothesized that the 2n-dA impurity arises due to loss of the $N^6$-benzoyl protecting group on the 2'-deoxyadenosine residue attached to the solid support. This allows the first phosphoramidite to couple to both the 5'-hydroxy and $N^6$ positions. If true, impurity formation should be avoided by reprotection prior to commencing synthesis. The most obvious way to achieve this would be to insert a capping step before the initial detritylation reaction thereby acetylating $N^6$ and preventing reaction at this site.

Figure 3:
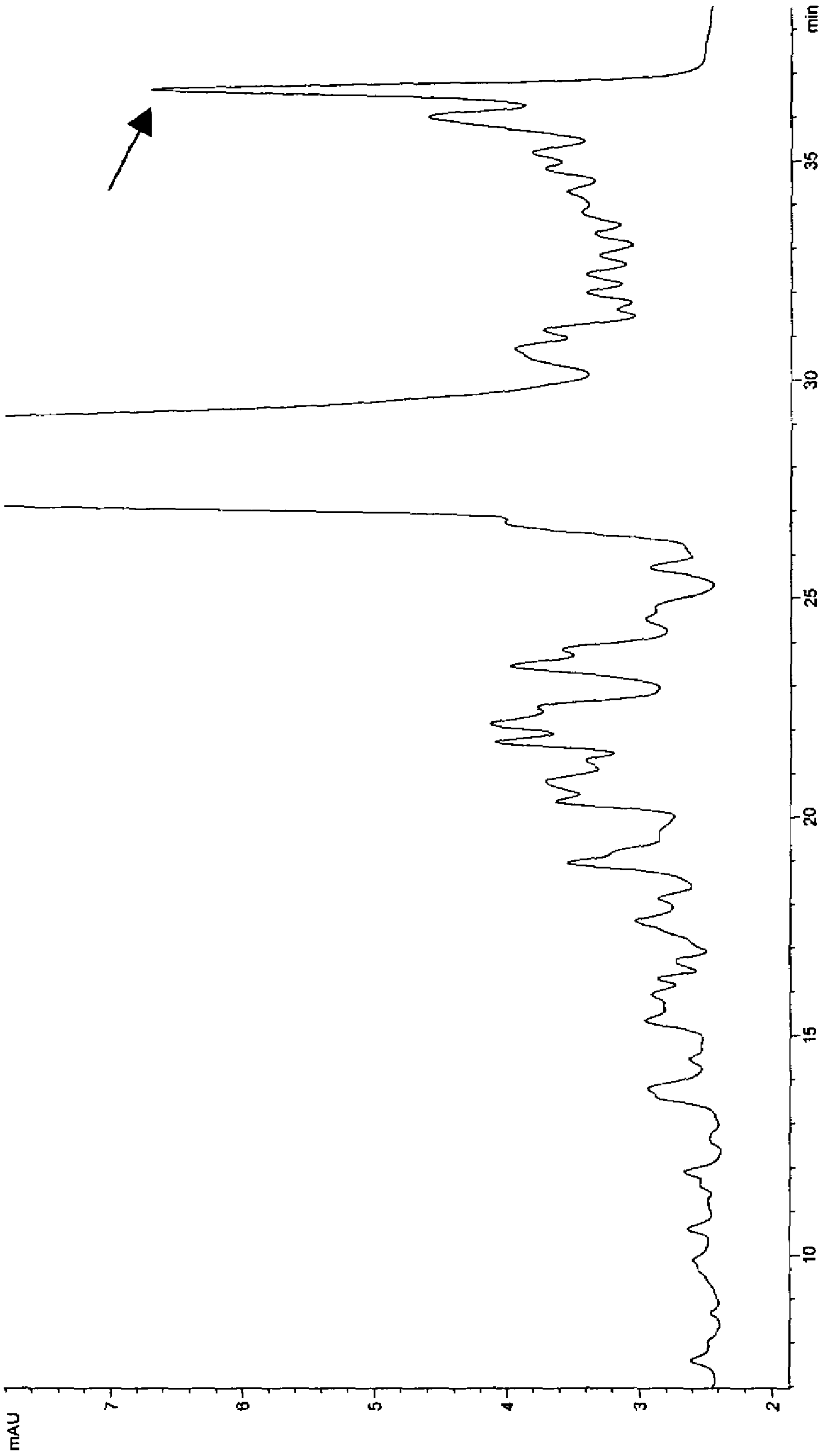
FIG. 3 shows ion pair-liquid chromatogram of ISIS 3521 drug substance.

The ion pair-liquid chromatogram of a typical batch of ISIS 3521 drug substance is shown in FIG. 3. An impurity with a relative retention time (rrt) of about 1.3 (indicated) is clearly visible as the latest eluting component in the sample.

$^1$H NMR spectra were recorded at 200 MHz on a Varian Gemini 200 spectrometer and at 400 MHz on a Varian Unity 400 spectrometer.

5'-O-$N^6$-di-(4,4'-dimethoxytrityl)-2'-deoxyadenosine-3'-O-succinate, TEA salt 5'-O-(4,4'-Dimethoxytrityl)-$N^6$-benzoyl-2'-deoxyadenosine (10 g, 15.2 mmol) was suspended in 2 M methanolic ammonia (50 mL) and the products stirred at room temperature for 16 h. Two molar methanolic methylamine (50 mL) was added and stirring continued for a further 4 h. The mixture was concentrated under reduced pressure and the residue coevaporated with dry pyridine (2×25 mL). The residue was redissolved in anhydrous pyridine (100 mL) then cooled in ice and trimethylsilyl chloride (9.5 mL, 75 mmol) added. The mixture was allowed to warm to room temperature and stirred a further hour. 4',4-Dimethoxytrityl chloride (6 g, 17.8 mmol) was added and the mixture stirred at room temperature for 20 h then cooled in ice and saturated aqueous sodium hydrogen carbonate solution (150 mL) added. The products were concentrated under reduced pressure and a solution of the residue in ethyl acetate (100 mL) washed with saturated aqueous sodium hydrogen carbonate solution (2×50 mL), dried ($Na_2SO_4$) and evaporated in vacuo. The residue was purified by chromatography on silica gel; combination and evaporation of the fractions eluted with chloroform-methanol (50:1 v/v) gave 5'-O—$N^6$-di-(4,4'-dimethoxytrityl)-2'-deoxyadenosine (7.5 g, 8.8 mmol) as a yellowish glass. Succinic anhydride (1.05 g, 10.5 mmol) and 4-dimethylaminopyridine (DMAP, 0.054 g, 0.4 mmol) were added to a stirred solution of 5'-O—$N^6$-Di-(4,4'-dimethoxytrityl)-2'-deoxyadenosine (7.5 g, 8.8 mmol) and TEA (1.5 mL, 10.5 mmol) in anhydrous methylene chloride (50 mL). The mixture was stirred for 16 h then additional succinic anhydride (0.5 g, 5 mmol) added. After a further 6 h the products were diluted with methylene chloride (100 mL) and extracted with 0.5 M triethylammonium hydrogen carbonate (TEAB, 100 mL). The organic layer was dried ($Na_2SO_4$) and concentrated under reduced pressure. The residue was purified by chromatography on silica gel, combination and evaporation of the fractions eluted with chloroform-MeOH-TEA (50:1:1 v/v/v) gave the title compound (6.8 g, 6.4 mmol) as a colorless glass. $^1$H NMR δ $[(CD)_3]_2SO$ 8.28 (1H, s, $H_2$), 7.80 (1H, s, $H_8$), 7.33-7.13 (19H, m, aromatic and NH), 6.80 (m, 8H, aromatic), 6.37 (1H, m, $H_{1'}$), 5.38 (1H, m, $H_{3'}$), 4.18 (1H, m, $H_{4'}$), 3.70 (12H, s, $OCH_3$), 3.2 and 2.55-2.40 (14H, m, $H_{5'}$, $H_{2'}$, $C\underline{H}_2$—$C\underline{H}_2$, $CH_2N$), 0.80 (9H, t, $NCH_2C\underline{H}_3$)

3',5'-di-O-(4,4'-dimethoxytrityl)-2'-deoxyadenosine-N-6-1, 12-dodecanedioate, TEA salt. Hunig's base (11.0 g, 85 mmol) was added to a stirred solution of 1,12-dodecanedioyl dichloride (6.8 g, 25.6 mmol) and 1-H-tetrazole (3.6 g, 51.2 mmol) in THF (60 ml) at 0° C. After 1 h a solution of 3',5'-di-O-4,4'-dimethoxytrityl-2'-deoxyadenosine (7.3 g, 8.5 mmol) in THF (40 ml) added. The mixture was allowed to warm to room temperature. Stirring was continued for a further 18 h at 25° C. The solution was cooled to 0° C., 1 M TEAB (pH 7, 5 ml) added and the solvent removed in vacuo. A solution of the residue in $CH_2Cl_2$ (150 ml) was washed with 1 M TEAB (pH 7, 2×50 ml), then dried ($Na_2SO_4$) and evaporated. The residue was purified by chromatography on silica gel, combination and evaporation of the fractions eluted with $CHCl_3$-MeOH-TEA (98.5:1.5:1, v/v/v) gave the title compound (3.9 g, 3.3 mmol, 39%) as a colorless glass. $^1$H NMR δ ($CDCl_3$) 9.18 (1H, s, br, NH), 8.64 (1H, s, $H_2$), 8.04 (1H, s, $H_8$), 7.11-7.42 (18H, m, aromatic), 6.70-6.78 (8H, m, aromatic), 6.49 (1H, m, $H_{1'}$), 4.42 (1H, m, $H_{3'}$), 4.13 (1H, m, $H_{4'}$), 3.75 (12H, s, $OCH_3$), 3.20 (1H, m, $H_{5'}$), 3.03 (1H, m, $H_{5'}$), 2.80 (6H, q, J=7.2, $NC\underline{H}_2$), 2.20-2.40 (5H, m, $H_{2'}$, C(O)C$\underline{H}_2$×2), 2.01 (1H, m, $H_{2'}$), 1.26-1.90 (16H, m, C$\underline{H}_2$×8), 1.14 (9H, t, J=7.2, $NCH_2C\underline{H}_3$)

General procedure for loading support. Nucleoside dodecanoate or succinate (7 or 10, 0.3 mmol), O-benzotriazol-1-yl-N,N,N',N'-tetramethyluronium hexafluorophosphate (HBTU, 0.91 g, 2.4 mmol), Hunig's base (0.62 g, 4.8 mmol), DMAP (0.07 g, 0.6 mmol) and amino derivatised Primer™ support HL 30 (6 g) were shaken together in $CH_3CN$ (25 mL) for 1 h at 25° C. The support was collected by filtration, washed with MeOH (2×25 mL), $Et_2O$ (2×25 mL) and $CH_3CN$ (2×25 mL) then resuspended in a mixture of acetic anhydride-pyridine-$CH_3CN$ (2:5:5 v/v/v, 10 mL) and NMI-acetonitrile (1:5 v/v, 10 mL) and the products shaken at 25° C. for 1 to 2 h. The support was collected, washed with pyridine, MeOH and $Et_2O$ then dried by suction. The loading of support 8 was estimated at 32 mmol/g. The loading of support 11 was estimated at 21 mmol/g.

Synthesis of d(CpA) P═S Synthesis was performed on an OligoPilot II DNA/RNA synthesizer using Primer 200™ support. 2'-deoxycytidine phosphoramidite was dissolved to a concentration of 0.2 M in anhydrous acetonitrile and activated with 0.45 M solution of 1-H-tetrazole in acetonitrile. Detritylation was effected by treatment with a 3% v/v solution of dichloroacetic acid in toluene and sulfurization was achieved with a 0.2 M solution of phenylacetyl disulfide in 3-picoline-acetonitrile (1:1 v/v).

After completion of synthesis, the support-bound material was suspended in ammonium hydroxide (100 mL). The products were heated at 55° C. for 8 h then cooled to room temperature. The support was removed by filtration and the filtrate concentrated to dryness under reduced pressure.

Synthesis of trimers 3 and 4 Compounds 3 and 4 were synthesized in a similar fashion to d(CpA) P═S using solid supports 8 and 11, respectively.

Synthesis of Oligonucleotide 1 Synthesis was performed on an OligoPilot II DNA/RNA synthesizer using solid support 8 (3.8 g). Phosphoramidites were dissolved to a concentration of 0.2 M in anhydrous acetonitrile and activated with 0.45 M solution of 1-H-tetrazole in acetonitrile. Detritylation was effected by treatment with a 10% v/v solution of dichloroacetic acid in toluene and sulfurization was achieved with a 0.2 M solution of phenylacetyl disulfide in 3-picoline-acetonitrile (1:1 v/v).

After completion of synthesis, the support-bound oligonucleotide was suspended in ammonium hydroxide (150 mL) and the products heated at 65° C. for 8 h then allowed to cool to room temperature. The support was removed by filtration and washed with a 1:1 v/v solution of ethanol and water (100 mL). The combined filtrate and washings were concentrated under vacuum to a volume of about 40 mL. The residue was purified by reversed phase HPLC using a gradient of methanol in aqueous sodium acetate. The fractions that eluted with 50% methanol were combined and evaporated to a volume of approximately 100 mL. The purified product was precipitated by the addition of cold (−20° C.) ethanol (500 mL) and isolated by centrifugation. The precipitate was dissolved in aqueous sodium acetate solution (10 mM, pH 3, 10 mL) and the products incubated for 1 h at room temperature. Aqueous sodium acetate (2.5 M, pH 8, 1 mL) was added and the detritylated oligonucleotide collected by centrifugation following precipitation with cold ethanol (50 mL). The product was washed with ethanol (20 mL) then dissolved in water (5 mL) and lyophilized.

Synthesis of Oligonucleotide 2 Solid support 11 (6 g) was suspended in a 10% v/v solution of dichloroacetic acid in toluene (100 mL). After 15 min the support was collected by filtration and washed with acetonitrile (2×100 mL). The detritylated support (1.9 g) was then used to synthesize compound 2. Synthesis was performed on an OligoPilot II DNA/RNA synthesizer. Phosphoramidites were dissolved to a concentration of 0.2 M in anhydrous acetonitrile and activated with 0.45 M solution of 1-H-tetrazole in acetonitrile. Detritylation was effected by treatment with a 3% v/v solution of dichloroacetic acid in toluene and sulfurization was achieved with a 0.2 M solution of phenylacetyl disulfide in 3-picoline-acetonitrile (1:1 v/v). after completion of synthesis, the support-bound oligonucleotide was suspended in triethylamine-acetonitrile (1:1 v/v, 100 ml) and the mixture incubated at room temperature for 4 h. the supernatant was discarded and the support resuspended in ammonium hydroxide (150 ml). the products were heated at 55° C. for 8 h then allowed to cool to room temperature. the support was removed by filtration and washed with a 1:1 v/v solution of ethanol and water (100 ml). the combined filtrate and washings were concentrated under vacuum to a volume of about 40 ml. a small amount of material was purified by ion-pair liquid chromatography (see nb q0861 page 77 for details). The product containing fractions were combined and evaporated. the residue was dissolved in water (0.2 ml) and the dna precipitated by the addition of aqueous sodium acetate (2.5 m, ph 8, 0.05 ml) and cold ethanol (ca. 1.3 ml). The product was isolated by centrifugation. the precipitate was dissolved in water (0.05 ml), aqueous sodium acetate solution (10 mm, ph 3, 0.2 ml) added and the products incubated for 1 h at room temperature. aqueous sodium acetate (2.5 m, ph 8, 0.02 ml) was added and the detritylated oligonucleotide collected by centrifugation following precipitation with cold ethanol (ca 1.3 ml).

Figure 4:
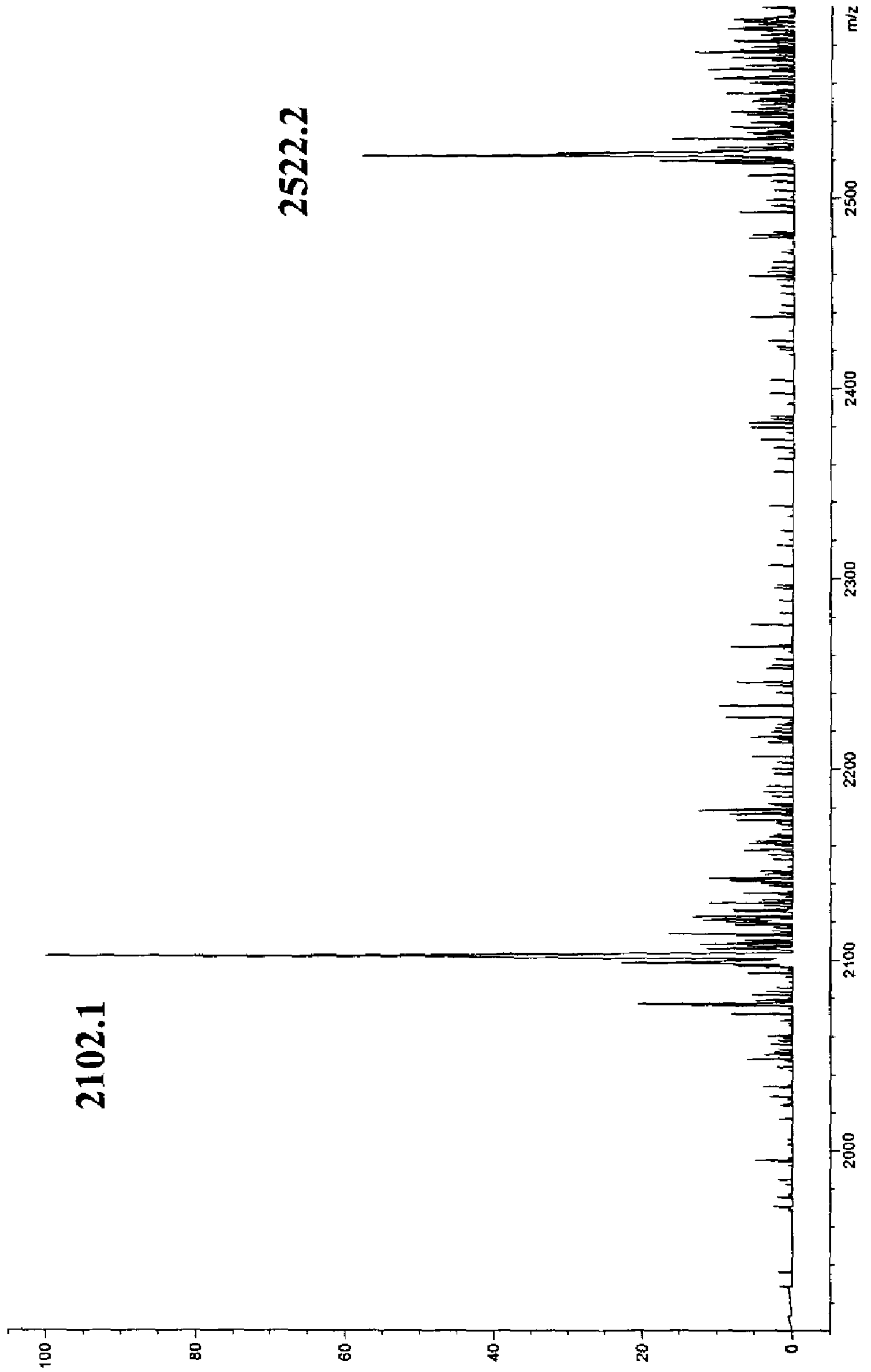
FIG. 4 shows an average mass spectrum of RRT=1.3 impurity.

Analysis of oligonucleotide samples Samples for analysis were prepared by diluting stock solutions to an approximate total oligonucleotide concentration of 0.1 mg/mL in water. The samples were analyzed according to the conditions described in AM-00141 with the following modifications:

Analysis of trimer and dimer samples Samples for analysis were prepared by diluting stock solutions to an approximate total oligonucleotide concentration of 0.1 mg/mL in water. The samples were analyzed by IP-LC-MS under the following conditions:

The average mass spectrum of the RRT=1.3 impurity is shown in FIG. 4, and showed two distinct peaks at m/z=2522.2 and 2102.1. Deconvolution indicated that these peaks were due to the −5 and −6 charge states, respectively of a single component with an estimated molecular weight of 12618. This result immediately suggested compounds 1 and 2 as possible structures.

1

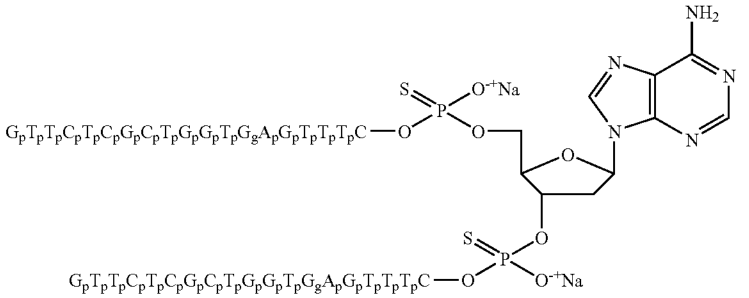

2

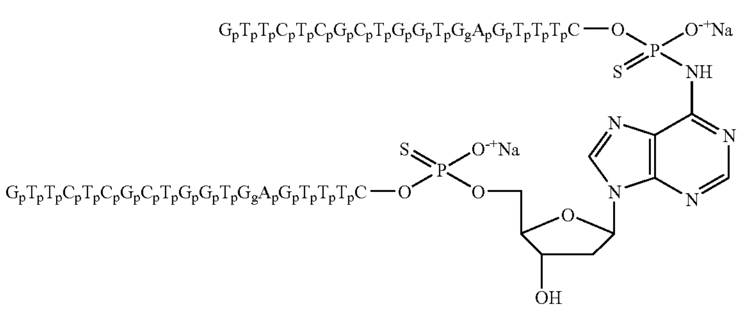

Compounds 1 and 2 are derived structurally from the parent oligonucleotide by removing the 3'-terminal 2'-deoxyadenosine residue from one molecule and attaching the remainder to another molecule of the parent sequence. Probable sites of attachment for the second chain were thought to be the 3'-hydroxyl (compound 1) and $N^6$-amino (compound 2) functionalities of the 3'-terminal 2'-deoxyadenosine residue. Compounds 1 and 2 each contain 39 base residues or two times as many the full-length sequence less one 3'-terminal 2'deoxyadenosine and were therefore termed “2n-dA.”

To provide evidence for the correctness of structures 1 or 2, we decided to synthesize both by unambiguous routes and compare the chromatographic and mass spectral properties of the synthetic materials with those of the native impurity. We were, however, concerned that due to the structural similarity of 1 and 2 a comparison at the oligonucleotide stage would not allow an unambiguous structural assignment of the native impurity. It was therefore decided in addition, to synthesize compounds 3 and 4 by the routes shown in Schemes 1 and 2. The synthetic materials would then be compared to the native 2n-dA impurity that we assumed would form by performing a single addition of 2'-deoxycytidine phosphoramidite to 2'-deoxyadenosine derivatised support. We anticipated that the much smaller molecular weight of compounds 3 and 4 would greatly facilitate any comparison of chromatographic and mass spectral properties and allow us to make a definitive structural assignment of the impurity in the drug substance. The synthesis of compound 3 is shown in outline in Scheme 1.

Scheme 1. Synthesis of 2n-dA, 3

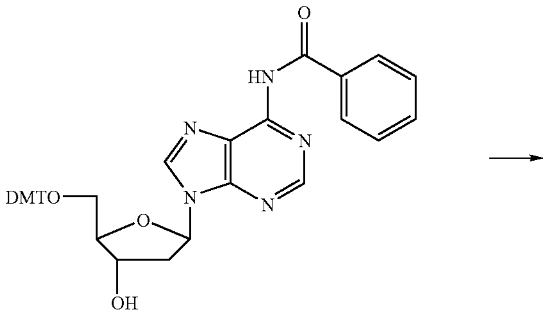

5

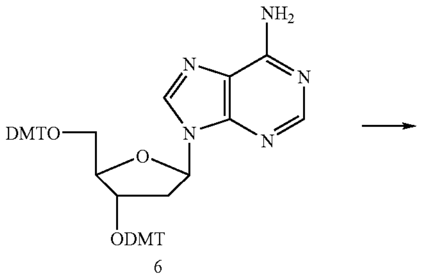

6

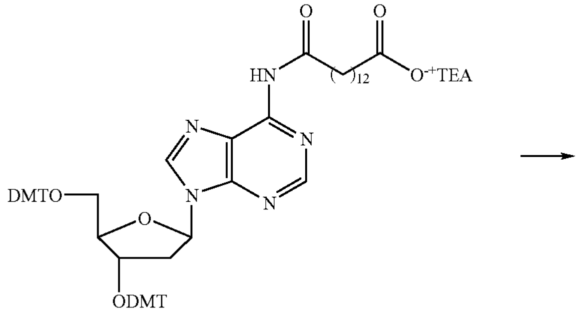

7

-continued

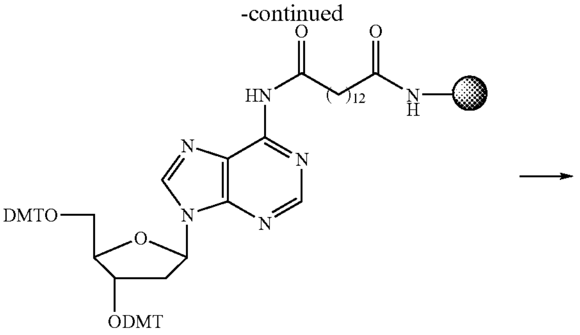

8

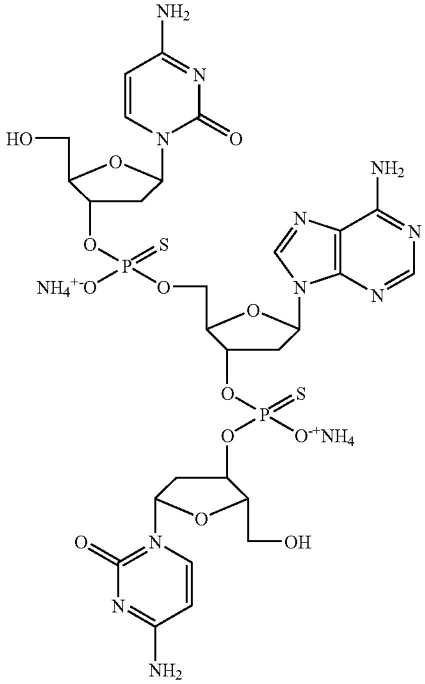

3

Synthesis of compound 3 began by treatment of commercially available 5'-O-(4,4'-dimethoxytrityl)-N-[6]-benzoyl-2'-deoxyadenosine (5) with 4,4'-dimethoxytrityl chloride. The fully protected nucleoside was then treated with 2M methanolic methylamine to give 3',5'-di-O-(4,4'-dimethoxytrityl)-2'-deoxyadenosine (6). Compound 6 was then treated with dodecanedioyl dichloride in the presence of tetrazole and Hunig's base to give half-ester 7 after purification. A suspension of 7, HBTU, Hunig's base, DMAP and Primer™ support HL 30 in acetonitrile were shaken together for 1 h to give derivatised support 8 after washing and capping. The loading of the support was estimated at 32 mmol/g. An automated DNA synthesizer was used to elongate support 8 by coupling 2'-deoxycytidine phosphoramidite in the standard fashion. Finally, deprotection with ammonium hydroxide gave desired trimer 3.

Similar chemistry was used to synthesize trimer 4. The route used is outlined in Scheme 2

Scheme 2. Synthesis of 2n-dA, 4.

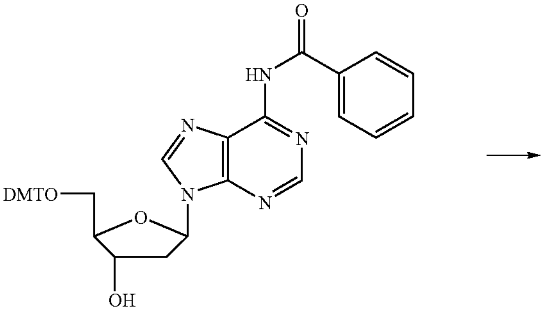

5

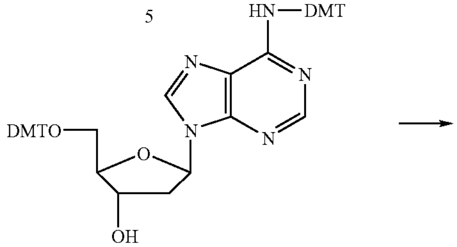

9

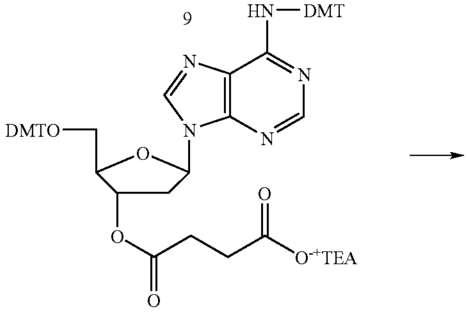

10

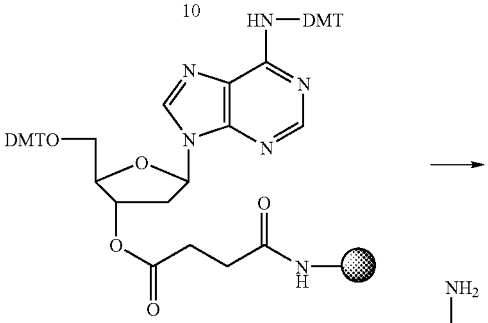

11

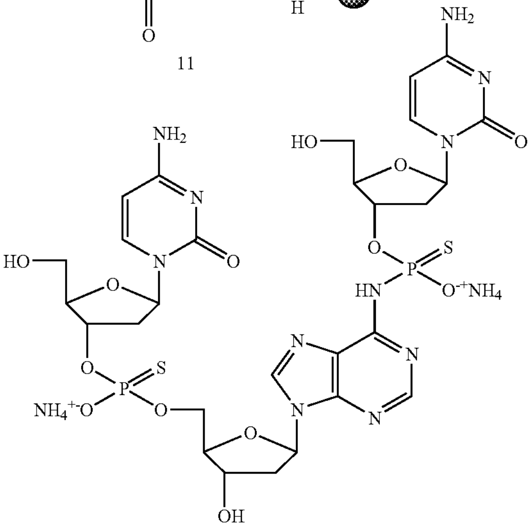

4

Synthesis of compound 4 began by treatment of 5'-O-(4,4'-dimethoxytrityl)-$N^6$-benzoyl-2'-deoxyadenosine (5) with 2M methanolic methylamine to remove the benzoyl group. The crude products were dissolved in pyridine and treated with trimethylsilyl chloride then 4,4'-dimethoxytrityl chloride. 5'-O-$N^6$-di-(4,4'-dimethoxytrityl)-2'-deoxyadenosine (9) was isolated following work-up and purification. Compound 9 was converted into its succinate half ester 10 and loaded onto Primer™ support HL 30 in the normal fashion. The loading was estimated at 21 umol/g. Derivatised support 11 was detritylated by treatment with 10% DCA in toluene for 15 minutes. An extended detritylation time was required to remove the 4,4'-dimethoxytrityl group from the exocyclic amino group. Detritylated support was converted to trimer 4 by standard solid phase oligonucleotide chemistry.

In addition to trimer 3 and 4, solid supports 8 and 11 were also used to synthesize full-length 2n-dA sequences 1 and 2, respectively. The sequences were assembled using standard techniques. The crude products were purified by reversed phase HPLC or IP-LC and detritylated with acidic sodium acetate solution.

To provide a sample containing authentic 2n-dA to which trimers 3 and 4 could be compared, a final synthesis was performed using 2'-deoxyadenosine derivatised Primer™ support HL 30 support. A single addition of 2'-deoxycytidine phosphoramidite was made and the material deprotected and isolated in the normal fashion.

Figure 5:
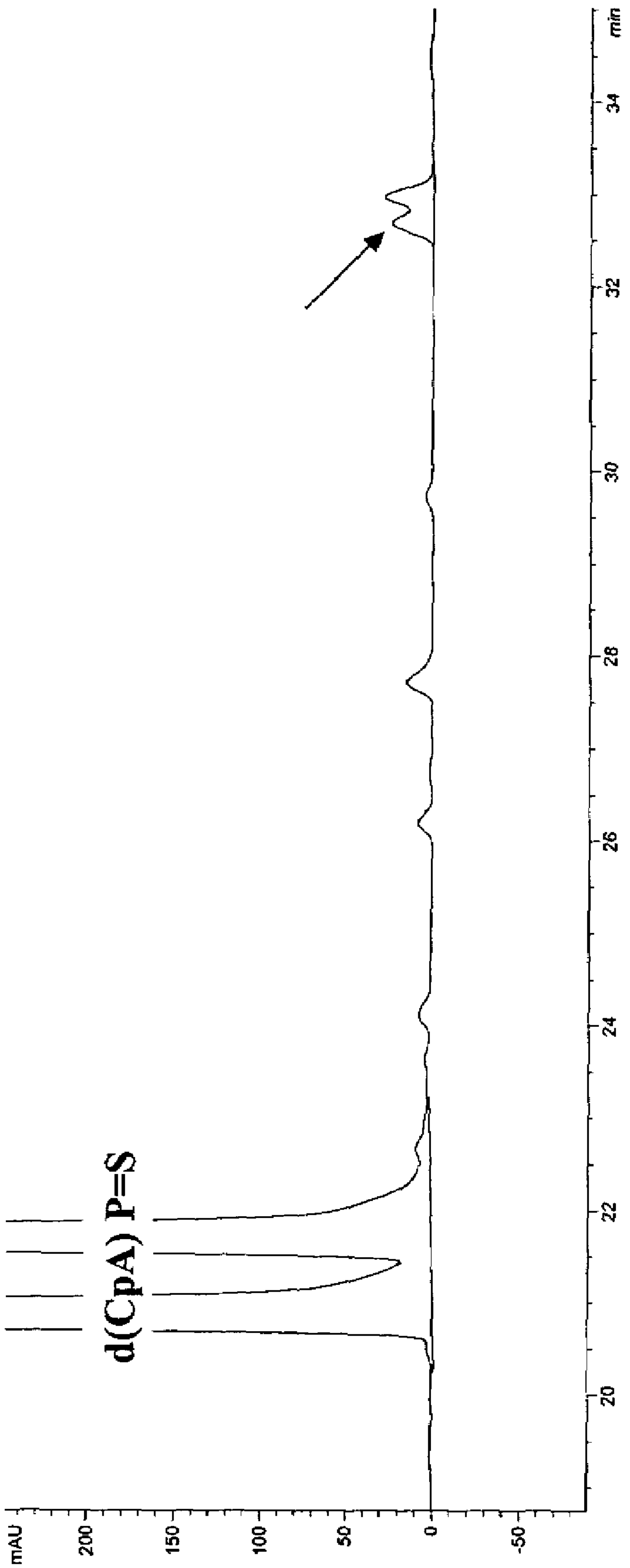
FIG. 5 shows an IP-LC-UV chromatogram of d(CpA) P═S.

The products obtained by coupling 2'-deoxycytidine phosphoramidite to standard 2'-deoxyadenosine derivatised Primer™ support HL 30 support, (d(CpA) P═S), were analyzed by IP-LC-MS, shown in FIG. 5.

Figure 6:
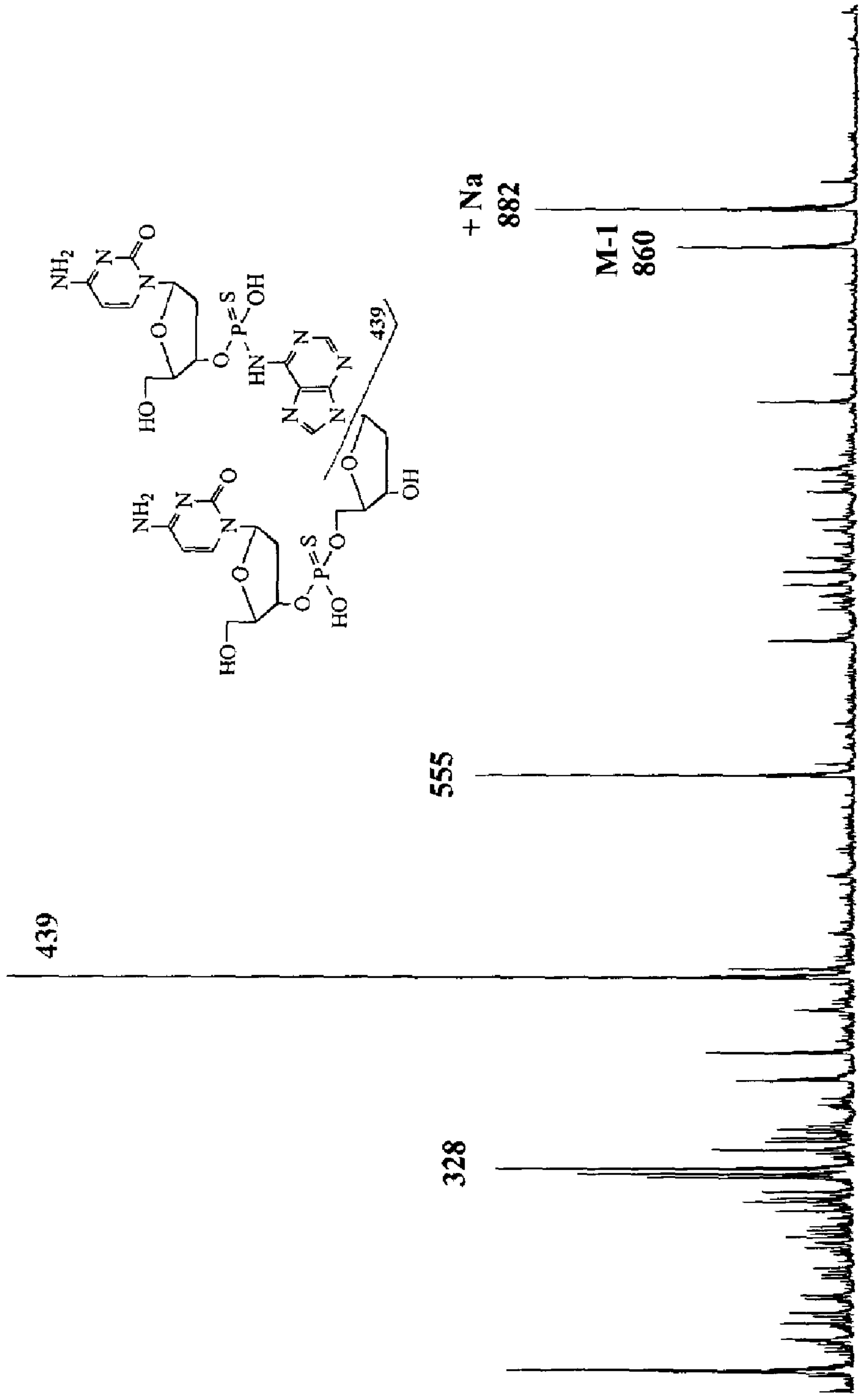
FIG. 6 shows an average mass spectrum of late-eluting peaks in d(CpA) P═S.

In addition to the expected diastereoisomers of the parent dinucleoside phosphorothioate diester d(CpA) P═S, a pair of later-eluting peaks (indicated by the arrow) was observed. Integration of the chromatogram indicated that these peaks accounted for about 1% of the total UV area. The average mass spectrum under these peaks is shown in FIG. 6. The molecular weight of these components was identical to that calculated for trimers 3 and 4 (861 amu) thus supporting their assignment as the 2n-dA species of d(CpA) P═S. Interestingly this analysis also suggested that trimer 4 was a better candidate than trimer 3. Further consideration of the average mass spectrum showed the presence of a 439-amu fragment that was thought to arise from cleavage of the glycosidic bond shown. This fragment was considered specific for trimer 4.

Figure 7:
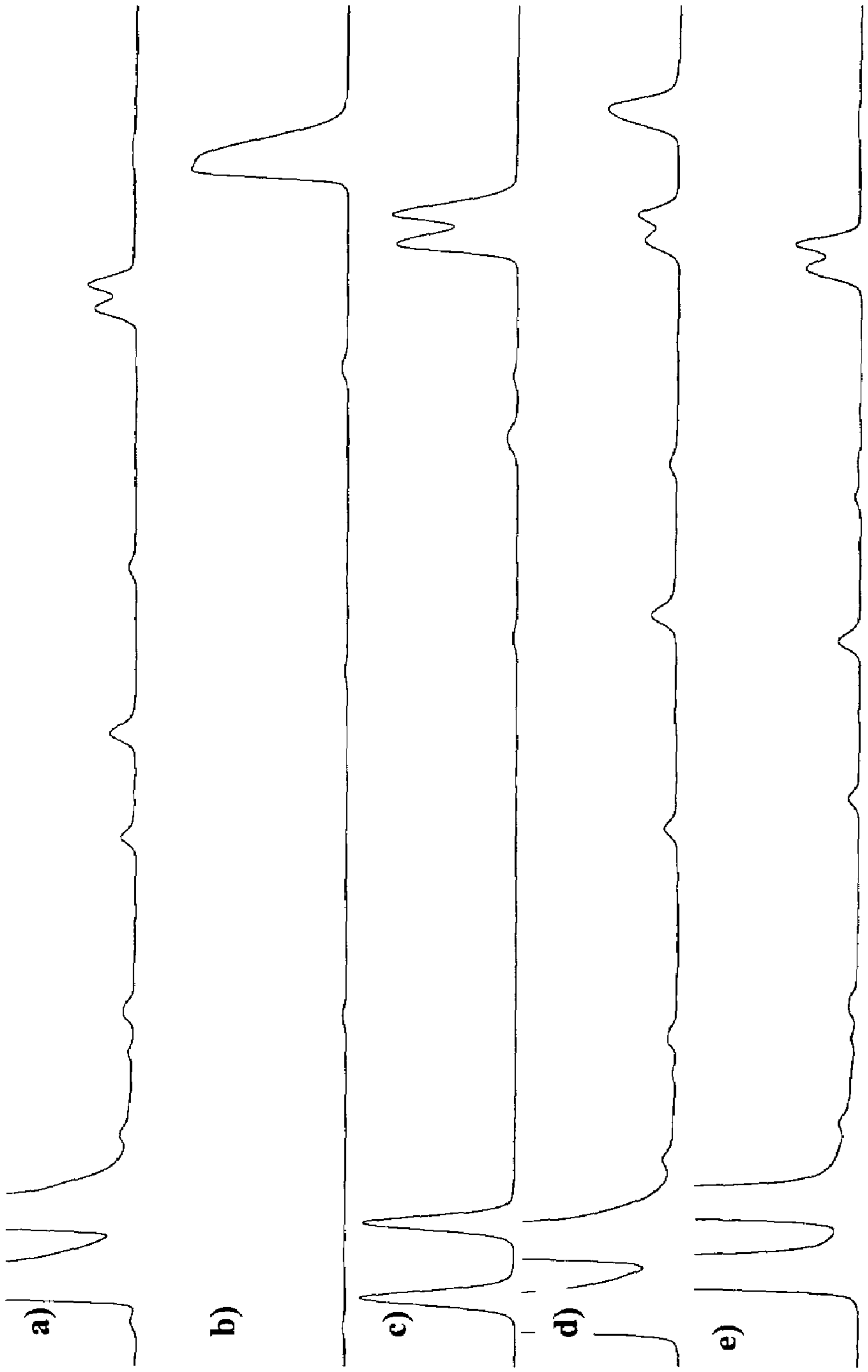
FIG. 7 shows UV chromatograms of a) d(CpA) P═S, b) 3, c) 4, d) d(CpA) P═S+3, e) d(CpA) P═S+4.
Figure 8:
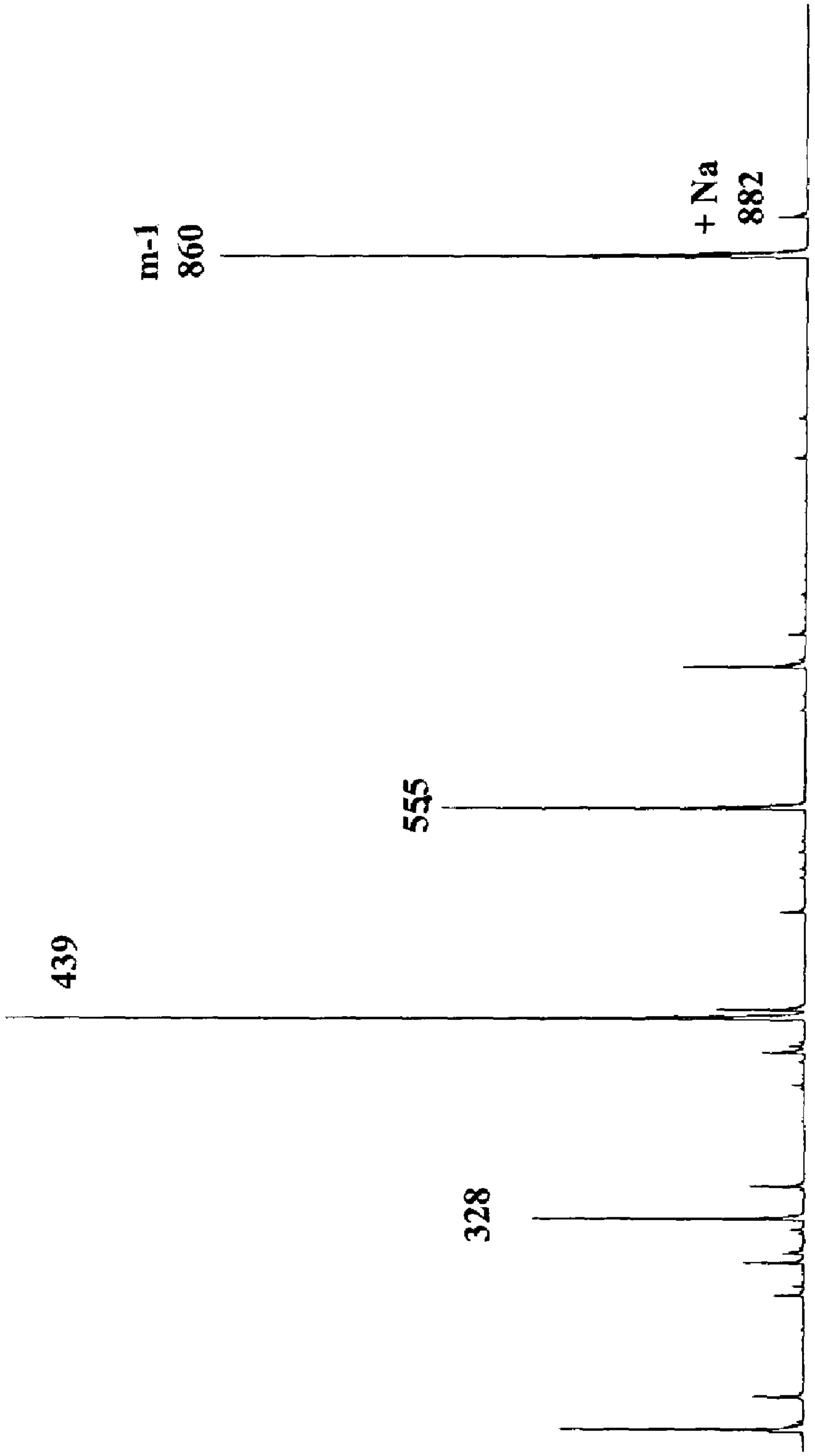
FIG. 8 shows an average mass spectrum of trimer 4 (late eluting peaks).

To confirm the structure of the native 2n-dA species in the sample of d(CpA) P═S, the chromatographic and mass spectral properties of the native impurity were compared to those of trimers 3 and 4. The UV chromatograms obtained by IP-LC-MS analysis of d(CpA) P═S, 3, 4 and of samples of d(CpA) P═S spiked with both timers are shown in FIG. 7. Panel b of FIG. 7, shows that trimer 3 eluted as a rather broad peak with a relative retention time (RRT) slightly longer than that of the native 2n-dA impurity in d(CpA) P═S (panel a). Spiking a small amount of 3 into d(CpA) P═S (panel d) confirmed that the native impurity and 3 had different retention times. In contrast, analysis of trimer 4 (panel c) showed the presence of two late eluting peaks that appeared to have an identical RRT as the native 2n-dA impurity. Interestingly, compound 4 was only about 50% pure by UV. Analysis of a sample of d(CpA) P═S spiked with a small amount of 4 (panel e) confirmed that the native impurity and 4 had identical retention times. Final structural confirmation was obtained by inspection of the average mass spectrum taken across the two late eluting peaks of trimer 4, shown in FIG. 8. The mass spectrum obtained was identical with that of native 2n-dA contained in d(CpA) P═S confirming the structure of the native impurity as trimer 4.

Figure 9:
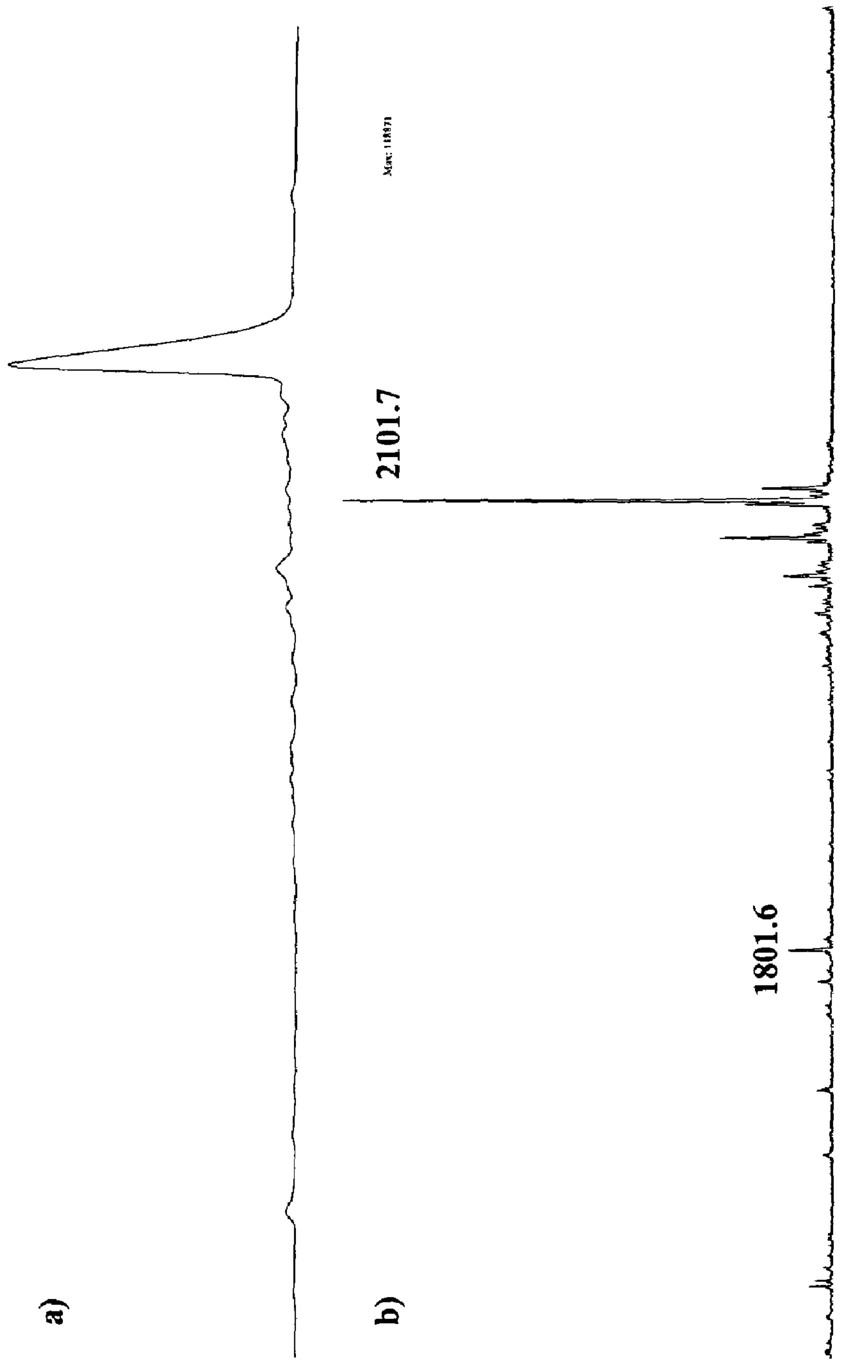
FIG. 9 shows an IP-LC-MS analysis of 1. Panel a) UV Chromatogram, b) average mass spectrum of main peak
Figure 10:
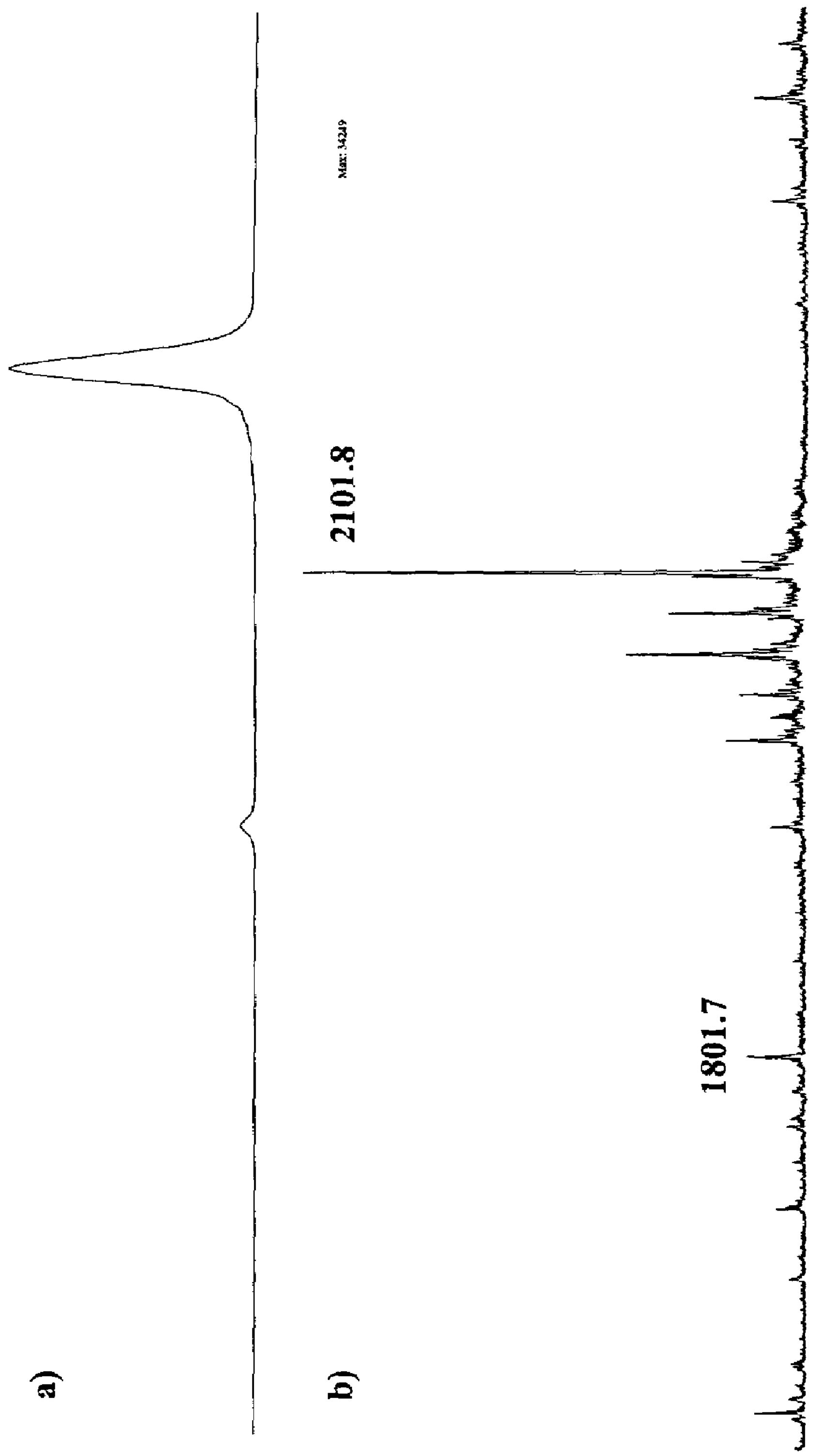
FIG. 10 shows an IP-LC-MS analysis of 2. Panel a) UV chromatogram, b) average mass spectrum of main peak

Confirmation that the structure of the native impurity in ISIS 3521 as that drawn for compound 2 was done by comparing the chromatographic and mass spectral properties of the native impurity with those of an unambiguously synthesized sample. The results of IP-LC-MS analysis of synthetic 1 and 2 are shown in FIGS. 9 and 10, respectively.

The mass spectra confirmed that compounds 1 and 2 both had the same mass as the native impurity in ISIS 3521. Inspection of the UV chromatograms indicated that 1 and 2 eluted at approximately the same retention time as the native impurity. To confirm coelution, we prepared and analyzed samples of ISIS 3521 drug substance spiked with approximately 1% of each compound. Another sample containing a 1:1 mixture of 1 and 2 was also analyzed. The resulting UV chromatograms are shown in FIG. 11.

Figure 11:
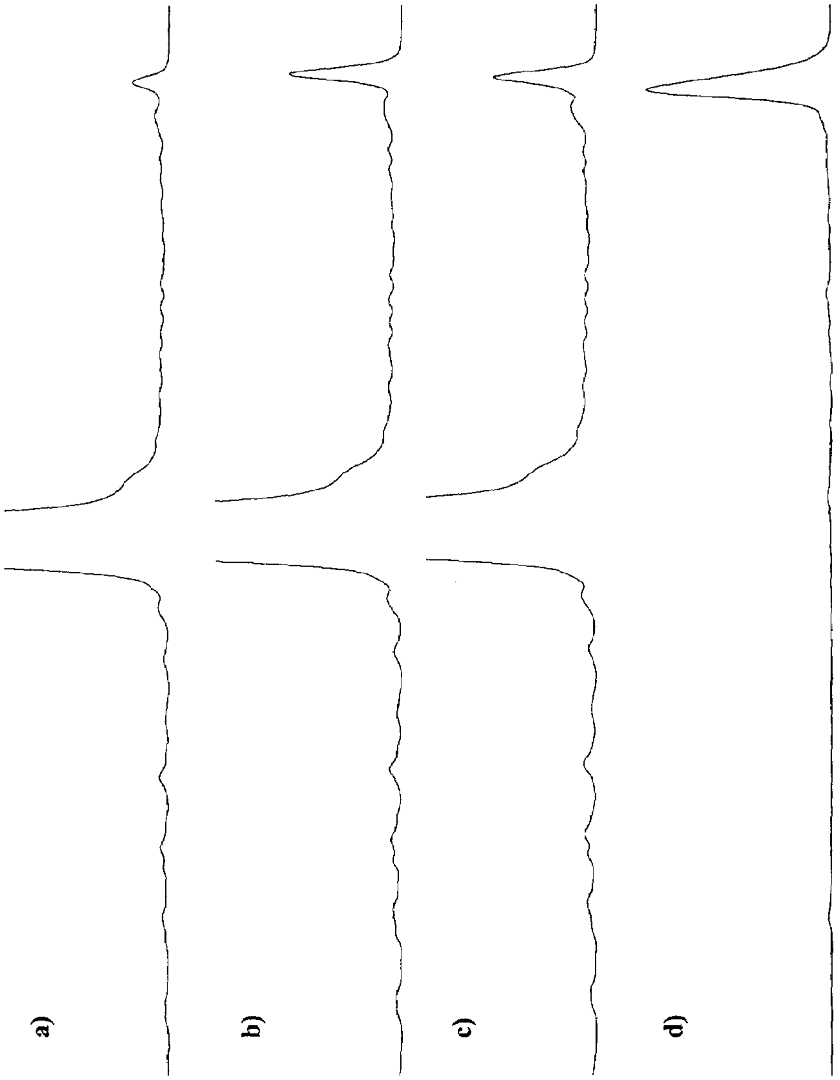
FIG. 11 shows an IP-LC-UV analysis of a) ISIS 3521 drug substance, b) ISIS 3521 drug substance spiked with 1% of 1, c) ISIS 3521 drug substance spiked with 1% of 2 and d) 1:1 mixture of 1 and 2.

Integration of the chromatogram in panel a of FIG. 11, showed that the drug substance contained about 0.8% of the late eluting impurity. As expected addition of either 1 or 2 lead to an increase in peak area of about 1% (panels b and c, in FIG. 11). Analysis of the 1:1 mixture of 1 and 2 (panel d) showed that these compounds are not separated by the IP-LC method. These results confirmed our earlier suspicion that differentiation between the alternative structures proposed for the native impurity in the drug substance would be very difficult by the existing methodology. The data obtained on timers 3 and 4 however, suggest very strongly that the native impurity in ISIS 3521 drug substance has the structure shown in 2.

The data presented above supports the hypothesis that the late eluting impurity is a 39-mer oligonucleotide formed by the addition of 19-mer oligonucleotides to the 5'-hydroxy and $N^6$ positions of a single 2'-deoxyadenosine residue (structure 2). Although indistinguishable at the oligonucleotide level by IP-LC-MS, an alternative structure in which the two 19-mer chains grow from the 5'- and 3'-hydroxy groups of the 3'-terminal 2'-deoxyadenosine residue (structure 1) was discounted on the basis of results obtained from model compounds.

Assignment of structure suggested a possible mechanism of formation and with it a potentially useful modification to the manufacturing process. It is hypothesized that the 2n-dA impurity arises due to loss of the $N^6$-benzoyl protecting group on the 2'-deoxyadenosine residue attached to the solid support. This allows the first phosphoramidite to couple to both the 5'-hydroxy and $N^6$ positions. If true, impurity formation should be avoided by reprotection prior to commencing synthesis. The most obvious way to achieve this would be to insert a capping step before the initial detritylation reaction thereby acetylating $N^6$ and preventing reaction at this site.

Example 5

Synthesis of Bis-amidite Impurities

A) Ethylene bis-(2-cyanoethyl diisopropylphosphoramidite)

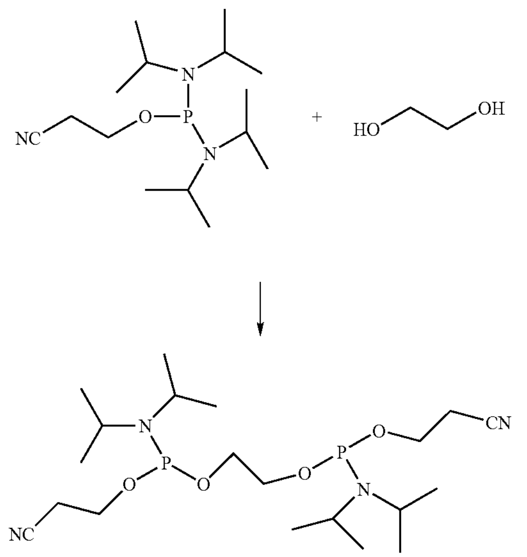

To ethylene glycol (31 g) in N,N-dimethylformamide (DMF) (300 ml) was added 2-cyanoethyl tetraisopropylphosphorodiamidite (360 g) and tetrazole (30 g). The reaction was stirred for 4 hours at room temperature. Water (200 ml) was added and the mixture was extracted with hexane (500 ml). The aqueous layer was diluted with toluene (300 ml) and washed with water (3×300 ml). The organic layer was evaporated to give an oil (101 g). The crude product was used without further purification.

B) General Procedure for the Preparation of Type I Impurities

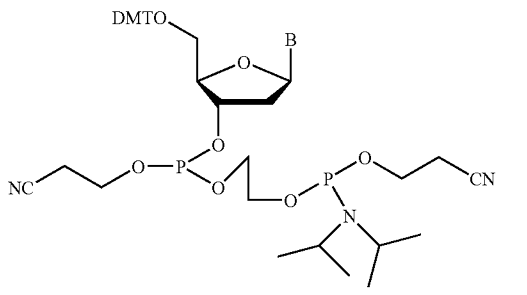

5'-O-Dimethoxytrityl nucleoside (10 mmol) and the ethylene bis-(2-cyanoethyl diisopropylphosphoramidite) (17 g) were dissolved in acetonitrile (50 ml). Tetrazole (1 g) was added and the mixture was stirred at room temperature for 30 min. The reaction mixture was diluted with toluene (50 ml), washed with brine (5%, 100 ml) and evaporated. The residue was purified by column chromatography on silica gel to give the desired product as a colorless gum (ca. 5 g).

C) 2-(tert-Butyldiphenylsilyloxy)ethyl 2-cyanoethyl diisopropylphosphoramidite

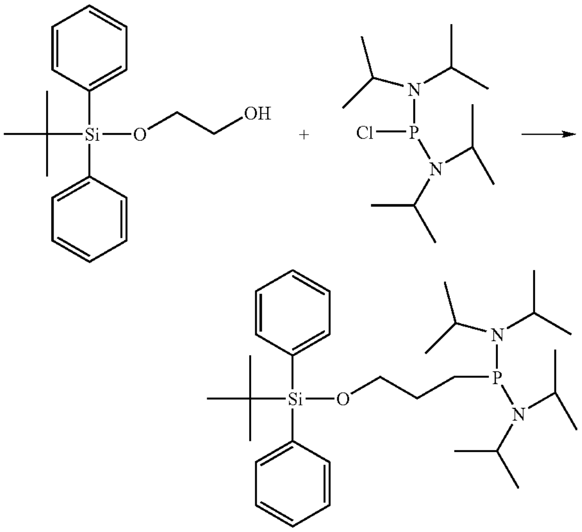

To the solution of 2-(tert-Butyldiphenylsilyloxy)ethanol (120 g) and ethyl diisopropylamine (100 g) in acetonitrile (500 ml) was added tetraisopropylchlorophosphorodiamidite (120 g). The mixture was stirred at room temperature for 2 hours and was then diluted with toluene. The mixture was washed with water (2×500 ml) and evaporated to give an oil (198 g). The crude product was used in the next step without further purification.

D) General Procedure for the Synthesis of the Type II Impurities

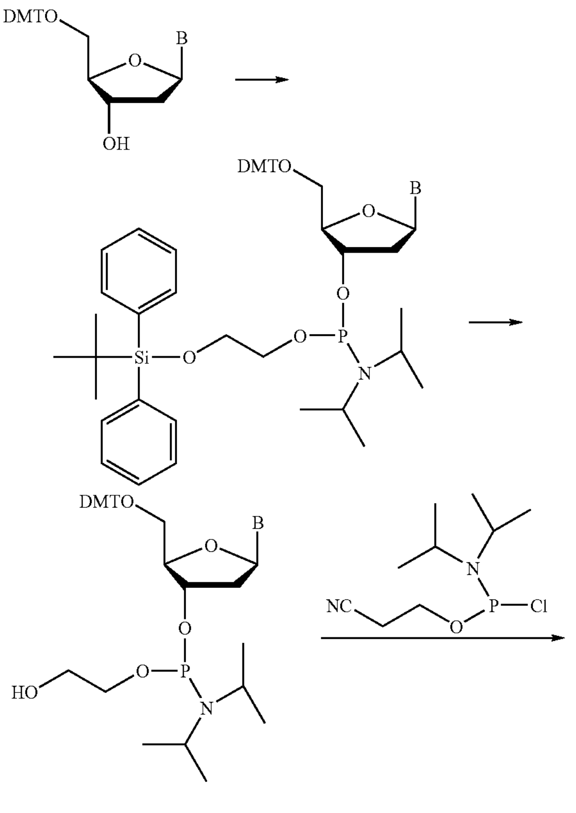

-continued

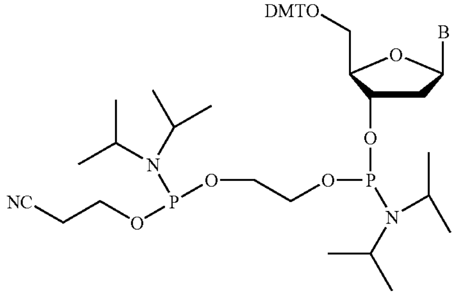

5'-O-Dimethoxytrityl nucleoside (10 mmol) and the 2-(tert-Butyldiphenylsilyloxy)ethyl 2-cyanoethyl diisopropylphosphoramidite (15 g) were dissolved in DMF (30 ml). Tetrazole (0.5 g) was added and the mixture was stirred at room temperature for 3 hours. The reaction mixture was diluted with toluene (50 ml), washed with brine (5%, 100 ml) and evaporated. The residue was dissolved in acetonitrile (50 ml) and triethylamine (10 ml). Tetrabutylammonium fluoride (8 g) was added and the mixture was stirred at for 2 hours. The mixture was diluted with toluene (100 ml), washed with water (2×100 ml) and evaporated. The residue was dissolved in toluene (50 ml). Ethyl diisopropylamine (10 ml) and cyanoethyl chlorophosphoramidite (4 ml) were added. After 20 min, the mixture was washed with water (100 ml) and evaporated. The residue was purified by column chromatography on silica gel to give the desired product as a colorless solid (ca. 5 g).

E) Ethylene bis-tetraisopropylphosphorodiamidite

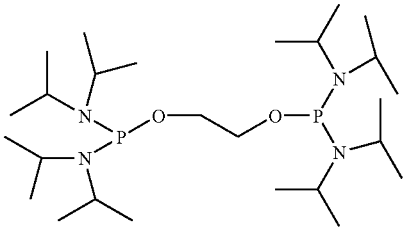

Phosphorus trichloride (218 ml) was added to a solution of diisopropylamine (2.1 L), hexane (5 L) and acetonitrile (0.5 L) and the mixture was stirred for 2 hours at room temperature. Ethylene glycol (62 g) was added and the mixture was stirred for 1 hour. The mixture was washed with water (4 L) and was evaporated to give an oil (305 g).

F) General Procedure for the Preparation of Type III Impurities

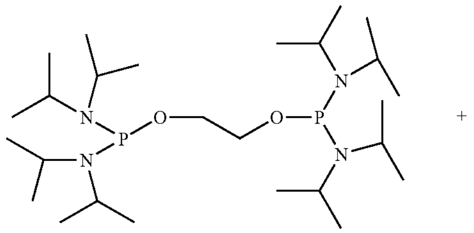

-continued

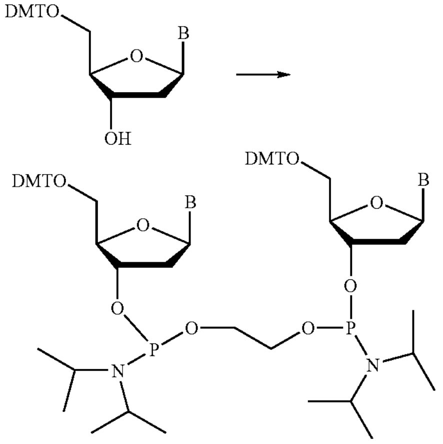

5'-O-Dimethoxytrityl nucleoside (40 mmol) and the ethylene bis-tetraisopropylphosphoramidite (10 g) were dissolved in DMF (50 ml). Tetrazole (1.4 g) was added and the mixture was stirred at room temperature for 4 hours. The reaction mixture was diluted with toluene (200 ml), washed with water (100 ml) and evaporated. The residue was purified by column chromatography on silica gel to give the desired product as a colorless solid (about 5 g).

Example 6

Synthesis and Characterization of Model Compounds Made With Critical O-ethyl Amidite Impurities A n+140 amu impurity was identified having the structure:

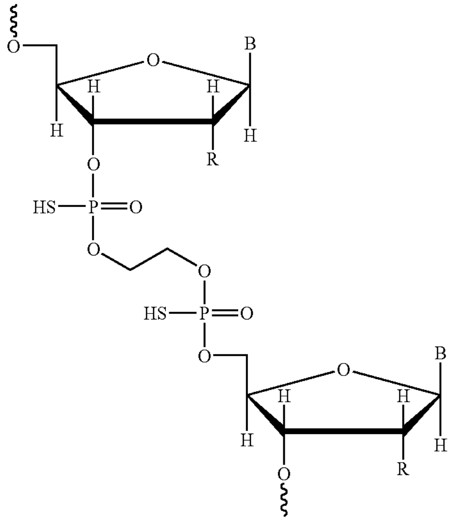

From in depth analysis of several batches of deoxy phosphoramidites three types amidite impurities were discovered that contained an additional O-ethyl phosphorous moiety. These structures are supported by their mass spectral fragmentation patterns. The structures for these three impurities are shown below. These compounds where synthesized with all four bases and used as authentics in the development and validation of an LC\MS method to asses amidite purity. The thymine version of each type of impurity was used in a model reaction to synthesize a twelve-mer in order to determine what kinds of products are produced. As impurity XI produced a complicated mixture of products, a four-mer using T-XI was also synthesized on a slightly larger scale.
Amiditoethyl Impurities
pdN-(CE-amiditoethyl)-phosphite: X
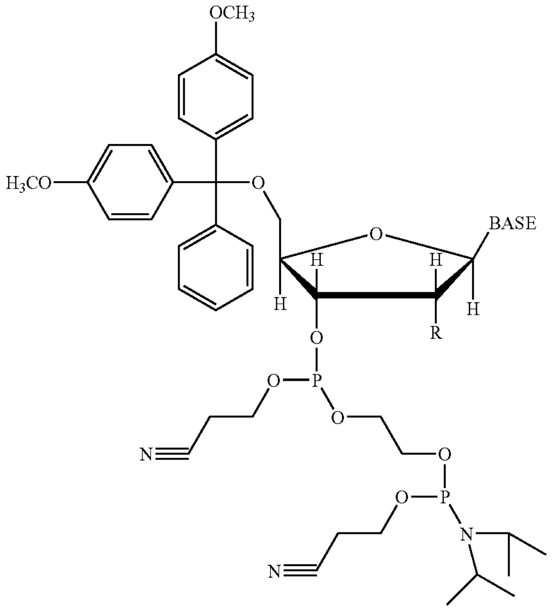
pdN-amiditoethyl-amidite: XI
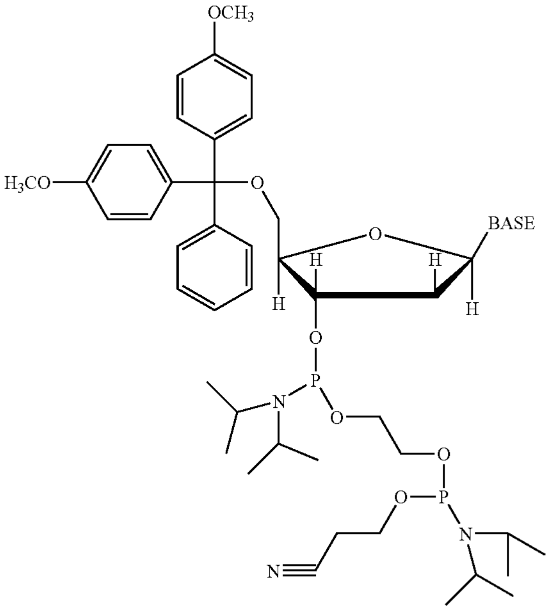
pdN-amiditoethyl-pdN-amidite: XVIII
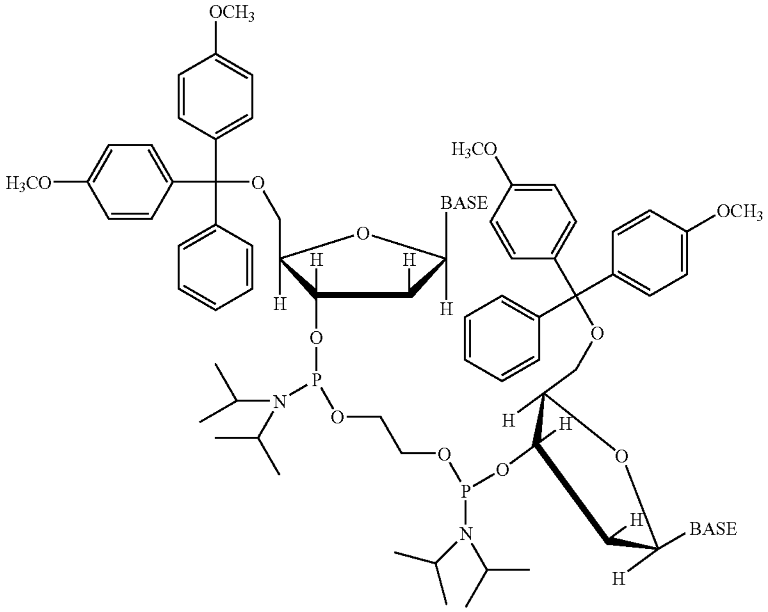

Oligonucleotide samples for analysis by ion pair-liquid chromatography-mass spectrometry (IP-LC-MS) were prepared at nominal concentrations of 0.1 mg/mL and analyzed according to the conditions described herein.

Synthesis of O-ethyl Modified Amidites

Synthesis of O-ethyl modified oligonucleotides Synthesis was performed on an Applied Biosystems 394 DNA/RNA synthesizer at the 1 μM scale using thymine loaded cpg columns from Glen Research and at the 10 μM scale using thymine loaded cpg from Cruachem. T-phosphoramidites and O-ethyl authentic impurities were dissolved to a concentration of 0.1 M in anhydrous acetonitrile and activated with 0.45 M solution of 1H-tetrazole in acetonitrile. Detritylation was effected by treatment with a 3% solution of trichloroacetic acid in DCM and sulfurization was achieved with a 0.2 M solution of phenylacetyl disulfide in 3-picoline-acetonitrile (1:1 v/v). After completion of synthesis, the support-bound oligonucleotide was dried with argon then suspended in ammonium hydroxide (1 ml) for 3.5 hours. The support was removed by filtration and washed with ethanol-water (1:1 v/v, 2 mL). The combined filtrate and washings were concentrated under vacuum to a volume of about 1 mL. Oligonucleotide concentrations were measured by UV absorbance. Authentic amidite impurities X, XI, and XVIII were each incorporated into a poly T twelve-mer at the tenth base from the 3' end on the 1 μM scale. A poly T twelve-mer control was also made. These four sequences were synthesized in parallel using the same solution of T amidite. An additional poly T four-mer was made with impurity XI at the third base from the 3' end. The four-mer was synthesized at the 10 μM scale on four columns in parallel and the support-bound oligonucleotide from each column was combined before cleavage. Samples were analyzed by IP-LC-MS unpurified with the 5' DMT attached.

Figure 12:
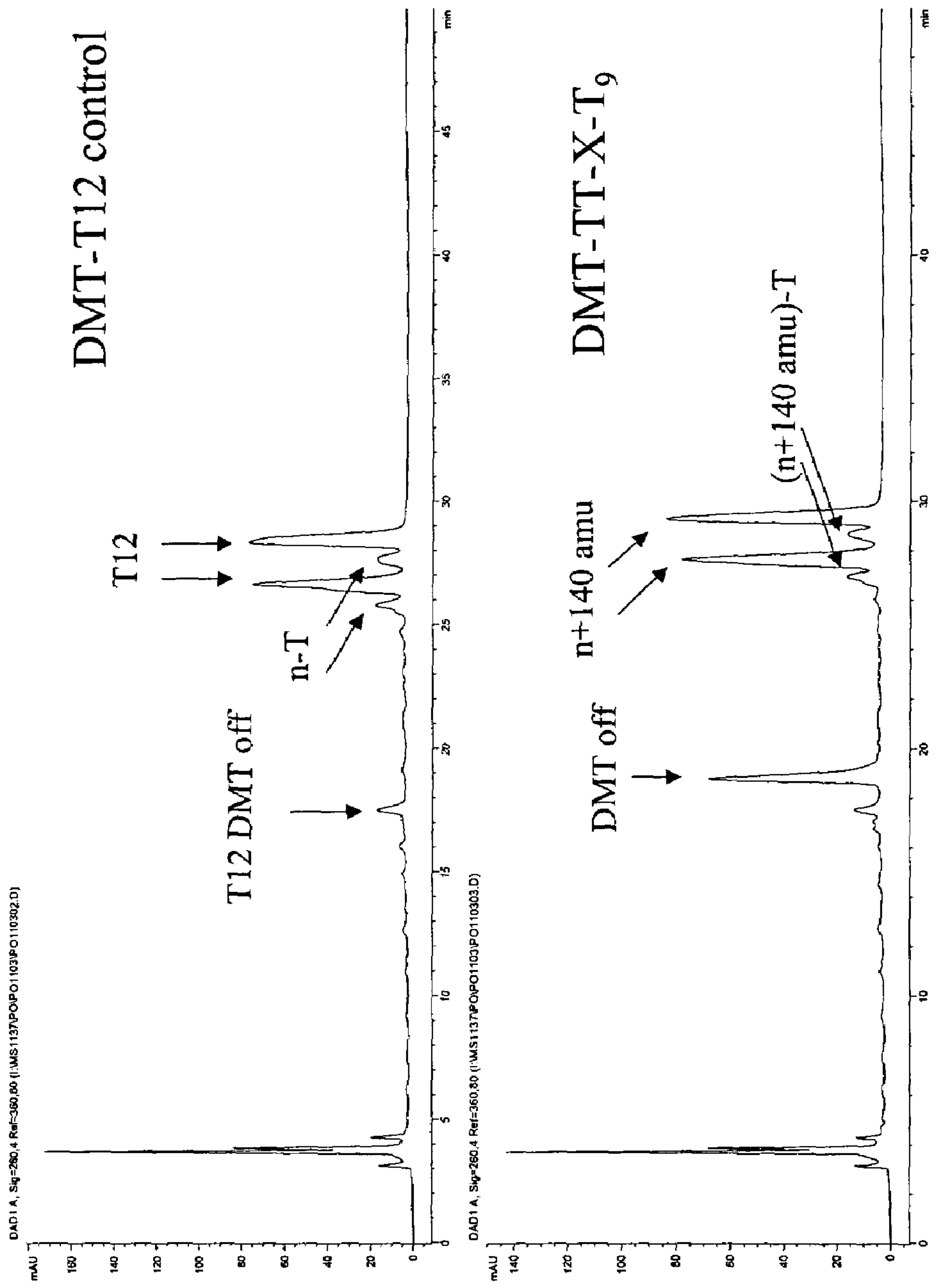
FIG. 12 shows UV chromatograms of the control and X twelve-mer.

When the structures of the impurities are considered, logical products can be predicted. Impurity X contains only one reactive amidite functionality the second phosphorus being a cyanoethyl phosphite. Once coupled to the growing oligonucleotide the second phosphite is sulfurized and the oligonucleotide is extended from the 5'OH in a regular manner. In this case a single product is produced, that being the n+140 amu version of the T twelve-mer. The UV chromatograms of the control and the impurity X twelve-mer are presented in FIG. 12. The most abundant isotopic masses for the control twelve-mer and the impurity X twelve-mer are shown in Table 2. These masses are compared to masses calculated from observed ions in different charge states. There is excellent agreement between these masses.

Masses for the Control and Impurity X Twelve-mers.

| Sequence | Most Abundant Isotopic Mass | Mass based on −3 charge state | Mass based on −4 charge state |
|---|---|---|---|
| T twelve-mer control | 4066.48 | 4066.5 | 4066.4 |
| Impurity X Twelve-mer n + 140 amu | 4206.45 | 4206.6 | 4206.0 |

Figure 13:
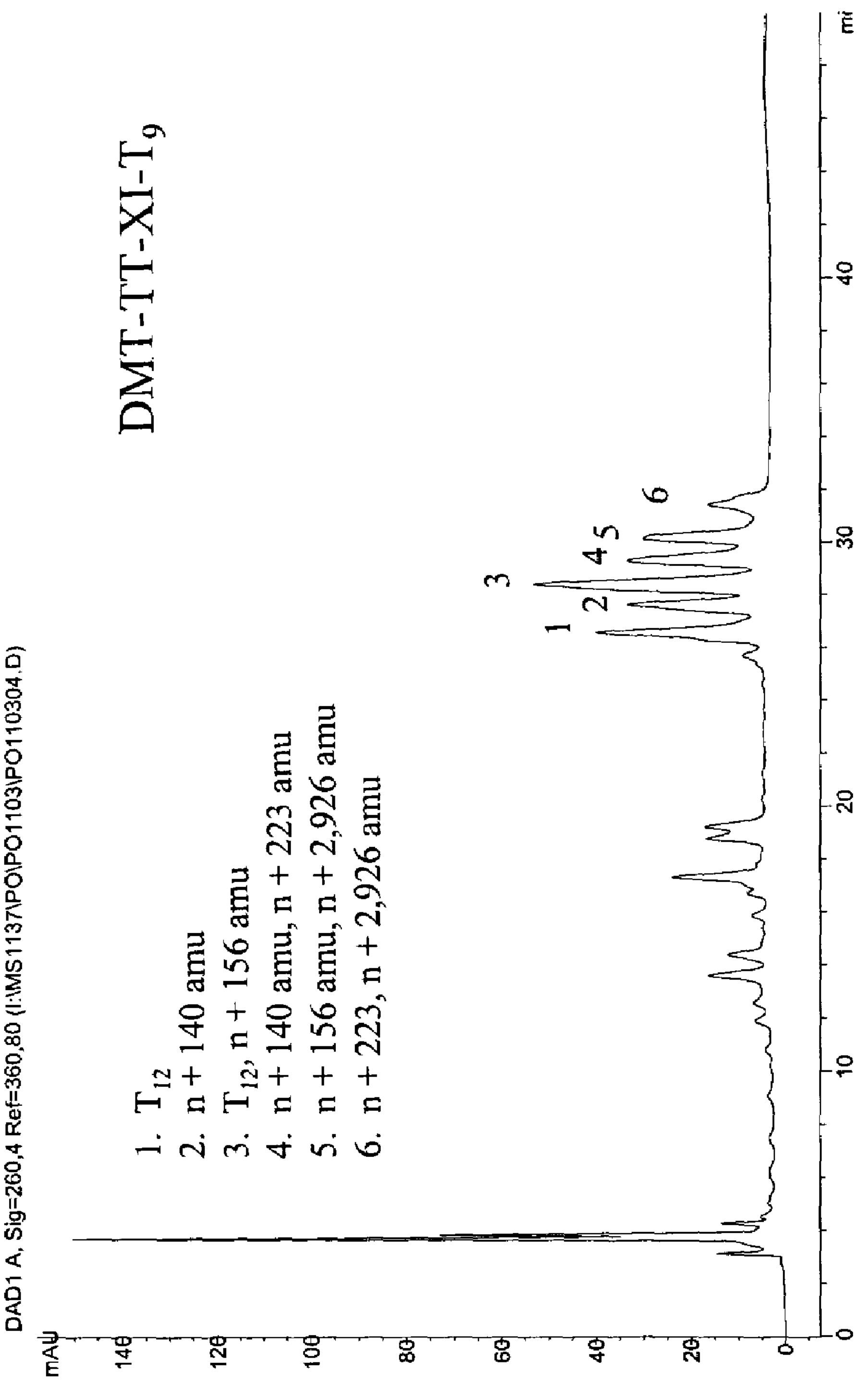
FIG. 13 shows a UV chromatogram of impurity XI twelve-mer.

Impurity XI has two reactive phosporoamidite groups and can produce a more complicated mixture of products. The UV chromatogram for the impurity XI twelve-mer is shown in FIG. 13. Part of this complexity is due to the fact that each species has two peaks if the 5' DMT is present when analyzed by this method. There are five primary products produced by this synthesis. Some of the unmodified T twelve-mer produced. There are also the n+140 amu, n+156 amu, n+223 amu impurities, and a fifth impurity much larger than the others with a mass of n+2,926 amu. The unmodified product is most likely formed when the amidite closest to the nucleoside couples and then the O-ethyl functionality is removed during ammonia cleavage. Formation of the n+140 amu impurity likely occurs when the amidite farthest from the nucleoside couples and the second amidite is ultimately converted to a phosphorothioate diester. If this second amidite is converted to a phosphorodithioate, n+156 amu is formed and if it is converted to a phosporothioamidate, n+223 amu is formed. The structures of the n+156 amu and n+223 amu impurities are presented below. The final impurity is formed if both amidites couple to the 5' end of different oligonucleotide chains bound to the support. The eventual product is one full length twelve-mer with an additional nine-mer 3' tail bridged by an ethyl phosphorothioate diester linkage.

Structures of the n+156 amu and n+223 amu Impurities

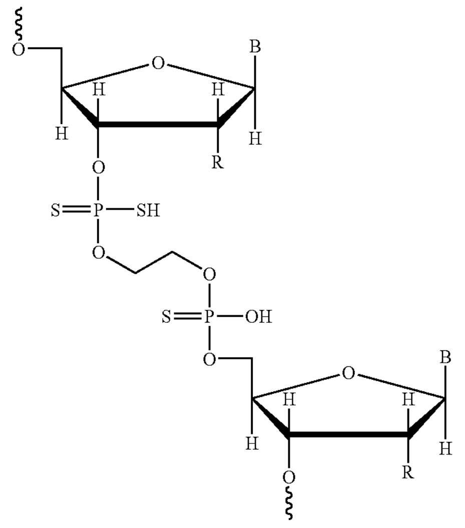

n + 156 amu

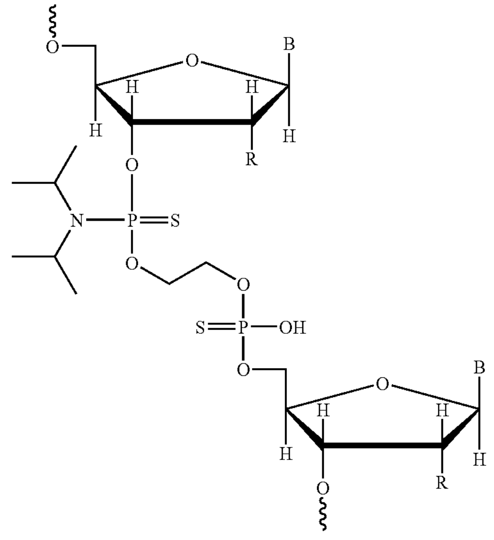

n + 223 amu

Structure of the n+2,926 amu Impurity

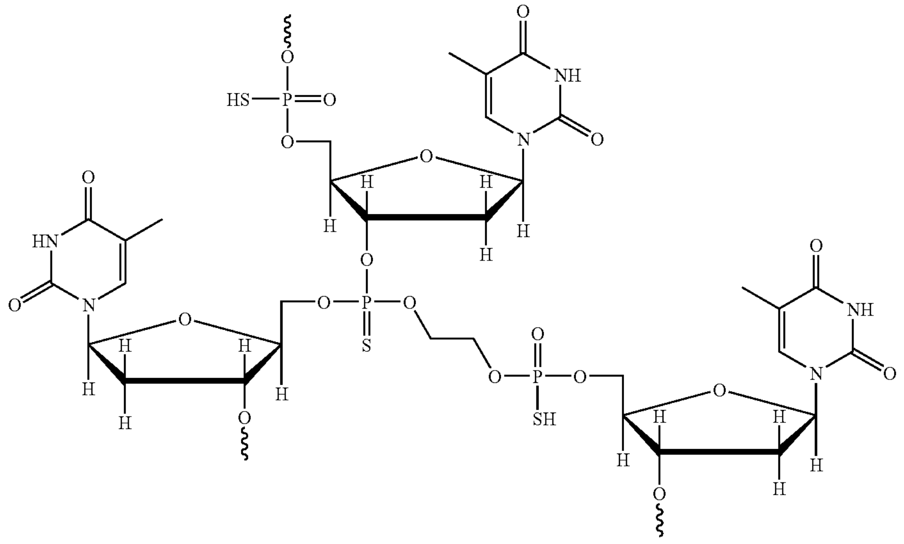

The most abundant isotopic masses for the major products of the impurity XI twelve-mer synthesis are shown in the table below. These masses are compared to masses calculated from observed ions in different charge states. As in the case of the X twelve-mer there is excellent agreement between these masses.

Masses of the Products for the Impurity XI Twelve-mers Synthesis.

| Sequence | Most Abundant Isotopic Mass | Mass based on −3 charge state | Mass based on −4 charge state |
|---|---|---|---|
| T twelve-mer | 4066.48 | 4066.5 | 4066.8 |
| T twelve-mer n + 140 amu | 4206.45 | 4206.6 | 4206.4 |
| T twelve-mer n + 156 amu | 4222.42 | 4222.4 | 4221.9 |
| T twelve-mer n + 223 amu | 4289.56 | 4290.8 | 4289.4 |

-continued

| Sequence | Most Abundant Isotopic Mass | Mass based on −3 charge state | Mass based on −4 charge state |
|---|---|---|---|
| T twelve-mer n + 2,926 amu | 6992.71 | 6993.0* | 6992.8 |

*Mass based on −5 charge state rather than −3

Impurity XVIII contains two phosphoroamidites and two nucleosides. When it reacts three primary products are formed. Like XI it can produce unmodified twelve-mer if the ethyl linkage is cleaved. If the linkage is not cleaved but the second amidite does not couple, a "Y" shaped oligo is produces as the chain is elongated from both nucleosides. If both amidites couple an "H" shape oligonucleotide is formed where two full length twelve-mers are linked together by an ethyl bridge. The structures of the "Y" and "H" oligonucleotides are shown below.

The "Y" and "H" Oligonucleotides Formed by Impurity XVIII

The "Y" shaped oligonucleotides

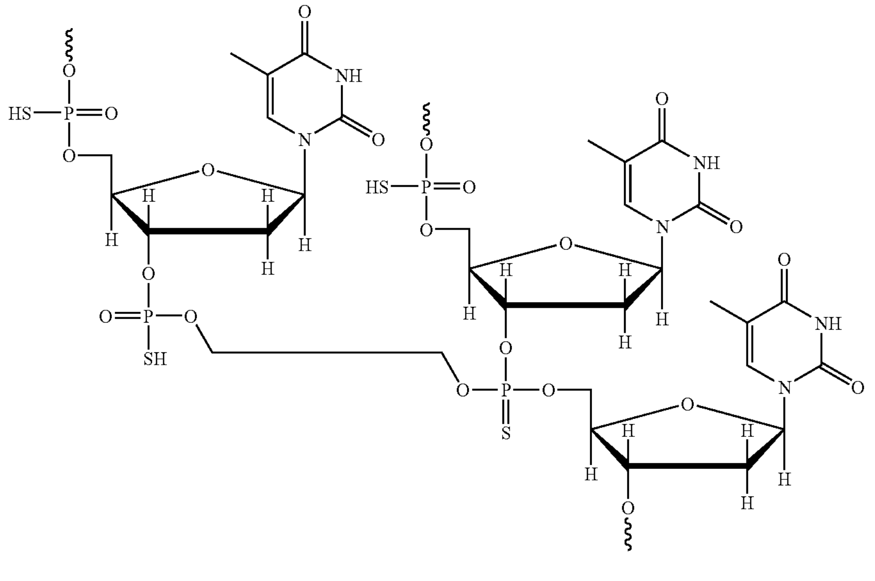

-continued

The "H" shaped oligonucleotide

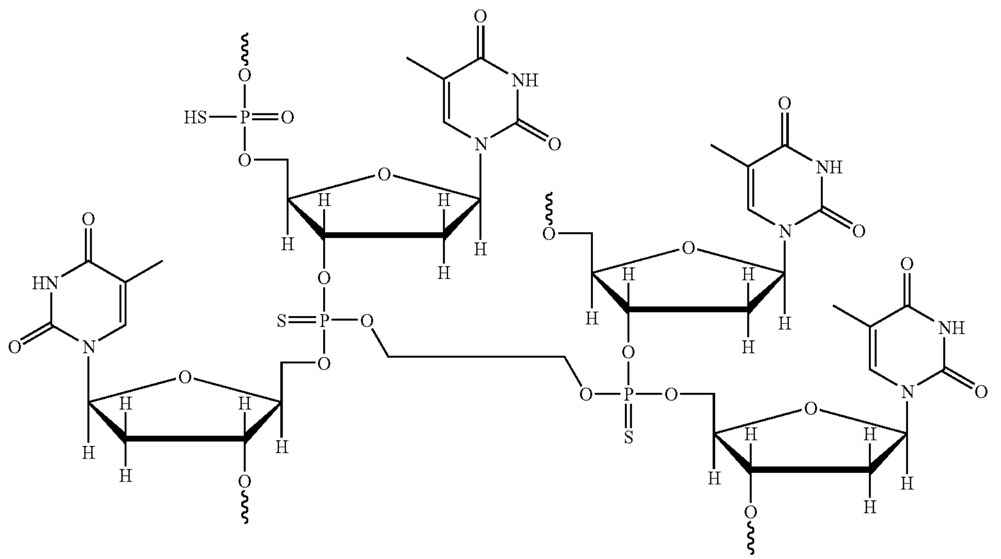

Figure 14:
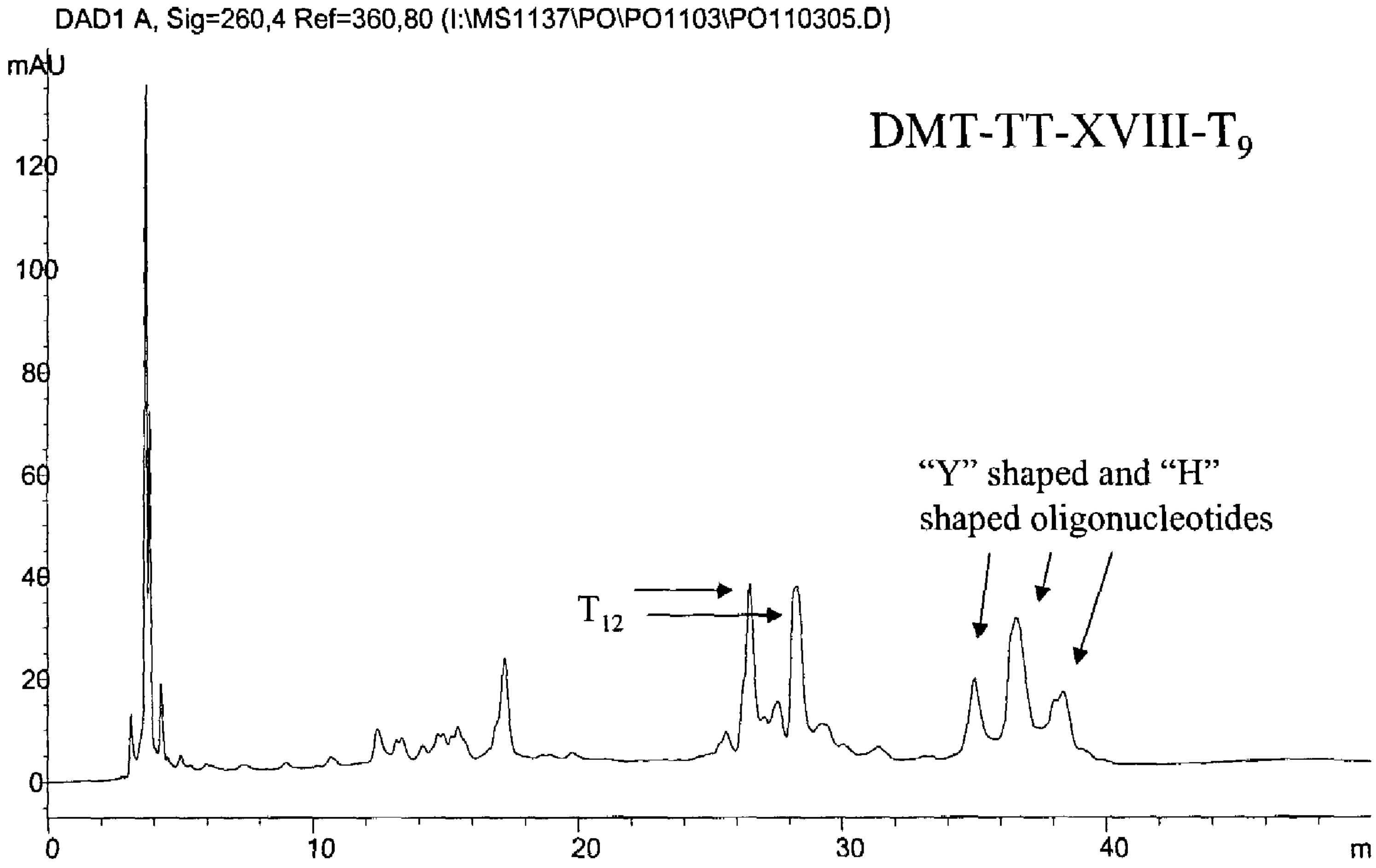
FIG. 14 shows a UV chromatogram of the XVIII synthesis.

The UV chromatogram of XVIII is shown in FIG. 14

The most abundant isotopic masses for the major products of the impurity XVIII twelve-mer synthesis are shown in the table below. These masses are compared to masses calculated from observed ions in different charge states. As in the case of the X and XI twelve-mers there is excellent agreement between these masses.

Masses of the Products for the Impurity XVIII Twelve-mers Synthesis.

| Sequence | Most Abundant Isotopic Mass | Mass based on −3 charge state | Mass based on −4 charge state |
|---|---|---|---|
| T twelve-mer | 4066.48 | 4066.8 | 4066.4 |
| "Y" shaped oligonucleotide | 5373.70 | 5373.9 | 5373.6 |
| "H" shaped oligonucleotide | 8159.97 | 8160.0* | Outside Scanned range |

*Mass based on −5 charge state rather than −3

O-ethyl amidite impurities X and XI are responsible for the n+140 amu impurity found in synthetic oligonucleotides. Impurity XI is also responsible for the n+156 amu and n+223 amu impurities. Based on the structure of XI and the mass of these two impurities logical structures have been proposed. While impurity X will only produce the impurity n+140 amu amidite authentics XI and XVIII can produce some full length unmodified sequence n. However, in addition to those impurities already mentioned XI produces one additional high molecular weight impurity and XVIII produces two.

These O-ethyl amidite impurities are formed by impurities in the phosphitilating reagent used for their preparation. These impurities are caused in turn by the presence of ethylene glycol in the cyanoethanol use to make the phosphitilating reagent. The primary commercial vendor of the phosphitilating reagent is aware of this issue and has put controls in place in order to prevent their formation. Impurities X, XI, and XVIII are easily detected by our LC/MS method and unsuitable amidite lots can be rejected before use.

Each reference cited in the present application, including but not limited to printed publications, patents and patent applications, is incorporated herein by reference in its entirety.

What is claimed is:

1. A compound of Formula I, II or III:

I

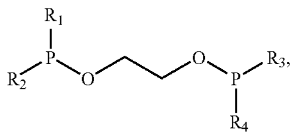

II

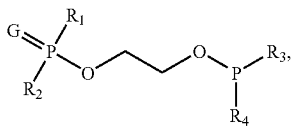

III

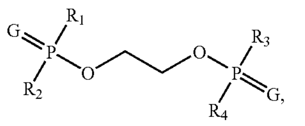

wherein each $R^1$, $R^2$, $R^3$ and $R^4$ is independently a 2'-O—, 3'-O—, or 5'-O— linked nucleoside optionally attached to solid support, a 2'-O—, 3'-O—, or 5'-O— linked oligonucleotide optionally attached to solid support, —$N^iPr_2$, —$O(CH_2)_2CN$, —OH or —SH, and each G us independently O or S.

2. A compound of Formula IV:

IV

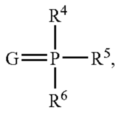

wherein each $R^4$, $R^5$ and $R^6$ is independently a 2'-O—, 3'-O—, or 5'-O— linked nucleoside optionally attached to solid support, or a 2'-O—, 3'-O—, or 5'-O— linked oligonucleotide optionally attached to solid support, G is O or S; and wherein at least one of said 2'-O—, 3'-O—, and 5'-O— linked nucleoside further comprises a phosphorus group.

3. A compound of Formula V:

V

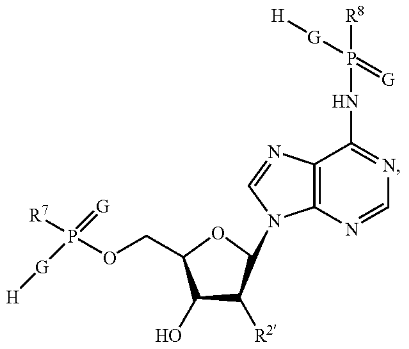

wherein $R^7$ and $R^8$ are independently a 2'-O—, 3'-O—, or 5'-O— linked nucleoside optionally attached to solid support, or a 2'-O—, 3'-O—, or 5'-O— linked oligonucleotide optionally attached to solid support, —SH or —OH, Each G is independently O or S, and $R_2$ is H, OH, O-rg wherein rg is a removable protection group, or a 2' substituent.

4. The compound of claim 1, wherein $R^1$, $R^2$, $R^3$ and $R^4$ are —$N^iPr_2$, or —$O(CH_2)_2CN$.

5. The compound of claim 1, wherein at least one of $R^1$, $R^2$, $R^3$ or $R^4$ is a 2'-O—, 3'-O—, or 5'-O— linked nucleoside optionally attached to solid support or a 2'-O—, 3'-O—, or 5'-O— linked oligonucleotide optionally attached to solid support.

6. The compound of claim 1, wherein at least two of $R^1$, $R^2$, $R^3$ or $R^4$ are 2'-O—, 3'-O—, or 5'-O— linked nucleosides optionally attached to solid support or 2'-O—, 3'-O—, or 5'-O— linked oligonucleotides optionally attached to solid support.

7. The compound of claim 1, wherein at least three of $R^1$, $R^2$, $R^3$ or $R^4$ are 2'-O—, 3'-O—, or 5'-O— linked nucleosides optionally attached to solid support or 2'-O—, 3'-O—, or 5'-O— linked oligonucleotides optionally attached to solid support.

8. The compound of claim 1, wherein $R^1$, $R^2$, $R^3$ and $R^4$ are 2'-O—, 3'-O—, or 5'-O— linked nucleosides optionally attached to solid support or 2'-O—, 3'-O—, or 5'-O— linked oligonucleotides optionally attached to solid support.

9. The compound of claim 1, wherein said 2'-O—, 3'-O—, or 5'-O— linked nucleosides or 2'-O—, 3'-O—, or 5'-O— linked oligonucleotides are not attached to solid support.

10. The compound of claim 2, wherein said 2'-O—, 3'-O—, or 5'-O— linked nucleosides or 2'-O—, 3'-O—, or 5'-O— linked oligonucleotides are not attached to solid support.

11. The compound of claim 3, wherein said 2'-O—, 3'-O—, or 5'-O— linked nucleosides or 2'-O—, 3'-O—, or 5'-O— linked oligonucleotides are not attached to solid support.

12. The compound of claim 1, wherein the purity of said compound is greater than about 1, 2, 3, 4, 5, 6, 7, 8, 9, or 10 percent.

13. The compound of claim 1, wherein the purity of said compound is greater than 10 percent.

14. The compound of claim 2, wherein the purity of said compound is greater than about 1, 2, 3, 4, 5, 6, 7, 8, 9, or 10 percent.

15. The compound of claim 2, wherein the purity of said compound is greater than 10 percent.

16. The compound of claim 3, wherein the purity of said compound is greater than about 1, 2, 3, 4, 5, 6, 7, 8, 9, or 10 percent.

17. The compound of claim 3, wherein the purity of said compound is greater than 10 percent.

18. A compound of Formula VII:

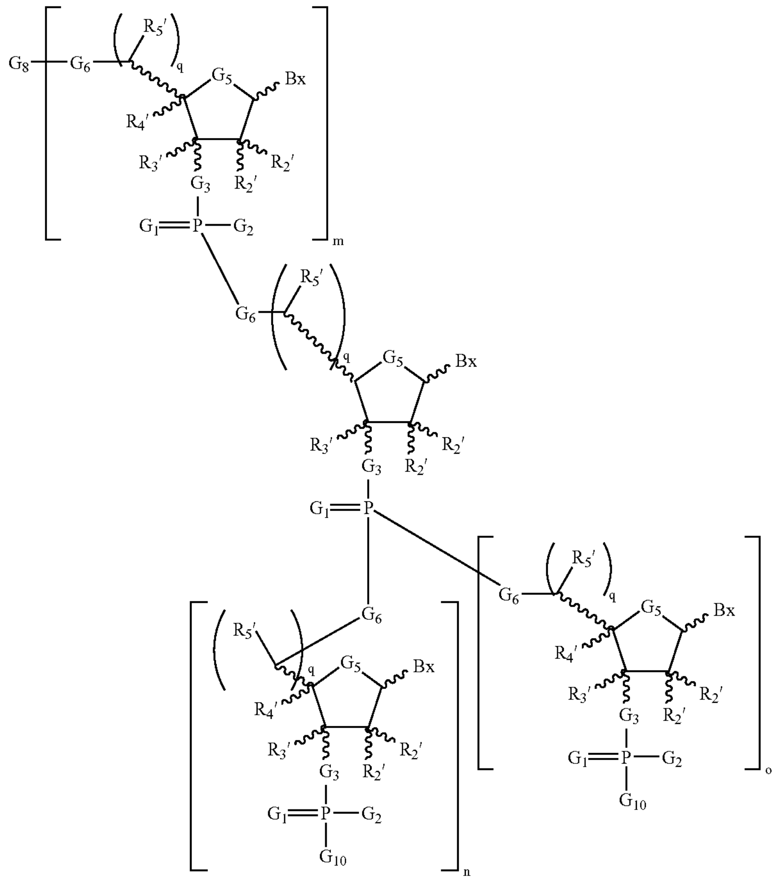

VII wherein:

each $G_1$ is, independently, O or S;

each $G_2$ is, independently, OH or SH;

each $G_3$ is, independently, O, S, $CH_2$, or NH;

each $G_5$ is, independently, O, S, $CH_2$, CFH, $CF_2$, or —CH=CH—;

each $R_2$' is, independently, H, OH, O-Pg, a 2'-substituent, or together with $R_4$' forms a bridge;

each $R_3$' is, independently, H, a substituent, or together with $R_4$' forms a bridge;

each $R_4$' is, independently, H, a substituent, or together with $R_2$' forms a bridge, together with $R_3$' forms a bridge, or together with $R_5$' forms a bridge;

each q is, independently, 0 or 1;

each $R_5$' is, independently, H, a substituent, or together with $R_4$' forms a bridge;

each $G_6$ is, independently, O, S, $CH_2$ or NH;

$G_8$ is H or a protecting group;

each $G_{10}$ is, independently, OH, O-Pg, a nucleoside, a nucleotide, or a nucleoside linked to a solid support or a nucleoside linked to a conjugate group;

Pg is a protecting group;

m is an integer from 1 to about 100;

n and o are each identical integers from 0 to about 100, provided that when n and o are 0, then each $G_{10}$ is an independently selected nucleoside linked to a solid support; and each Bx is a naturally occurring or modified nucleobase.

19. The compound of claim 18 wherein each $G_3$ is O or S.

20. The compound of claim 18 wherein each $G_1$ is S.

* * * * *